US012577544B2

(12) United States Patent
Naji et al.

(10) Patent No.: US 12,577,544 B2
(45) Date of Patent: *Mar. 17, 2026

(54) MODIFIED PH129 POLYMERASE AND USES THEREOF

(71) Applicant: Singular Genomics Systems, Inc., San Diego, CA (US)

(72) Inventors: Souad Naji, La Jolla, CA (US); Alexander Sevy, San Diego, CA (US); Jason Cellitti, San Diego, CA (US); Eli N. Glezer, Del Mar, CA (US); Bruna Krebs Kutche, San Diego, CA (US); Zachary Terranova, San Diego, CA (US); Sumit Handa, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/019,039

(22) Filed: Jan. 13, 2025

(65) Prior Publication Data

US 2025/0320474 A1 Oct. 16, 2025

Related U.S. Application Data

(63) Continuation of application No. 18/659,585, filed on May 9, 2024, now Pat. No. 12,227,774, which is a continuation of application No. PCT/US2023/075838, filed on Oct. 3, 2023.

(60) Provisional application No. 63/378,223, filed on Oct. 3, 2022, provisional application No. 63/493,180, filed on Mar. 30, 2023, provisional application No. 63/502,005, filed on May 12, 2023, provisional application No. 63/580,874, filed on Sep. 6, 2023.

(51) Int. Cl.
*C12N 9/12* (2006.01)
*C12Q 1/6844* (2018.01)

(52) U.S. Cl.
CPC ......... *C12N 9/1252* (2013.01); *C12Q 1/6844* (2013.01); *C12Y 207/07007* (2013.01)

(58) Field of Classification Search
None
See application file for complete search history.

(56) References Cited

U.S. PATENT DOCUMENTS

| | | | | |
|---|---|---|---|---|
| 5,001,050 | A | 3/1991 | Blanco et al. | |
| 5,198,543 | A | 3/1993 | Blanco et al. | |
| 5,576,204 | A | 11/1996 | Blanco et al. | |
| 8,343,746 | B2 | 1/2013 | Rank et al. | |
| 8,906,660 | B2 | 12/2014 | Kamtekar et al. | |
| 9,296,999 | B2 | 3/2016 | Kamtekar et al. | |
| 9,422,535 | B2 | 8/2016 | Skirgaila et al. | |
| 9,758,774 | B2 | 9/2017 | Kamtekar et al. | |
| 11,371,028 | B2 | 6/2022 | Ong et al. | |
| 12,227,774 | B2 * | 2/2025 | Naji | C12Q 1/6844 |
| 2008/0108082 | A1 | 5/2008 | Rank et al. | |
| 2011/0059505 | A1 | 3/2011 | Hanzel et al. | |
| 2011/0165652 | A1 | 7/2011 | Hardin et al. | |
| 2021/0261928 | A1 | 8/2021 | Kamtekar et al. | |
| 2022/0235337 | A1 | 7/2022 | Picher Serantes et al. | |
| 2022/0235410 | A1 | 7/2022 | Witters et al. | |
| 2024/0294887 | A1 | 9/2024 | Naji et al. | |

OTHER PUBLICATIONS

Accession P03680. (Jul. 21, 1986).
Bornscheuer, U. et al. (Nov. 1, 2011). "Survey of protein engineering strategies," *Current protocols in protein science* 66(1): 26-7.
Chica, R. A. et al. (Aug. 2005, e-published Jul. 1, 2005). "Semi-rational approaches to engineering enzyme activity: combining the benefits of directed evolution and rational design," *Current opinion in biotechnology* 16(4): 378-384.
De Vega, M. et al. (Sep. 21, 2010, e-published Sep. 7, 2010). "Improvement of q29 DNA polymerase amplification performance by fusion of DNA binding motifs," *PNAS* 107(38): 16506-16511.
Gao, Y. et al. (Jul. 2021, e-published May 19, 2021). "Chimeric Phi29 DNA polymerase with helix-hairpin-helix motifs shows enhanced salt tolerance and replication performance," *Microbial Biotechnology* 14(4): 1642-1656.
International Search Report and Written Opinion mailed on Apr. 12, 2024, for PCT Application No. PCT/US2023/075838, filed Oct. 3, 2023, 15 pages.
Li, Y. et al. (Jul. 2014, e-published May 6, 2014). "Recent advances in engineering proteins for biocatalysis," *Biotechnology and Bioengineering* 111(7): 1273-1287.
Lizardi, P. M. et al. (Jul. 1998). "Mutation detection and single-molecule counting using isothermal rolling-circle amplification," *Nat Genet* 19(3): 225-232.
Meijer, W. J. J. et al. (Jun. 1, 2001). "29 family of phages," *Microbiology and Molecular Biology Reviews* 65(2): 261-287.
Povilaitis, T. et al. (Dec. 28, 2016, e-published Nov. 28, 2016). "In vitro evolution of phi29 DNA polymerase using isothermal compartmentalized self replication technique," *Protein Engineering, Design and Selection* 29(12): 617-628.
Salas, M. (Dec. 15, 2016). "My scientific life," *Bacteriophage* 6(4): e1271250.
Singh, K. et al. (Jan. 1, 2018). "Protein engineering approaches in the post-genomic era," *Current Protein and Peptide Science* 19(1): 5-15.

* cited by examiner

*Primary Examiner* — Christian L Fronda

(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are mutant enzymes, kits, and methods of use thereof.

20 Claims, 4 Drawing Sheets

Specification includes a Sequence Listing.

FIG. 3

| | Amino Acid position wild type and BSTP6 | | | | | | | | | | | | | | | | | | | |
|---|---|---|---|---|---|---|---|---|---|---|---|---|---|---|---|---|---|---|---|---|
| | 312 | 313 | 314 | 315 | 316 | 317 | 318 | 319 | 320 | 321 | 322 | 323 | 324 | 325 | 326 | 327 | 328 | 329 | 330 | 331 |
| Wild type (SEQ ID NO:1) | G | N | E | Y | L | K | S | S | G | G | E | I | A | D | L | W | L | S | N | V |
| BSTP6 (SEQ ID NO:12) | G | N | E | Y | L | K | S | S | G | G | E | I | A | D | L | W | V | S | N | V |

| | | | | | | | | | | | | | | | | | | | | |
|---|---|---|---|---|---|---|---|---|---|---|---|---|---|---|---|---|---|---|---|---|
| MinWT (SEQ ID NO:2) | G | N | E | Y | L | K | S | S | G | G | E | I | A | D | L | W | L | S | N | V |
| BSTP4 (SEQ ID NO:8) | G | N | E | Y | L | K | S | S | G | G | E | I | A | D | L | W | L | S | N | V |
| Whiting18 (SEQ ID NO:17) | G | N | E | Y | L | K | S | S | G | G | E | I | A | D | L | W | V | S | N | V |
| Phage M2 (SEQ ID NO:20) | G | N | E | Y | L | K | N | S | G | V | E | P | V | E | L | Y | L | T | N | V |
| Beecentumtrevirus (SEQ ID NO:22) | G | N | E | Y | L | K | N | S | G | V | E | P | V | E | L | Y | L | T | N | V |
| | 309 | 310 | 311 | 312 | 313 | 314 | 315 | 316 | 317 | 318 | 319 | 320 | 321 | 322 | 323 | 324 | 325 | 326 | 327 | 328 |

Amino Acid position: MinWT, BSTP4, Whiting18, Phage M2, Beecentumtrevirus

SEQUENCE LISTING

```
Sequence total quantity: 54
SEQ ID NO: 1           moltype = AA  length = 575
FEATURE                Location/Qualifiers
source                 1..575
                       mol_type = protein
                       note = phage phi29
                       organism = Bacillus subtilis
SEQUENCE: 1
MKHMPRKMYS CDFETTTKVE DCRVWAYGYM NIEDHSEYKI GNSLDEFMAW VLKVQADLYF  60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                            575

SEQ ID NO: 2           moltype = AA  length = 572
FEATURE                Location/Qualifiers
source                 1..572
                       mol_type = protein
                       note = phage phi29
                       organism = Bacillus subtilis
SEQUENCE: 2
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYKITPEEY AYIKNDIQII AEALLIQFKQ  180
```

-continued

```
GLDRMTAGSD SLKGFKDIIT TKKFKKVFPT LSLGLDKEVR YAYRGGFTWL NDRFKEKEIG  240
EGMVFDVNSL YPAQMYSRLL PYGEPIVFEG KYVWDEDYPL HIQHIRCEFE LKEGYIPTIQ  300
IKRSRFYKGN EYLKSSGGEI ADLWLSNVDL ELMKEHYDLY NVEYISGLKF KATTGLFKDF  360
IDKWTYIKTT SEGAIKQLAK LMLNSLYGKF ASNPDVTGKV PYLKENGALG FRLGEEETKD  420
PVYTPMGVFI TAWARYTTIT AAQACYDRII YCDTDSIHLT GTEIPDVIKD IVDPKKLGYW  480
AHESTFKRAK YLRQKTYIQD IYMKEVDGKL VEGSPDDYTD IKFSVKCAGM TDKIKKEVTF  540
ENFKVGFSRK MKPKPVQVPG GVVLVDDTFT IK                                572

SEQ ID NO: 3            moltype = AA  length = 575
FEATURE                 Location/Qualifiers
source                  1..575
                        mol_type = protein
                        organism = Salasvirus phi29
SEQUENCE: 3
MKHMPRKMYS CDFETTTKVE DCRVWAYGYM NIEDHSEYKI GNSLDEFMAW VLKVQADLYF  60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                             575

SEQ ID NO: 4            moltype = AA  length = 572
FEATURE                 Location/Qualifiers
source                  1..572
                        mol_type = protein
                        note = Bacillus phage phi29
                        organism = unidentified
SEQUENCE: 4
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYKITPEEY AYIKNDIQII AEALLIQFKQ  180
GLDRMTAGSD SLKGFKDIIT TKKFKKVFPT LSLGLDKEVR YAYRGGFTWL NDRFKEKEIG  240
EGMVFDVNSL YPAQMYSRLL PYGEPIVFEG KYVWDEDYPL HIQHIRCEFE LKEGYIPTIQ  300
IKRSRFYKGN EYLKSSGGEI ADLWLSNVDL ELMKEHYDLY NVEYISGLKF KATTGLFKDF  360
IDKWTYIKTT SEGAIKQLAK LMLNSLYGKF ASNPDVTGKV PYLKENGALG FRLGEEETKD  420
PVYTPMGVFI TAWARYTTIT AAQACYDRII YCDTDSIHLT GTEIPDVIKD IVDPKKLGYW  480
AHESTFKRAK YLRQKTYIQD IYMKEVDGKL VEGSPDDYTD IKFSVKCAGM TDKIKKEVTF  540
ENFKVGFSRK MKPKPVQVPG GVVLVDDTFT IK                                572

SEQ ID NO: 5            moltype = AA  length = 348
FEATURE                 Location/Qualifiers
source                  1..348
                        mol_type = protein
                        note = oral taxon BU063 isolate
                        note = DNA polymerase
                        organism = Tannerella sp.
SEQUENCE: 5
GGFTWLNDRF KEKEIGEGMV FDVNSLYPAQ MYSRLLPYGE PIVFEGKYVW DEDYPLHIQH  60
IRCEFELKEG YIPTIQIKRS RFYKGNEYLK SSGGEIADLW LSNVDLELMK EHYDLYNVEY  120
ISGLKFKATT GLFKDFIDKW TYIKTTSEGA IKQLAKLMLN SLYGKFASNP DVTGKVPYLK  180
ENGALGFRLG EEETKDPVYT PMGVFITAWA RYTTITAAQA CYDRIIYCDT DSIHLTGTEI  240
PDVIKDIVDP KKLGYWAHES TFKRAKYLRQ KTYIQDIYMK EVDGKLVEGS PDDYTDIKFS  300
VKCAGMTDKI KKEVTFENFK VGFSRKMKPK PVQVPGGVVL VDDTFTIK                348

SEQ ID NO: 6            moltype = AA  length = 318
FEATURE                 Location/Qualifiers
source                  1..318
                        mol_type = protein
                        note = oral taxon BU063 isolate Cell 6/7/9
                        organism = Tannerella sp.
SEQUENCE: 6
MYSRLLPYGE PIVFEGKYVW DEDYPLHIQH IRCEFELKEG YIPTIQIKRS RFYKGNEYLK  60
SSGGEIADLW LSNVDLELMK EHYDLYNVEY ISGLKFKATT GLFKDFIDKW TYIKTTSEGA  120
IKQLAKLMLN SLYGKFASNP DVTGKVPYLK ENGALGFRLG EEETKDPVYT PMGVFITAWA  180
RYTTITAAQA CYDRIIYCDT DSIHLTGTEI PDVIKDIVDP KKLGYWAHES TFKRAKYLRQ  240
KTYIQDIYMK EVDGKLVEGS PDDYTDIKFS VKCAGMTDKI KKEVTFENFK VGFSRKMKPK  300
PVQVPGGVVL VDDTFTIK                                                318

SEQ ID NO: 7            moltype = AA  length = 594
FEATURE                 Location/Qualifiers
source                  1..594
                        mol_type = protein
                        note = High pressure processing (HPP)
                        organism = Escherichia coli
SEQUENCE: 7
```

-continued

```
MASMTGGQQM GRIRMPRKMY SCDFETTTKV EDCRVWAYGY MNIEDHSEYK IGNSLDEFMA  60
WVLKVQADLY FHNLKFDGAF IINWLERNGF KWSADGLPNT YNTIISRMGQ WYMIDICLGY  120
KGKRKIHTVI YDSLKKLPFP VKKIAKDFKL TVLKGDIDYH KERPVGYKIT PEEYAYIKND  180
IQIIAEALLI QFKQGLDRMT AGSDSLKGFK DIITTKKFKK VFPTLSLGLD KEVRYAYRGG  240
FTWLNDRFKE KEIGEGMVFD VNSLYPAQMY SRLLPYGEPI VFEGKYVWDE DYPLHIQHIR  300
CEFELKEGYI PTIQIKRSRF YKGNEYLKSS GGEIADLWLS NVDLELMKEH YDLYNVEYIS  360
GLKFKATTGL FKDFIDKWTY IKTTSEGAIK QLAKLMLNSL YGKFASNPDV TGKVPYLKEN  420
GALGFRLGEE ETKDPVYTPM GVFITAWARY TTITAAQACY DRIIYCDTDS IHLTGTEIPD  480
VIKDIVDPKK LGYWAHESTF KRAKYLRQKT YIQDIYMKEV DGKLVEGSPD DYTDIKFSVK  540
CAGMTDKIKK EVTFENFKVG FSRKMKPKPV QVPGGVVLVD DTFTIKLEHH HHHH        594

SEQ ID NO: 8           moltype = AA  length = 572
FEATURE                Location/Qualifiers
source                 1..572
                       mol_type = protein
                       note = DNA polymerase Bacillus phage BSTP4
                       organism = unidentified
SEQUENCE: 8
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYKITPEEY AYIKNDIQII AEALLIQFKQ  180
GLDRMTAGSD SLKGFKDIIT TKKFKKVFPT LSLGLDKEVR YAYRGGFTWL NDRFKEKEIG  240
EGMVFDVNSL YPAQMYSRLL PYGEPIAFEG KYVWDEDYPL HIQHIRCEFE LKEGYIPTIQ  300
IKRSRFYKGN EYLKSSGGEI ADLWLSNVDL ELMKEHYDLY NVEYISGLKF KATTGLFKDF  360
IDKWTYIKTT SEGAIKQLAK LMLNSLYGKF ASNPDVTGKV PYLKENGALG FRLGEEETKD  420
PVYTPMGVFI TAWARYTTIT AAQACYDRII YCDTDSIHLT GTEIPDVIKD IVDPKKLGYW  480
AHESTFKRAK YLRQKTYIQD IYMKEVDGKL VEGSPDDYTD IKFSVKCAGM TDKIKKEVTF  540
ENFKVGFSRK MKPKPVQVPG GVVLVDDTFT IK                                572

SEQ ID NO: 9           moltype = AA  length = 575
FEATURE                Location/Qualifiers
source                 1..575
                       mol_type = protein
                       note = Bacillus phage phi29 UPP.1
                       organism = unidentified
SEQUENCE: 9
MKHMPRKMYS CDFETTTKVE DCRVWAYGYM NIEDHSEYKI GNSLDEFMAW VLKVQADLYF  60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAERLLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RVKYLRQKTY IQDIYMKEVD GKLVEGSPDD YTDIKFSVKC AGMTDKIKKE  540
VTFENFKVGF SRKMKPKPVQ VPGGVVLVDD TFTIK                             575

SEQ ID NO: 10          moltype = AA  length = 575
FEATURE                Location/Qualifiers
source                 1..575
                       mol_type = protein
                       note = Bacillus phage phi29 UPP.2
                       organism = unidentified
SEQUENCE: 10
MKHMPRKMYS CDFETTTKVE DCRVWAYGYM NIEDHSEYKI GNSLDEFMAW VLKVQADLYF  60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAERLLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKVTTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                             575

SEQ ID NO: 11          moltype = AA  length = 575
FEATURE                Location/Qualifiers
source                 1..575
                       mol_type = protein
                       organism = Salasvirus phi29
SEQUENCE: 11
MKHMPRKMYS CAFETTTKVE DCRVWAYGYM NIEDHSEYKI GNSLDEFMAW VLKVQADLYF  60
HNLKFAGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
```

-continued

```
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                             575

SEQ ID NO: 12          moltype = AA  length = 575
FEATURE                Location/Qualifiers
source                 1..575
                       mol_type = protein
                       note = Primer terminal protein Bacillus phage BSTP6
                       organism = unidentified
SEQUENCE: 12
MKHMPRKMYS CDFETTTKVE DCRVWAYGYM NIENHSEYKI GNSLDEFMAW VLKVQADLYF  60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWVSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFDNFKVGF SRKMKPKPVQ VPGGVVLVDD TFTIK                             575

SEQ ID NO: 13          moltype = AA  length = 546
FEATURE                Location/Qualifiers
source                 1..546
                       mol_type = protein
                       organism = Bacillus velezensis
SEQUENCE: 13
MNIEDHSDYK IGNSLDEFMA WAMKVQADLY FHNLKFDGAF IINWLERNGF KWSADGLPNT  60
YNTIISRMGQ WYMIDICLGY KGKRKIHTVI YDSLKKLPFP VKKIAKDFKL TVLKGDIDYH  120
KERPVGYKIT PEEYAYIKND IQIIAEALLI QFKQGLDRMT AGSDSLKGFK DIITTKKFKK  180
VFPTLSLGLD KEVRYAYRGG FTWLNDRFKE KEIGEGMVFD VNSLYPAQMY SRLLPYGEPI  240
VFEGKYVWDE DYPLHIQHIR CEFELKEGYI PTIQIKRSRF YKGNEYLKSS GGEIADLWLS  300
NVDLELMKEH YDLYNVEYIS GLKFKATTGL FKDFIDKWTY IKTTSEGAIK QLAKLMLNSL  360
YGKFASNPDV TGKVPYLKEN GALGFRLGEE ETKDPVYTPM GVFITAWARY TTITAAQACY  420
DRIIYCDTDS IHLTGTEIPD VIKDIVDPKK LGYWAHESTF KRAKYLRQKT YIQDIYMKEV  480
DGKLVEGSPD DYTDIKFSVK CAGMTDKIKK EVTFENFKVG FSRKMKPKPV QVPGGVVLVD  540
DTFTIK                                                             546

SEQ ID NO: 14          moltype = AA  length = 572
FEATURE                Location/Qualifiers
source                 1..572
                       mol_type = protein
                       organism = Bacillus velezensis
SEQUENCE: 14
MSRKMYSCDF ETTTKVEDCR VWAYGYMNIE DHSDYKIGNS LDEFMAWAMK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYKITPEEY AYIKNDIQII AEALLIQFKQ  180
GLDRMTAGSD SLKGFKDIIT TKKFKKVFPT LSLGLDKEVR YAYRGGFTWL NDRFKEKEIG  240
EGMVFDVNSL YPAQMYSRLL PYGEPIVFEG KYVWDEDYPL HIQHIRCEFE LKEGYIPTIQ  300
IKRSRFYKGN EYLKSSGGEI ADLWLSNVDL ELMKEHYDLY NVEYISGLKF KATTGLFKDF  360
IDKWTYIKTT SEGAIKQLAK LMLNSLYGKF ASNPDVTGKV PYLKENGALG FRLGEEETKD  420
PVYTPMGVFI TAWARYTTIT AAQACYDRII YCDTDSIHLT GTEIPDVIKD IVDPKKLGYW  480
AHESTFKRAK YLRQKTYIQD IYMKEVDGKL VEGSPDDYTD IKFSVKCAGM TDKIKKEVTF  540
ENFKVGFSRK MKPKPVQVPG GVVLVDDTFT IK                                572

SEQ ID NO: 15          moltype = AA  length = 572
FEATURE                Location/Qualifiers
source                 1..572
                       mol_type = protein
                       note = DNA polymerase Bacillus phage Arbo1
                       organism = unidentified
SEQUENCE: 15
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYEITPDEY AYIKNDIQII AEALLIQFKQ  180
GLDRMTAGSD SLKGFKDIIT TKKFKKVFPT LSLGLDKEVR YAYRGGFTWL NDRFKEKEIG  240
EGMVFDVNSL YPAQMYSRLL PYGEPIVFEG KYVWDEDYPL HIQHIRCEFE LKEGYIPTIQ  300
IKRSRFYKGN EYLKSSGGEI ADLWVSNVDL ELMKEHYDLY NVEYISGLKF KATTGLFKDF  360
IDKWTHIKTT SEGAIKQLAK LMLNSLYGKF ASNPDVTGKV PYLKENGALG FRLGEEETKD  420
PVYTPMGVFI TAWARYTTIT AAQACFDRII YCDTDSIHLT GTEIPDVIKD IVDPKKLGYW  480
AHESTFKRAK YLRQKTYIQD IYMKEVDGKL VEGSPDDYTT IKFSVKCAGM TDKIKKEVTF  540
DNFKVGFSRK MKPKPVQVPG GVVLVDDTFT IK                                572

SEQ ID NO: 16          moltype = AA  length = 572
FEATURE                Location/Qualifiers
source                 1..572
                       mol_type = protein
                       note = DNA polymerase Bacillus phage PZA H3027_gp06
                       organism = unidentified
```

-continued

```
SEQUENCE: 16
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYEITPDEY AYIKNDIQII AEALLIQFKQ  180
GLDRMTAGSD DLKGFKDIIT TKKFKKVFPT LSLGLDKEVR YAYRGGFTWL NDRFKEKEIG  240
EGMVFDVNSL YPAQMYSRLL PYGEPIVFEG KYVWDEDYPL HIQHIRCEFE LKEGYIPTIQ  300
IKRSRFYKGN EYLKSSGGEI ADLWVSNVDL ELMKEHYDLY NVEYISGLKF KATTGLFKDF  360
IDKWTHIKTT SEGAIKQLAK LMLNSLYGKF ASNPDVTGKV PYLKENGALG FRLGEEETKD  420
PVYTPMGVFI TAWARYTTIT AAQACFDRII YCDTDSIHLT GTEIPDVIKD IVDPKKLGYW  480
AHESTFKRAK YLRQKTYIQD IYMKEVDGKL VEGSPDDYTT IKFSVKCAGM TDKIKKEVTF  540
ENFKVGFSRK MKPKPVQVPG GVVLVDDTFT IK                               572

SEQ ID NO: 17          moltype = AA  length = 572
FEATURE                Location/Qualifiers
source                 1..572
                       mol_type = protein
                       note = Bacillus phage Whiting18
                       organism = unidentified
SEQUENCE: 17
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYEITPDEY AYIKNDIQII AEALLIQFKQ  180
GLDRMTAGSD SLKGFKDIIT TKKFKKVFPT LSLGLDKEVR YAYRGGFTWL NDRFKEKEIG  240
EGMVFDVNSL YPAQMYSRLL PYGEPIVFEG KYVWDEDYPL HIQHIRCEFE LKEGYIPTIQ  300
IKRSRFYKGN EYLKSSGGEI ADLWVSNVDL ELMKEHYDLY NVEYISGLKF KATTGLFKDF  360
IDKWTHIKTT SEGAIKQLAK LMLNSLYGKF ASNPDVTGKV PYLKENGALG FRLGEEETKD  420
PVYTPMGVFI TAWARYTTIT AAQACFDRII YCDTDSIHLT GTETPDVIKD IVDPKKLGYW  480
AHESTFKRAK YLRQKTYIQD IYMKEVDGKL VEGSPDDYTT IKFSVKCAGM TDKIKKEVTF  540
DNFKVGFSRK MKPKPVQVPG GVVLVDDTFT IK                               572

SEQ ID NO: 18          moltype = AA  length = 572
FEATURE                Location/Qualifiers
source                 1..572
                       mol_type = protein
                       note = DNA polymerase Bacillus phage vB_BveP-Goe6
                       organism = unidentified
SEQUENCE: 18
MPRKMYSCDF ETTTKVEDCR VWAYGYMNIE DHSEYKIGNS LDEFMAWVLK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYKITPEEY AYIKNDIQII AEALLIQFKQ  180
GLDRMTAGSD SLKGFKDIIT TKKFKKVFPT LSLGLDKEVR YAYRGGFTWL NDRFKEKEIG  240
EGMVFDVNSL YPSQMYSRLL PYGEPIVFEG KYVWDEDYPL HIQHIRCEFE LKEGYIPTIQ  300
IKRSRFYKGN EYLKSSGGEI ADLWLSNVDL ELMKEHYDLY NVEYISGLKF KATTGLFKDF  360
IDKWTYIKTT SEGAIKQLAK LMLNSLYGKF ASNPDVTGKV PYLKENGALG FRLGEEETKD  420
PVYTPMGVFI TAWARYTTIT AAQACYDRII YCDTDSIHLT GTEIPDVIKD IVDDNKLGYW  480
AHESTFKRAK YLRQKTYIQD IYMKEVNGKP VPASPDDYTF IKFSVKCAGM TDKIKKEVTF  540
DNFKVGFSRK MKPKPVQVPG GVVLVDDTFT IK                               572

SEQ ID NO: 19          moltype = AA  length = 572
FEATURE                Location/Qualifiers
source                 1..572
                       mol_type = protein
                       note = DNA polymerase protein Bacillus phage TBA3
                       organism = unidentified
SEQUENCE: 19
MPRKMYSCDF ETTTKVEDCR VWAYGYMNIE DHSEYKIGNS LDEFMAWVMK VQADLYFHNL  60
KFDGAFIINW LERNGFKWSA DGLPNTYNTI ISRMGQWYMI DICLGYKGKR KIHTVIYDSL  120
KKLPFPVKKI AKDFKLTVLK GDIDYHKERP VGYKITPEEY AYIKNDIQII AEALLIQFKQ  180
GLDRMTAGSD SLKGFKDIIT AKKFKKVFPT LSLGLDKEVR YAYRGGFTWL NDRFKDKEIG  240
EGMVFDVNSL YPSQMYTRLL PYGEPIVFEG KYVWDEDYPL HIQHIRCEFE LKEGYIPTIQ  300
IKRSRFYKGN EYLKSSGGEI ADLWLSNVDL ELMKEHYDLY NVEYISGLKF KATTGLFKDF  360
IDKWTYIKTT SEGAIKQLAK LMLNSLYGKF ASNPDVTGKV PYLKENGALG FRLGEEETKD  420
PVYTPMGVFI TAWARYTTIT AAQACYDRII YCDTDSIHLT GTEIPDVIKD IVDDNKLGYW  480
AHESTFKRAK YLRQKTYIQD IYMKEVDGKP VPASPDDYTF IKFSVKCAGM TDKIKKEVTF  540
ENFKVGFSRK MKPKPVQVPG GVVLVDDTFT IK                               572

SEQ ID NO: 20          moltype = AA  length = 572
FEATURE                Location/Qualifiers
source                 1..572
                       mol_type = protein
                       note = Bacillus phage M2
                       organism = unidentified
SEQUENCE: 20
MSRKMFSCDF ETTTKLDDCR VWAYGYMEIG NLDNYKIGNS LDEFMQWVME IQADLYFHNL  60
KFDGAFIVNW LEQHGFKWSN EGLPNTYNTI ISKMGQWYMI DICFGYKGKR KLHTVIYDSL  120
KKLPFPVKKI AKDFQLPLLK GDIDYHTERP VGHEITPEEY EYIKNDIEII ARALDIQFKQ  180
GLDRMTAGSD SLKGFKDILS TKKFNKVFPK LSLPMDKEIR KAYRGGFTWL NDKYKEKEIG  240
EGMVFDVNSL YPSQMYSRPL PYGAPIVFQG KYEKDEQYPL YIQRIRFEFE LKEGYIPTIQ  300
IKKNPFFKGN EYLKNSGVEP VELYLTNVDL ELIQEHYELY NVEYIDGFKF REKTGLFKDF  360
```

-continued

```
IDKWTYVKTH EEGAKKQLAK LMLNSLYGKF ASNPDVTGKV PYLKDDGSLG FRVGDEEYKD  420
PVYTPMGVFI TAWARFTTIT AAQACYDRII YCDTDSIHLT GTEVPEIIKD IVDPKKLGYW  480
AHESTFKRAK YLRQKTYIQD IYVKEVDGKL KECSPDEATT TKFSVKCAGM TDTIKKKVTF  540
DNFAVGFSSM GKPKPVQVNG GVVLVDSVFT IK                               572

SEQ ID NO: 21          moltype = AA  length = 572
FEATURE                Location/Qualifiers
source                 1..572
                       mol_type = protein
                       note = DNA polymerase Bacillus phage vB_BsuP-Goe1
                       organism = unidentified
SEQUENCE: 21
MSRKMFSCDF ETTTKLDDCR VWAYGYMEIG NLDNYKIGNS LDEFMKWVME IQADLYFHNL  60
KFDGAFIVNW LEQHGFKWSN EGLPNTYHTI ISKMGQWYMI DICFGYRGKR KLHTVIYDSL  120
KKLPFPVKKI AKDFQLPLLK GDIDYHTERP VGHEITPEEY EYIKNDIEII ARALDIQFKQ  180
GLDRMTAGSD SLKGFKDILS TKKFNKVFPK LSLPMDKEIR KAYRGGFTWL NDKYKEKEIG  240
EGMVFDVNSL YPSQMYSRPL PYGAPIVFQG KYEKDEQYPL YIQRIRFEFE LKEGYIPTIQ  300
IKKNPFFKGN EYLKNSGAEP VELYLTNVDL ELIQEHYELY NVEYIDGFKF REKTGLFKDF  360
IDKWTYVKTH EEGAKKQLAK LMLNSLYGKF ASNPDVTGKV PYLKDDGSLG FRVGDEEYKD  420
PVYTPMGVFI TAWARFTTIT AAQACYDRII YCDTDSIHLT GTEVPEIIKD IVDPKKLGYW  480
AHESTFKRAK YLRQKTYIQD IYVKEVDGKL KECSPDEATT TKFSVKCAGM TDTIKKKVTF  540
DNFKVGFSSM GKPKPVQVNG GVVLVDSVFT IK                               572

SEQ ID NO: 22          moltype = AA  length = 572
FEATURE                Location/Qualifiers
source                 1..572
                       mol_type = protein
                       organism = Beecentumtrevirus Nf
SEQUENCE: 22
MSRKMFSCDF ETTTKLDDCR VWAYGYMEIG NLDNYKIGNS LDEFMQWVME IQADLYFHNL  60
KFDGAFIVNW LEQHGFKWSN EGLPNTYNTI ISKMGQWYMI DICFGYRGKR KLHTVIYDSL  120
KKLPFPVKKI AKDFQLPLLK GDIDYHTERP VGHEITPEEY EYIKNDIEII ARALDIQFKQ  180
GLDRMTAGSD SLKGFKDILS TKKFNKVFPK LSLPMDKEIR KAYRGGFTWL NDKYKEKEIG  240
EGMVFDVNSL YPSQMYSRPL PYGAPIVFQG KYEKDEQYPL YIQRIRFEFE LKEGYIPTIQ  300
IKKNPFFKGN EYLKNSGVEP VELYLTNVDL ELIQEHYELY NVEYIDGFKF REKTGLFKDF  360
IDKWTYVKTH EEGAKKQLAK LMLNSLYGKF ASNPDVTGKV PYLKDDGSLG FRVGDEEYKD  420
PVYTPMGVFI TAWARFTTIT AAQACYDRII YCDTDSIHLT GTEVPEIIKD IVDPKKLGYW  480
AHESTFKRAK YLRQKTYIQD IYVKEVDGKL KECSPDEATT TKFSVKCAGM TDTIKKKVTF  540
DNFAVGFSSM GKPKPVQVNG GVVLVDSVFT IK                               572

SEQ ID NO: 23          moltype = AA  length = 572
FEATURE                Location/Qualifiers
source                 1..572
                       mol_type = protein
                       organism = Beecentumtrevirus B103
SEQUENCE: 23
MPRKMFSCDF ETTTKLDDCR VWAYGYMEIG NLDNYKIGNS LDEFMQWVME IQADLYFHNL  60
KFDGAFIVNW LEHHGFKWSN EGLPNTYNTI ISKMGQWYMI DICFGYKGKR KLHTVIYDSL  120
KKLPFPVKKI AKDFQLPLLK GDIDYHAERP VGHEITPEEY EYIKNDIEII ARALDIQFKQ  180
GLDRMTAGSD SLKGFKDILS TKKFNKVFPK LSLPMDKEIR RAYRGGFTWL NDKYKEKEIG  240
EGMVFDVNSL YPSQMYSRPL PYGAPIVFQG KYEKDEQYPL YIQRIRFEFE LKEGYIPTIQ  300
IKKNPFFKGN EYLKNSGAEP VELYLTNVDL ELIQEHYEMY NVEYIDGFKF REKTGLFKEF  360
IDKWTYVKTH EKGAKKQLAK LMFDSLYGKF ASNPDVTGKV PYLKEDGSLG FRVGDEEYKD  420
PVYTPMGVFI TAWARFTTIT AAQACYDRII YCDTDSIHLT GTEVPEIIKD IVDPKKLGYW  480
AHESTFKRAK YLRQKTYIQD IYAKEVDGKL IECSPDEATT TKFSVKCAGM TDTIKKKVTF  540
DNFRVGFSST GKPKPVQVNG GVVLVDSVFT IK                               572

SEQ ID NO: 24          moltype = AA  length = 607
FEATURE                Location/Qualifiers
source                 1..607
                       mol_type = protein
                       note = DNA polymerase Cytobacillus phage Bfsp1
                       organism = Cytobacillus firmus
SEQUENCE: 24
MARKQFMCDF ETTTDIDDCR VWAYGYMEIG NKQNYKIGNS IEEFMEWAEK SRSDIYFHNL  60
KFDGSFIVNW LLNNGYTWEH MNEKSGKPKT FTTIISNMGQ WYMVDICYGR KGKRLLHTKI  120
YDSLKKLPFS VKQIAKAFKL PIMKGDIDYT KPRPVGYEIT PDEEEYIYGD LFIVASALET  180
QFEQGLTKMT SGSDSLSGFK DILTPKMFDK FFPVLDLRID SEIRKAYRGG FTWVNDTIQG  240
QTIGEGMVFD VNSLYPSRMY DCDLPYGTPE KFEGEYTYNE TYPLYIQVLK CSFELKEGYI  300
PTIQLKQTAR YRDNEYLKSS NHEIETLYVT NVDLELIKEH YDLYDVEYLG GYMFKKKNDL  360
FREFIDYWMH IKITSTGAIK QLAKLMLNSL YGKFASNPVV TGKIPYLKED GRNGFKLPVK  420
EGEFQEVKGK LIPVIDEEYK EPVYTAMGAF ITAWARHYTI TTAQKCFDRI CYCDTDSIHI  480
KGTEIPEVIK DIIDPDKLGY WNHESTFIRA KFIRQKTYIE DTCFKMVEKN GKLEKVGAGL  540
DDYEFTEIEV KCAGMPENLK KYVTWENFNV FNEDMLLPAR DGYWYGKLMP KQVPGGVVLV  600
ESDFAIR                                                           607

SEQ ID NO: 25          moltype = AA  length = 586
FEATURE                Location/Qualifiers
source                 1..586
```

```
                        mol_type = protein
                        note = DNA polymerase Bacillus phage vB_Bpu_PumA1
                        organism = Bacillus pumilus
SEQUENCE: 25
MARKKYSCDF ETTTDPLDCR VWAYGYMEIG KDSNYKIGNS LDEFMEWVSK CNADLYFHNL  60
RFDGEFILIW LLQNGFKWSD KRKPEPMTFN GVISRDNAVY RYDICYGYTN SGKKIHTVIY  120
DSYKKLPYPV KVIAKAFNLT QLKGDIDYDA YRPVGHKITK EEYKYIYNDI KIIADALKIQ  180
FEQGLKKMTI GSDSLNGFKS IFGKKQFEKT FPVLDMLTDD FIRLSYKGGF TWLNPKFANI  240
VINKGRVYDV NSMYPAIMYN ELLPYGVPVR FKGKYEKDDK YPLYIQQISC IFELKEGKIP  300
MIQVKNEPLK FKGSEYLTSS KGYEVKLTLT NVELELFLEN YKLNCVEYLG GYKFRGVRGL  360
FKTFIDKWMN IKMNSEGAIR ELAKLMLNNL YGKFATNPDV TGKYPELKED GSLGFKMKPR  420
ELSEPVYTAM GSFITAYGRC MTVRTGQSCY DRFIYADTDS VHVAGNEDIP EIADKIDSKK  480
LGYWDHEATF ETGKYVRSKA YFLNLYAKKV VKDGEEIIKP CGEEEATTRK RKVACAGMPE  540
TLRNIVPFEE FKIGYTGTRL APRHVKGGIV LVDAPYTLKE DIWRYA                586

SEQ ID NO: 26           moltype = AA  length = 830
FEATURE                 Location/Qualifiers
source                  1..830
                        mol_type = protein
                        note = protein FF38_11041
                        organism = Lucilia cuprina
SEQUENCE: 26
MARKRPIRIT KNDRAEYKRL SKNAKSKLNR TVKNYGIDLS NDVDIPKLSD FKTRKEFNDW  60
KQKITSFTSR SNQEYQFRKN EYGVVASVKE LNEIKRNTKK AQKIAKEKID KAMKLDFYVE  120
GERQGKVKDR IKLMKKEEVA GVSVPVDFDF DKIQTRKRLE DKAGFMEERA TGDYYRKKDI  180
QMKENFISMI EQGFNSDADE VIKKLKKIPP DDFVELTIVT DEIDFRNYGS KNEGGINDED  240
KLEELNNTLN DYFNETTTDV NDCRVWAYGW MEIGKTSNYK IGTDFNEFME WMIHSSSRLY  300
FHNLKFDGSF IVNWLLHNGY TWTKRPSKEG QFSTLISKMG QWYGITICSG RDGRKKKLTT  360
IHDSLKKLPF PVRKIGKDFK LNVLKGDIDY HKPRPIGYEI DDEEYQYIKN DIQIIAEALE  420
VQTVQGLTGM TNGKDALDEF VNMSGKLYEK LFPVFSLELN EEIRKAYRGG FTWLNPVYGT  480
KKYVKDGIVF DVNSLYPSQM YDRDLPCGVP IPFEGEYVYD KSHPLYIQKL TFEFELKENY  540
IPTIQLKNSR FGFKGNEYLS SSNGERITIS VSSVDWELIR EHYHVYDVEF EKGWKFRSTK  600
QAFRQYIDKW MLVKNMSAGA KKAIAKLMLN SLYGKFATNP DITGKRPYLR EDGSNGFELM  660
EEEFRDPVYT PVGIFITSWA RYTTITSAQK CYDRIIYCDT DSMHLEGLDV PESIKDIVAD  720
DVLGYWKKEG QFKQGKFIRQ KTYMEEYYAK YVRDENGEIK YDDEKPIKTI CDKEESDTTI  780
IEIKCAGMPD NIKKHVTFDN FDIGFTMEGK LKPKQVYGGV VLVEETYTMK            830

SEQ ID NO: 27           moltype = AA  length = 608
FEATURE                 Location/Qualifiers
source                  1..608
                        mol_type = protein
                        note = DNA polymerase Bacillus phage BeachBum
                        organism = Bacillus thuringiensis
SEQUENCE: 27
MGNKKRKIYS CDFETTTDVN DCRVWAYGLM EIDGKFENYK EGNNIDEFME WAEKEQGDLY  60
FHNLRFDGEF IVNWLLHKGY RFNNTRKAGT FNAVISSMGQ WYKIDIYYGR EGKKVFKTSI  120
YDSLKKLPFP VKTIAKAFKL PIEKGDIDYD APRPVGHQIT PDESKYIKND VEIIARALHS  180
QLNTAKLTKM TIGSDALDGF KHSLHKSPKV SKRMYDHHFP VISNAIHEEF KKAYRGGFTW  240
ANPKYAGKVI GNGLVFDVNS LYPSVMYDKP LPYGLPVPFS GEYEYDETHP LFIQHIRCGF  300
ELKEGHIPTI QIKKNFRFAD NEYLHSSEGN ILDLHVTNVD LALIKEHYTL YEEEYLQGYK  360
FKQVTGLFKN YIDYWSDKKI NAEDPAIRQM AKLMLNSLYG KFGTSIDVTG KEVFLKEDGS  420
TGFRKGQKEE RDPVYMPMGA FITAYARDVT IRTAQKCYDR ILYCDTDSIH LVGTEIPEAI  480
KDRIHDKKLG YWAHESTFWR AKFIRQKTYI EDLCMRFEGE RVNGEWKFKM VEEKDITKAT  540
ARELSVKCAG MPAQVKQYVT FDNFGVDFKH DPNDFTEEEI KRKNIKFKLK PTHRKGGQVL  600
VPTPFTIK                                                          608

SEQ ID NO: 28           moltype = AA  length = 608
FEATURE                 Location/Qualifiers
source                  1..608
                        mol_type = protein
                        note = DNA polymerase Bacillus phage Harambe
                        organism = Bacillus thuringiensis
SEQUENCE: 28
MGNKKRKIYS CDFETTTDVN DCRVWAYGLM EIDGKFENYK EGNNIDEFME WTEQEQGDLY  60
FHNLRFDGEF IVNWLLHKGY RFNNTRKAGT FNAVISSMGQ WYKIDIYYGR EGKKVFKTSI  120
YDSLKKLPFP VKTIAKAFKL PIEKGDIDYD APRPVGHQIT PDESKYIKND VEIIARALHS  180
QLNTAKLTKM TIGSDALDGF KHSLHKSPKV SKRMYDHHFP VISNAIHEEF KKAYRGGFTW  240
ANPKYAGKVI GNGLVFDVNS LYPSVMYDKP LPYGLPVPFS GEYEYDETHP LFIQHIKCGF  300
ELKDGHIPTI QIKKNFRFAD NEYLHSSEGN ILDLHVTNVD LALIKEHYTL YEEEYLQGYK  360
FKQVTGLFKN YIDYWSDKKI NAEDPAIRQM AKLMLNSLYG KFGTSIDVTG KEVFLKEDGS  420
TGFRKGQKEE RDPVYMPMGA FITAYARDVT IRTAQKCYDR ILYCDTDSIH LVGTEIPEAI  480
KDRIHDKKLG YWAHESTFWR AKFIRQKTYI EDLCMRFEGE KVNGEWKFKM VEEKDITKAT  540
ARELSVKCAG MPAQVKQYVT FDNFGVDFKH DPNDYTDEEI KRKNIKFKLK PTHRKGGQVL  600
VPTPFTIK                                                          608

SEQ ID NO: 29           moltype = AA  length = 573
FEATURE                 Location/Qualifiers
source                  1..573
                        mol_type = protein
```

```
                       note = Enterococcus faecium HP.1
                       organism = Enterococcus faecium
SEQUENCE: 29
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYA TTKSGKTKKE  120
KVRTIIYDSL KKYPFPVKQI AEAFNFPIKK GEIDYTKERP IGYKPTKDEW EYLKNDIQIM  180
AMALKIQFDQ GLTRMTRGSD ALGDYQDWVK TTYGKSRFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFEHYDILE  360
IHYTYGYMFK ASCDMFKGWI DKWIEVKNTT EGARKANAKG MLNSLYGKFG TNPDITGKVP  420
YMGEDGIVRL TLGEEELRDP VYVPLASFVT AWGRYTTITT AQKCFDRIIY CDTDSIHLVG  480
TEVPEAIDHL VDPKKLGYWG HESTFQRAKF IRQKTYVEEI DGELNVKCAG MPDRIKELVT  540
FDNFEVGFSS YGKLLPKRTQ GGVVLVDTMF TIK                              573

SEQ ID NO: 30          moltype = AA  length = 573
FEATURE                Location/Qualifiers
source                 1..573
                       mol_type = protein
                       note = Enterococcus faecium HP.2
                       organism = Enterococcus faecium
SEQUENCE: 30
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYT TTKSGKTKKE  120
KSRTIIYDSL KKYPFPVKQI AEAFNFPIKK GEIDYTKERP IGYKPTKDEW EYLKNDIQIM  180
AMALKIQFDQ GLTRMTRGSD ALGDYQDWVK TTYGKSRFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFEHYDILE  360
IHYTYGYMFK ASCDMFKGWI DKWIEVKNTT EGARKANAKG MLNSLYGKFG TNPDITGKVP  420
YMGEDGIVRL TLGEEELRDP VYVPLASFVT AWGRYTTITT AQKCFDRIIY CDTDSIHLVG  480
TEVPEAIDHL VDPKKLGYWG HESTFQRAKF IRQKTYVEEI DGELNVKCAG MPDRIKELVT  540
FDNFEVGFSS YGKLLPKRTQ GGVVLVDTMF TIK                              573

SEQ ID NO: 31          moltype = AA  length = 574
FEATURE                Location/Qualifiers
source                 1..574
                       mol_type = protein
                       note = Enterococcus faecium HP.3
                       organism = Enterococcus faecium
SEQUENCE: 31
MMIKKYTGDF ETTTDLNDCR VWSWGVCDID NVDNITFGLE IDSFFEWCKM QGSTDIYFHN  60
EKFDGEFMLS WLFKNGFKWC KEAKEDRTFS TLISNMGQWY ALEICWEVNY TTTKSGKTKK  120
EKSRTIIYDS LKKYPFPVKQ IAEAFNFPIK KGEIDYTKER PIGYKPTKDE WEYLKNDIQI  180
MAMALKIQFD QGLTRMTRGS DALGDYKDWL KATHGKTTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT SEGARKANAK GMLNSLYGKF GTNPDITGKV  420
PYMGEDGIVR LTLGEEELRD PVYVPLASFV TAWGRYTTIT TAQKCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                             574

SEQ ID NO: 32          moltype = AA  length = 574
FEATURE                Location/Qualifiers
source                 1..574
                       mol_type = protein
                       note = Enterococcus faecium HP.4
                       organism = Enterococcus faecium
SEQUENCE: 32
MMIKKYTGDF ETTTDLNDCR VWSWGVCDID NVDNITFGLE IDSFFEWCKM QGSTDIYFHN  60
EKFDGEFMLS WLFKNGFKWC KEAKEDRTFS TLISNMGQWY ALEICWEVNY TTTKSGKTKK  120
EKSRTIIYDS LKKYPFPVKQ IAEAFNFPIK KGEIDYTKER PIGYKPTKDE WEYLKNDIQI  180
MAMALKIQFD QGLTRMTRGS DALGDYQDWV KTTYGKSRFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT SEGARKANAK GMLNSLYGKF GTNPDITGKV  420
PYMGEDGIVR LTLGEEELRD PVYVPLASFV TAWGRYTTIT TAQKCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                             574

SEQ ID NO: 33          moltype = AA  length = 574
FEATURE                Location/Qualifiers
source                 1..574
                       mol_type = protein
                       note = Enterococcus faecium HP.5
                       organism = Enterococcus faecium
SEQUENCE: 33
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMGQWY ALEICWEVNY TTTKSGKTKK  120
EKSRTIIYDS LKKYPFPVKQ IAEAFNFPIK KGEIDYTKER PIGYKPTKDE WEYLKNDIQI  180
MAMALKIQFD QGLTRMTRGS DALGDYQDWV KTTYGKSRFK QWFPILSLGF DKDLRKAYKG  240
```

```
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQKCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                            574

SEQ ID NO: 34           moltype = AA  length = 573
FEATURE                 Location/Qualifiers
source                  1..573
                        mol_type = protein
                        note = Enterococcus faecium HP.6
                        organism = Enterococcus faecium
SEQUENCE: 34
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYA TTKSGKTKKE  120
KVRTIIYDSL KKYPFPVKQI AEAFNFPIKK GEIDYTKERP VGYNPTDDEW DYLKNDIQIM  180
AMALKIQFDQ GLTRMTRGSD ALGDYKDWLK ATHGKSTFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFEHYDILE  360
IHYTYGYMFK ASCDMFKGWI DKWIEVKNTT EGARKANAKG MLNSLYGKFG TNPDITGKVP  420
YMGEDGIVRL TLGEEELRDP VYVPLASFVT AWGRYTTITT AQRCFDRIIY CDTDSIHLVG  480
TDVPEAIEHL VDPKKLGYWG HESTFQRAKF IRQKTYVEEI DGELNVKCAG MPDRIKELVT  540
FDNFEVGFSS YGKLLPKRTQ GGVVLVDTMF TIK                             573

SEQ ID NO: 35           moltype = AA  length = 573
FEATURE                 Location/Qualifiers
source                  1..573
                        mol_type = protein
                        note = Enterococcus faecium HP.7
                        organism = Enterococcus faecium
SEQUENCE: 35
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYA TTKSGKTKKE  120
KVRTIIYDSL KKYPFPVKQI AEAFNFPIKK GEIDYTKERP VGYNPTDDEW DYLKNDIQIM  180
AMALKIQFDQ GLTRMTRGSD ALGDYKDWLK ATHGKSTFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFEHYDILE  360
IHYTYGYMFK ASCDMFKGWI DKWIEVKNTT EGARKANAKG MLNSLYGKFG TNPDITGKVP  420
YMGEDGIVRL TLGEEELRDP VYVPLASFVT AWGRYTTITT AQRCFDRIIY CDTDSIHLVG  480
TDAPEAIEHL VDPKKLGYWG HESTFQRAKF IRQKTYVEEI DGELNVKCAG MPDRIKELVT  540
FDNFEVGFSS YGKLLPKRTQ GGVVLVDTMF TIK                             573

SEQ ID NO: 36           moltype = AA  length = 573
FEATURE                 Location/Qualifiers
source                  1..573
                        mol_type = protein
                        note = Enterococcus faecium HP.8
                        organism = Enterococcus faecium
SEQUENCE: 36
MIKKYTGDFE TTTDLNDCRV WSWGVCDIDN VNNITFGLDI DSFFEWCEMQ GSTDIYFHNE  60
KFDGEFMLSW LFKNGFKWSK ETKEERTFST LISNMGQWYA LEICWEVNYT TTKSGKTKKE  120
KVRTIIYDSL KKYPFPVKQI AEAFNFPIKK GEIDYTKERP VGYNPTDDEW DYLKNDIQIM  180
AMALKIQFDQ GLTRMTRGSD ALGDYKDWLK ATHGKSTFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFDHYDILE  360
IHYTYGYMFK ASCDMFKGWI DKWIEVKNTT EGARKANAKG MLNSLYGKFG TNPDITGKVP  420
YMGEDGIVRL TLGEEELRDP VYVPLASFVT AWGRYTTITT AQRCFDRIIY CDTDSIHLVG  480
TEVPEAIDHL VDPKKLGYWG HESTFQRAKF IRQKTYVEEI DGELNVKCAG MPDRIKELVT  540
FDNFEVGFSS YGKLLPKRTQ GGVVLVDTMF TIK                             573

SEQ ID NO: 37           moltype = AA  length = 573
FEATURE                 Location/Qualifiers
source                  1..573
                        mol_type = protein
                        note = Enterococcus faecium HP.9
                        organism = Enterococcus faecium
SEQUENCE: 37
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYT TTKSGKTKKE  120
KVRTIIYDSL KKYPFPVKQI AEAFNFPIKK GEIDYTKERP VGYNPTDDEW DYLKNDIQIM  180
AMALKIQFDQ GLTRMTRGSD ALGDYKDWLK ATHGKSTFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFEHYDILE  360
IHYTYGYMFK ASCDMFKGWI DKWIEVKNTT EGARKANAKG MLNSLYGKFG TNPDITGKVP  420
YMGEDGIVRL TLGEEELRDP VYVPLASFVT AWGRYTTITT AQRCFDRIIY CDTDSIHLVG  480
TDVPEAIEHL VDPKKLGYWG HESTFQRAKF IRQKTYVEEI DGELNVKCAG MPDRIKELVT  540
FDNFEVGFSS YGKLLPKRTQ GGVVLVDTMF TIK                             573
```

-continued

```
SEQ ID NO: 38          moltype = AA  length = 574
FEATURE                Location/Qualifiers
source                 1..574
                       mol_type = protein
                       note = Enterococcus faecium HP.10
                       organism = Enterococcus faecium
SEQUENCE: 38
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYT TTTKSGKMKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFDHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 39          moltype = AA  length = 574
FEATURE                Location/Qualifiers
source                 1..574
                       mol_type = protein
                       note = Enterococcus faecium HP.11
                       organism = Enterococcus faecium
SEQUENCE: 39
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMGQWY ALEICWEVNY ATTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTDVPEAIEH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 40          moltype = AA  length = 574
FEATURE                Location/Qualifiers
source                 1..574
                       mol_type = protein
                       note = Enterococcus faecium HP.12
                       organism = Enterococcus faecium
SEQUENCE: 40
MMIKKYTGDF ETTTDLNDCR VWSWGVCDID NVDNITFGLE IDSFFEWCKM QGSTDIYFHN  60
EKFDGEFMLS WLFKNGFKWS KEAKEDRTFS TLISNMGQWY ALEICWEVNY TTTKSGKTKK  120
DKVRTIIYDS LKKYPFPVKQ IAEAFDFPIK KGEIDYNKER PIGYNPTDDE WEYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQKCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 41          moltype = AA  length = 574
FEATURE                Location/Qualifiers
source                 1..574
                       mol_type = protein
                       note = Enterococcus faecium HP.13
                       organism = Enterococcus faecium
SEQUENCE: 41
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMGQWY ALEICWNIKY TTTKSGKTKK  120
EKVRTIIYDS LKKYPFPVKQ IAEAFNFSIK KGEIDYTKER PVGYNPTDDE WDYLKNDIQI  180
MAMALKIQFD QGLTRMTRGS DALGDYKDWL KATHGKSTFK QWFPVLSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLES SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLT  480
GTEVPETIEH LVDSKKLGYW KHESTFQRAK FIRQKTYVEE IDGELNVKCA GMPDRIKELV  540
TFDNFEVGFS SYGKLLPKRT QGGVVLVDTM FTIK                              574

SEQ ID NO: 42          moltype = AA  length = 574
FEATURE                Location/Qualifiers
source                 1..574
                       mol_type = protein
                       note = Enterococcus faecium HP.14
                       organism = Enterococcus faecium
SEQUENCE: 42
```

-continued

```
MMIKKYTGDF ETTTDLNDCR VWSWGVCDID NVNNITFGLD IDSFFEWCEM QGSTDIYFHN  60
EKFDGEFMLS WLFKNGFKWS KETKEERTFS TLISNMGQWY ALEICWEVNY TTTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFDHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 43           moltype = AA  length = 574
FEATURE                 Location/Qualifiers
source                  1..574
                        mol_type = protein
                        note = Enterococcus faecium HP.15
                        organism = Enterococcus faecium
SEQUENCE: 43
MMIKKYTGDF ETTTDLNDCR VWSWGVCDID NVDNITFGLE IDSFFEWCKM QGSTDIYFHN  60
EKFDGEFMLS WLFKNGFKWC KEAKEDRTFS TLISNMGQWY ALEICWEVNY TTTKSGKTKK  120
EKSRTIIYDS LKKYPFPVKQ IAEAFNFPIK KGEIDYTKER PIGYKPTKDE WEYLKNDIQI  180
MAMALKIQFD QGLTRMTRGS DALGDYKDWL KATHGKTTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQKCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 44           moltype = AA  length = 574
FEATURE                 Location/Qualifiers
source                  1..574
                        mol_type = protein
                        note = Enterococcus faecium HP. 16
                        organism = Enterococcus faecium
SEQUENCE: 44
MMIKKYTGDF ETTTDLNDCR VWSWGVCDID NVDNITFGLE IDSFFEWCKM QGSTDIYFHN  60
EKFDGEFMLS WLFKNGFKWC KEAKEDRTFS TLISNMGQWY ALEICWEVNY TTTKSGKTKK  120
EKSRTIIYDS LKKYPFPVKQ IAEAFNFPIK KGEIDYTKER PIGYKPTKDE WEYLKNDIQI  180
MAMALKIQFD QGLTRMTRGS DALGDYQDWV KTTYGKSRFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQKCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 45           moltype = AA  length = 574
FEATURE                 Location/Qualifiers
source                  1..574
                        mol_type = protein
                        note = Enterococcus faecium HP.17
                        organism = Enterococcus faecium
SEQUENCE: 45
MMIKKYTGDF ETTTDLNDCR VWSWGVCDID NFDNITFGLD IDSFFEWCEM QGSTDIYFHN  60
EKFDGEFMLS WLFKNGFKWS KETKEERTFS TLISNMGQWY ALEICWEVNY TTTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFDHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTEVPEAIDH LVDPKKLGYW GHESTFQRAK FIRQKTYVEE IDGELNVKCA GMPDRIKELV  540
TFDNFEVGFS SYGKLLPKRT QGGVVLVDTM FTIK                              574

SEQ ID NO: 46           moltype = AA  length = 573
FEATURE                 Location/Qualifiers
source                  1..573
                        mol_type = protein
                        note = Enterococcus faecium HP.18
                        organism = Enterococcus faecium
SEQUENCE: 46
MIKKYTGDFE TTTDLNDCRV WSWGVCDIDN VDNITFGLDI DSFFEWCEMQ GSTDIYFHNE  60
KFDGEFMLSW LFKNGFKWSK ETKEERTFST LISNMGQWYA LEICWEVNYA TTKSGKTKKE  120
KVRTIIYDSL KKYPFPVKQI AEAFNFPIKK GEIDYTKERP VGYNPTDDEW EYLKNDIQIM  180
AMALKIQFDQ GLTRMTRGSD ALGDYKDWLK ATHGKSTFKQ WFPILSLGFD KDLRKAYKGG  240
FTWVNKVFQG KEIGDGIVFD VNSLYPSQMH VRPLPYGTPL FYEGEYKPNN DYPLYIQNIK  300
VRFRLKEGYI PTIQVKQSSL FIQNEYLDSS VNKLGVDELI DLTLTNVDLE LFFEHYDILE  360
IHYTYGYMFK ASCDMFKGWI DKWIEVKNTT EGARKANAKG MLNSLYGKFG TNPDITGKVP  420
```

-continued

```
YMGEDGIVRL TLGEEELRDP VYVPLASFVT AWGRYTTITT AQRCFDRIIY CDTDSIHLVG  480
TDVPEAIEHL VDPKKLGYWG HESTFQRAKF IRQKTYVEEI DGELNVKCAG MPDRIKELVT  540
FDNFEVGFSS YGKLLPKRTQ GGVVLVDTMF TIK                                573

SEQ ID NO: 47          moltype = AA  length = 573
FEATURE                Location/Qualifiers
source                 1..573
                       mol_type = protein
                       note = Enterococcus faecium HP. 19
                       organism = Enterococcus faecium
SEQUENCE: 47
MIKKYTGDFE TTTDLNDCRV WSWGVCDIDN VDNITFGLDI DSFFEWCEMQ GSTDIYFHNE  60
KFDGEFMVSW LFKNGFKWSK ETKEERTFST LISNMGQWYA LEICWEVNYT TTKSGKTKKE  120
KVRTIIYDSL KKYPFPVKQI AEAFNFPIKK GEIDYTKERP VGYNPTDDEW DYLKNDIQIM  180
AMALKIQFDQ GLTRMTRGSD ALGDYKDWLK ATHGKLTFKQ WFPILSLGFD KDLRKAYKGG  240
FTWVNKVFQG KEIGDGIVFD VNSLYPSQMY VRPLPYGTPL FYEGEYKPNN DYPLYIQNIK  300
VRFRLKEGYI PTIQVKQSSL FIQNEYLDSS VNKLGVDELI DLTLTNVDLE LFFAHYDILE  360
IHYTYGYMFK ASCGMFKGWI DKWIEVKNTT EGARKANAKG MLNSLYGKFG TNPDITGKVP  420
YMGEDGIVRL TLGEEELRDP VYVPLASFVT AWGRYTTVTT AQRCFDRIIY CDTDSIHLVG  480
TDVPEAIEHL VDPKKLGYWG HESTFQRAKF IRQKTYVEEI DGELNVKCAG MPDRIKELVT  540
FDNFEVGFSS YGKLLPKRTQ GGVVLVDTMF TIK                                573

SEQ ID NO: 48          moltype = AA  length = 574
FEATURE                Location/Qualifiers
source                 1..574
                       mol_type = protein
                       note = Enterococcus faecium HP.20
                       organism = Enterococcus faecium
SEQUENCE: 48
MMIKKYTGDF ETTTDLNDCR VWSWGVCDID NVDNITFGLE IDSFFEWCKM QGSTDIYFHN  60
EKFDGEFMLS WLFKNGFKWC KEAKEDRTFS TLISNMGQWY ALEICWEVNY ATTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTDVPEAIEH LVDPKKLGYW GHESTFQRAK FIRQKTYVEE IDGELNVKCA GMPDRIKELV  540
TFDNFEVGFS SYGKLLPKRT QGGVVLVDTM FTIK                               574

SEQ ID NO: 49          moltype = AA  length = 574
FEATURE                Location/Qualifiers
source                 1..574
                       mol_type = protein
                       note = Enterococcus faecium HP. 21
                       organism = Enterococcus faecium
SEQUENCE: 49
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMGQWY ALEICWEVNY ATTKSGKTKK  120
EKVRTIIYDS LKKYPFPVKQ IAEAFNFPIK KGEIDYTKER PVGYNPTDDE WEYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM HVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTDVPEAIEH LVDPKKLGYW GHESTFQRAK FIRQKTYVEE IDGELNVKCA GMPDRIKELV  540
TFDNFEVGFS SYGKLLPKRT QGGVVLVDTM FTIK                               574

SEQ ID NO: 50          moltype = AA  length = 574
FEATURE                Location/Qualifiers
source                 1..574
                       mol_type = protein
                       note = Enterococcus faecium HP.22
                       organism = Enterococcus faecium
SEQUENCE: 50
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMGQWY ALEICWEVNY ATTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNSDITGKV  420
PYMGEDGIVR LTLGEEELRD PVYVPLASFV TAWGRYTTIT TAQRCFDRII YCDTDSIHLV  480
GTDVPEAIEH LVDPKKLGYW GHESTFQRAK FIRQKTYVEE IDGELNVKCA GMPDRIKELV  540
TFDNFEVGFS SYGKLLPKRT QGGVVLVDTM FTIK                               574

SEQ ID NO: 51          moltype = AA  length = 574
FEATURE                Location/Qualifiers
source                 1..574
```

-continued

```
                        mol_type = protein
                        note = Enterococcus faecium HP.23
                        organism = Enterococcus faecium
SEQUENCE: 51
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMDQWY ALEICWEVNY ATTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLDS SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTDVPEAIEH LVDPKKLGYW GHESTFQRAK FIRQKTYVEE IDGELNVKCA GMPDRIKELV  540
TFDNFEVGFS SYGKLLPKRT QGGVVLVDTM FTIK                            574

SEQ ID NO: 52           moltype = AA  length = 574
FEATURE                 Location/Qualifiers
source                  1..574
                        mol_type = protein
                        note = Enterococcus faecium HP.24
                        organism = Enterococcus faecium
SEQUENCE: 52
MMIKKYTGDF ETTTDLNDCR VWSWGVCDID NVDNITFGLD IDSFFEWCEM QGSTDIYFHN  60
EKFDGEFMLS WLFKNGFKWS KETKEERTFS TLISNMGQWY ALEICWNINY TTTKSGKTKK  120
EKVRTIIYDS LKKYPFPVKQ IAEAFNFPIK KGEIDYTKER PVGYNPTDDE WDYLKNDIQI  180
MAMALKIQFD QGLTRMTRGS DALGDYKDWL KATHGKSTFK QWFPILSLGF DKDLRKAYKG  240
GFTWVNKVFQ GKEIGDGIVF DVNSLYPSQM YVRPLPYGTP LFYEGEYKPN NDYPLYIQNI  300
KVRFRLKEGY IPTIQVKQSS LFIQNEYLES SVNKLGVDEL IDLTLTNVDL ELFFEHYDIL  360
EIHYTYGYMF KASCDMFKGW IDKWIEVKNT TEGARKANAK GMLNSLYGKF GTNPDITGKV  420
PYMGEDGIVR LTLGEEELRD PVYVPLASFV TAWGRYTTIT TAQRCFDRII YCDTDSIHLV  480
GTDVPEAIEH LVDPKKLGYW GHESTFQRAK FIRQKTYVEE IDGELNVKCA GMPDRIKELV  540
TFDNFEVGFS SYGKLLPKRT QGGVVLVDTM FTIK                            574

SEQ ID NO: 53           moltype = DNA  length = 39
FEATURE                 Location/Qualifiers
source                  1..39
                        mol_type = other DNA
                        organism = synthetic construct
modified_base           38^39
                        mod_base = OTHER
                        note = phosphorothioate bond
SEQUENCE: 53
ctttaagaag gagatataca gaattcatga aacatatgc                       39

SEQ ID NO: 54           moltype = DNA  length = 21
FEATURE                 Location/Qualifiers
source                  1..21
                        mol_type = other DNA
                        organism = synthetic construct
modified_base           20^21
                        mod_base = OTHER
                        note = phosphorothioate bond
SEQUENCE: 54
gttagcagcc ggatctcagt g                                          21
```

MODIFIED PH129 POLYMERASE AND USES THEREOF

CROSS-REFERENCES TO RELATED APPLICATIONS

This application is a continuation of U.S. Utility application Ser. No. 18/659,585, filed May 9, 2024, which is a continuation of the International PCT Application PCT/US2023/075838, filed Oct. 3, 2023, which claims the benefit of U.S. Provisional Application No. 63/378,223, filed Oct. 3, 2022; U.S. Provisional Application No. 63/493,180, filed Mar. 30, 2023; U.S. Provisional Application No. 63/502,005, filed May 12, 2023; and U.S. Provisional Application No. 63/580,874, filed Sep. 6, 2023, each of which are incorporated herein by reference in their entirety and for all purposes.

SEQUENCE LISTING

The Sequence Listing written in file 051385-587C02US_seglisting.xml, created Oct. 5, 2023, 87,283 bytes, machine format IBM-PC, MS Windows operating system, is hereby incorporated by reference.

BACKGROUND

DNA polymerases replicate the genomes of living organisms. DNA polymerases add nucleotide triphosphate (dNTP) residues to the 3'-end of the growing DNA chain, using a complementary DNA as template. One such DNA polymerase, Phi29 DNA polymerase, is a monomeric enzyme of 66 kDa, and is the replicative polymerase from the *Bacillus subtilis* phage phi29 belonging to the eukaryotic-type family of DNA polymerases (family B). Referred to as proofreading, phi29 contains an exonuclease domain that catalyzes 3'→5' exonucleolysis of mismatched nucleotides preferentially on single-stranded DNA or RNA, thereby enhancing replication fidelity at least 100-fold. Additionally, wild-type phi29 DNA polymerase reliably binds to single stranded DNA, and performs DNA synthesis without processivity cofactors, accounting for the highest known processivity (>70 kb) among other DNA polymerases. Strong processivity, robust strand displacement activity, and high accuracy allow the enzyme to amplify whole genomes with minimal amplification bias compared to PCR based amplification methods. Therefore, it has been widely used for rapidly amplifying targets (e.g., multiple displacement amplification (MDA) or rolling cycle amplification (RCA)), and enabling point-of-care analyses and immunoassays. Efforts to improve the processivity and strand displacing activity of phi29, without sacrificing the accuracy or stability of phi29 enzymes remains a challenge. Disclosed herein, inter alia, are solutions to these and other problems in the art.

BRIEF SUMMARY

In an aspect is provided a polymerase including an amino acid sequence that is at least 80% identical to SEQ ID NO: 1; including a proline, tryptophan, phenylalanine, tyrosine, alanine, or glycine at an amino acid position corresponding to position 216 of SEQ ID NO:1.

In an aspect is provided a polymerase including one or more amino acid substitutions as described herein. In embodiments, the polymerase includes an amino acid sequence that is at least 50% identical to SEQ ID NO:1; and includes an amino acid substitution, wherein the amino acid substitution is: a proline, tryptophan, phenylalanine, tyrosine, alanine, or glycine an amino acid position corresponding to position 216 of SEQ ID NO:1; an arginine, lysine, asparagine, glutamine, alanine, or glycine at an amino acid position corresponding to position 417 of SEQ ID NO:1; a valine, lysine, asparagine, glutamine, alanine, or glycine at an amino acid position corresponding to position 394 of SEQ ID NO:1; and/or an asparagine, glutamine, alanine, or glycine at an amino acid position corresponding to position 93 of SEQ ID NO:1.

In another aspect is provided a polymerase including an amino acid sequence that is at least 85% identical to SEQ ID NO: 1; including a serine, threonine, tyrosine, alanine, or glycine at an amino acid position corresponding to position 87 of SEQ ID NO:1; an asparagine, glutamine, alanine, or glycine at an amino acid position corresponding to position 93 of SEQ ID NO:1; a valine, leucine, alanine, or glycine at an amino acid position corresponding to position 378 of SEQ ID NO:1; a glutamic acid, aspartic acid, alanine, glycine, or threonine at an amino acid position corresponding to position 536 of SEQ ID NO:1; and a glycine, alanine, valine, serine, or threonine at an amino acid position corresponding to position 578 of SEQ ID NO:1. In embodiments, the polymerase includes an arginine, histidine, asparagine, glutamine, alanine, or glycine at an amino acid position corresponding to position 366 of SEQ ID NO:1.

In another aspect is provided a polymerase including an amino acid sequence that is at least 50% identical to SEQ ID NO: 1; including one or more of the following amino acid substitutions: A324T, A394G, A394K, A394N, A394Q, A394V, A444I, D219N, D34A, D34E, D34N, D34Q, E239A, E239V, E486V, F198L, F47I, G401A, G401L, G401V, G417A, G417K, G417N, G417Q, G417R, G579A, G579S, G579T, G579Y, H485L, I119A, I119G, I119L, I119V, I179F, I378A, I378G, I378L, I378V, I93A, I93G, I93N, I93Q, K131E, K132A, K132D, K132E, K132G, K132T, K135A, K135D, K135E, K135G, K311N, K311Q, K311R, K366A, K366G, K366H, K366N, K366Q, K366R, K536A, K536D, K536E, K536G, K536T, K539E, L216A, L216F, L216G, L216P, L216W, L216Y, L381Q, L462A, L462G, L462I, L462L, L462V, L567M, P87A, P87G, P87S, P87T, P87Y, R552A, R552N, R552Q, S192A, S192C, S192G, S260N, S260Q, S487C, S578A, S578G, S578I, S578L, S578T, S578V, T203S, T231A, T231I, T231V, T434A, T434G, T434Y, V565A, V565G, V565M, W436R, Y343C, Y500A, Y500F, or Y500G.

In another aspect is provided a polymerase including an amino acid sequence that is at least 50% identical to SEQ ID NO: 1; including one or more of the following amino acid substitutions: A83T, A83V, A324T, A394G, A394K, A394N, A394Q, A394V, A444I, D219N, D34A, D34E, D34N, D34Q, D121N, E239A, E239V, E486V, F198L, F47I, G155D, G155C, G184C, G401A, G401L, G401V, G417A, G417K, G417N, G417Q, G417R, G579A, G579S, G579T, G579Y, H485L, I40V, I119A, I119G, I119L, I119V, I179F, I378A, I378G, I378L, I378V, I93A, I93G, I93N, I93Q, K125R, K131A, K131D, K131E, K131G, K131T, K132A, K132D, K132E, K132G, K132T, K135A, K135D, K135E, K135G, K311N, K311Q, K311R, K366A, K366G, K366H, K366N, K366Q, K366R, K536A, K536D, K536E, K536G, K536T, K539A, K539D, K539E, K539G, K539T, L156P, L156H, L216A, L216F, L216G, L216P, L216W, L216Y, L381Q, L462A, L462G, L462I, L462L, L462V, L567M, P87A, P87G, P87S, P87T, P87Y, P264A, P424S, R552A, R552N, R552Q, S192A, S192C, S192G, S260N, S260Q, S487C, S578A, S578G, S578I, S578L, S578T, S578V, T15A, T15K, T15P, T203S, T231A, T231I, T231V, T434A, T434G, T434Y, V565A, V565G, V565M, W50P, W50R, W436R, Y120H, Y184A, Y343C, Y500A, Y500F, and/or Y500G.

In an aspect is provided a method of incorporating a nucleotide into a primed nucleic acid template (e.g., a primer hybridized to a template nucleic acid). In embodiments, the method includes combining in a reaction vessel: (i) a primer hybridized to a nucleic acid template, (ii) a nucleotide solution including a plurality of nucleotides, and (iii) a polymerase, wherein the polymerase is a polymerase as described herein.

In an aspect is provided a method of amplifying a template polynucleotide, the method including: contacting a template polynucleotide with an amplification primer, and amplifying the template polynucleotide by extending an amplification primer with a polymerase to generate an extension product including one or more complements of the template polynucleotide; wherein the polymerase is a polymerase as described herein.

BRIEF DESCRIPTION OF THE DRAWINGS

FIG. 2A illustrates the amino acid position and the corresponding structure domain for the wild type enzyme. Structural analysis of phi 29 DNA polymerase portrays the enzyme as analogous to a human right hand, with three domains: a 'fingers' domain that interacts with the incoming dNTP and paired template base, and that closes at each nucleotide addition step; a 'palm' domain that catalyzes the phosphoryl-transfer reaction; and a 'thumb' domain that interacts with duplex DNA. phi29 DNA polymerase also includes two additional subdomains, called TPR1 and TPR2, that are insertions between the fingers and palm subdomains. TPR2 helps to form a narrow tunnel around the downstream DNA, forcing separation of the second strand before its entry into polymerase active site. Additionally, the palm, thumb, TPR1, and TPR2 form a doughnut-shaped structure around the upstream duplex product, providing maximal DNA-binding stability which enhances processivity in a manner analogous to sliding-clamp proteins. To reduce dimensional complexity, the amino acid position is shown below the corresponding domain. For example, the TPR1 subdomain is comprised of the amino acid positions 261-359. In addition to these domains, the phi29 DNA polymerase also includes an exonuclease (also referred herein as "exo") domain capable of catalyzing 3'→5' exonucleolysis of mismatched nucleotides. FIG. 2B provides a molecular visualization of the protein structure of the phi29 DNA polymerase. The exo tunnel and selected basic (i.e., positively charged) residues from the exo domain (e.g., K131, K132, and K135) and thumb domain (e.g., K536, K538, and K539) are shown. It was determined that positively charged residues, K135 in the exonuclease domain, and K536 in the thumb domain, are about 12 Å to 18A away from the "active center" (i.e., the nucleotide incorporation site) and are possibly involved in non-specific binding of DNA oligonucleotides by supporting the negatively charged phosphate backbone of the DNA.

FIG. 3 provides an alignment of seven sequences described herein. A portion of the entire amino acid sequence is shown, aligning the wild type polymerase (SEQ ID NO:1) to BSTP6 (SEQ ID NO:12), MinWT (SEQ ID NO:2), BSTP4 (SEQ ID NO:8), Whiting18 (SEQ ID NO:17), Phage M2 (SEQ ID NO:20), and Beecentumtrevirus (SEQ ID NO:22). The alignment highlights a negative three (−3) frameshift in amino acid positions of MinWT, BSTP4, Whiting18, Phage M2, and Beecentumtrevirus relative to wild type, wherein the amino acid positions are shifted by three positions. For example, the amino acid position 312 of the wild type sequence corresponds to the amino acid position 309 if BSTP4 (SEQ ID NO:8). Amino acid substitutions relative to the wild type sequence are shaded. Marking of these amino acids makes clear that their homologous position in related proteins is readily identified, both for the proteins aligned herein and for other proteins readily identified by one of skill in the art using standard sequence search capabilities such as a BLAST search, available at the NCBI website affiliated with the National Institutes of Health and the National Library of Medicine (ncbi.nlm.nih.gov).

DETAILED DESCRIPTION

Figure 1:
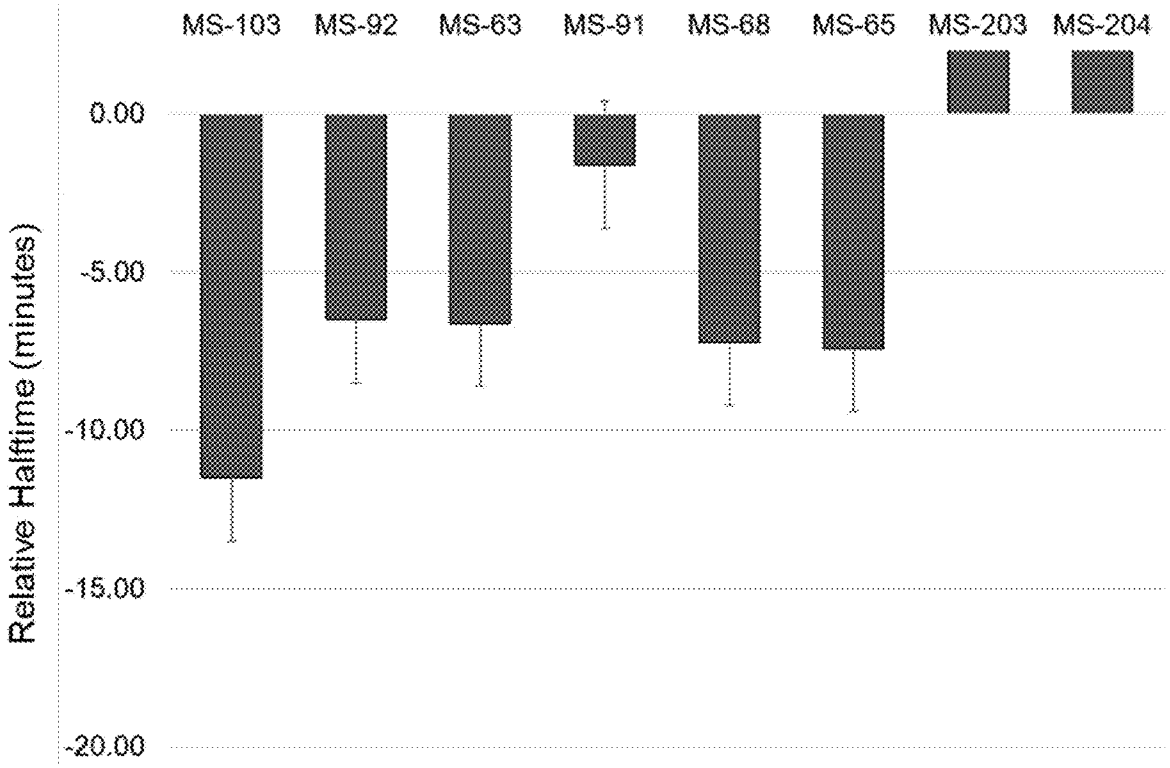
FIG. 1. The relative average halftime for some of the variants tested in the eRCA assay. Any improvement in kinetics (i.e., faster processivity) of the variant relative to the wild type is measured as a negative value, whereas slower incorporation is provided as a positive value.

The aspects and embodiments described herein relate to polymerases. For example, provided herein are compositions and methods of polynucleotide extension using a polymerase mutant described herein, wherein in embodiments, the polymerase exhibits an increased rate for incorporation of nucleotides relative to the wild-type sequence.

I. Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms “a”, “an”, and “the” include the plural reference unless the context clearly indicates otherwise. Reference throughout this specification to, for example, “one embodiment”, “an embodiment”, “another embodiment”, “a particular embodiment”, “a related embodiment”, “a certain embodiment”, “an additional embodiment”, or “a further embodiment” or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

As used herein, the term “about” means a range of values including the specified value, which a person of ordinary skill in the art would consider reasonably similar to the specified value. In embodiments, the term “about” means within a standard deviation using measurements generally acceptable in the art. In embodiments, about means a range extending to +/−10% of the specified value. In embodiments, about means the specified value.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

“Nucleic acid” refers to nucleotides (e.g., deoxyribonucleotides or ribonucleotides) and polymers thereof in either single-, double- or multiple-stranded form, or complements thereof. The terms “polynucleotide,” “oligonucleotide,” “oligo” or the like refer, in the usual and customary sense, to a sequence of nucleotides. The term “nucleotide” refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms “nucleic acid oligomer” and “oligonucleotide” are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms “polynucleotide,” “oligonucleotide,” “oligo” or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

The term “duplex” in the context of polynucleotides refers, in the usual and customary sense, to double-strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. Different polynucleotides may have different three-dimensional structures, and may perform various functions, known or unknown. Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term “base” and “nucleobase” as used herein refers to a purine or pyrimidine compound, or a derivative thereof, that may be a constituent of nucleic acid (i.e. DNA or RNA, or a derivative thereof). In embodiments, the base is a derivative of a naturally occurring DNA or RNA base (e.g., a base analogue). In embodiments, the base is a base-pairing base. In embodiments, the base pairs to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), guanosine or a derivative thereof (e.g., 7-methylguanosine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is thymine, cytosine, uracil, adenine, guanine, hypoxanthine, xanthine, theobromine, caffeine, uric acid, or isoguanine. In embodiments, the base is

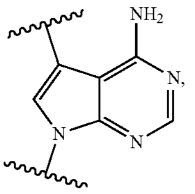

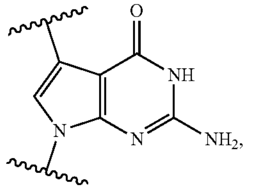

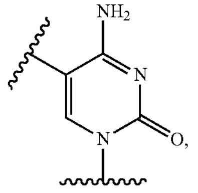

or

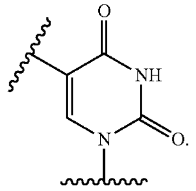

A polynucleotide is typically composed of a specific sequence of four nucleotide bases: adenine (A); cytosine (C); guanine (G); and thymine (T) (uracil (U) for thymine (T) when the polynucleotide is RNA. Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "isolated", when applied to a nucleic acid or protein, denotes that the nucleic acid or protein is essentially free of other cellular components with which it is associated in the natural state. It can be, for example, in a homogeneous state and may be in either a dry or an aqueous solution. Purity and homogeneity are typically determined using analytical chemistry techniques such as polyacrylamide gel electrophoresis or high performance liquid chromatography. A protein that is the predominant species present in a preparation is substantially purified.

The terms "analog" and "analogue" and "derivative" in reference to a chemical compound, refers to compounds having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: a Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

The term "complement," as used herein, refers to a nucleotide (e.g., RNA or DNA) or a sequence of nucleotides capable of base pairing with a complementary nucleotide or sequence of nucleotides. As described herein and commonly known in the art, the complementary (matching) nucleoside of adenosine is thymidine and the complementary (matching) nucleoside of guanosine is cytidine. Thus, a complement may include a sequence of nucleotides that base pair with corresponding complementary nucleotides of a second nucleic acid sequence. The nucleotides of a complement may match, partially or completely, the nucleotides of the second nucleic acid sequence. Where the nucleotides of the complement completely match each nucleotide of the second nucleic acid sequence, the complement forms base pairs with each nucleotide of the second nucleic acid sequence.

Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other may have a specified percentage of nucleotides that are complementary (i.e., about 60% identity, preferably 65%, 70%, 75%, 80%, 85%, 90%, 91%, 92%, 93%, 94%, 95%, 96%, 97%, 98%, 99%, or higher complementarity over a specified region).

"DNA" refers to deoxyribonucleic acid, a polymer of deoxyribonucleotides (e.g., dATP, dCTP, dGTP, dTTP, dUTP, etc.) linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof) and ssRNA can, if sufficiently complementary, hybridize to form double-stranded DNA/RNA complexes (or regions).

The term "DNA primer" or simply "primer" refers to any DNA molecule that may hybridize to a DNA template and be bound by a DNA polymerase and extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment, the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the term "primer binding sequence" refers to a polynucleotide sequence that is complementary to at least a portion of a primer (e.g., a sequencing primer or an amplification primer). Primer binding sequences can be of any suitable length. In embodiments, a primer binding sequence is about or at least about 10, 15, 20, 25, 30, or more nucleotides in length. In embodiments, a primer binding sequence is 10-50, 15-30, or 20-25 nucleotides in length. The primer binding sequence may be selected such that the primer (e.g., sequencing primer) has the preferred characteristics to minimize secondary structure formation or minimize non-specific amplification, for example having a length of about 20-30 nucleotides; approximately 50% GC content, and a Tm of about 55° C. to about 65° C.

The term "DNA template" refers to any DNA molecule that may be bound by a DNA polymerase and utilized as a template for nucleic acid synthesis.

The term "dATP analogue" refers to an analogue of deoxyadenosine triphosphate (dATP) that is a substrate for a DNA polymerase. The term "dCTP analogue" refers to an analogue of deoxycytidine triphosphate (dCTP) that is a substrate for a DNA polymerase. The term "dGTP analogue" refers to an analogue of deoxyguanosine triphosphate (dGTP) that is a substrate for a DNA polymerase. The term "dNTP analogue" refers to an analogue of deoxynucleoside triphosphate (dNTP) that is a substrate for a DNA polymerase. The term "dTTP analogue" refers to an analogue of deoxythymidine triphosphate (dUTP) that is a substrate for a DNA polymerase. The term "dUTP analogue" refers to an analogue of deoxyuridine triphosphate (dUTP) that is a substrate for a DNA polymerase.

The term "extendible" means, in the context of a nucleotide, primer, or extension product, that the 3'-OH group of the molecule is available and accessible to a DNA polymerase for extension or addition of nucleotides derived from dNTPs or dNTP analogues. "Incorporation" means joining of the modified nucleotide to the free 3' hydroxyl group of a second nucleotide via formation of a phosphodiester linkage with the 5' phosphate group of the modified nucleotide. The second nucleotide to which the modified nucleotide is joined will typically occur at the 3' end of a polynucleotide chain.

The term "modified nucleotide" refers to nucleotide or nucleotide analogue modified in some manner. Typically, a nucleotide contains a single 5-carbon sugar moiety, a single nitrogenous base moiety and 1 to three phosphate moieties. In particular embodiments, a nucleotide can include a blocking moiety or a label moiety. A blocking moiety (e.g., a reversible terminator moiety) on a nucleotide prevents formation of a covalent bond between the 3' hydroxyl moiety of the nucleotide and the 5' phosphate of another nucleotide. A blocking moiety on a nucleotide can be reversible (i.e., a reversible terminator), whereby the blocking moiety can be removed or modified to allow the 3' hydroxyl to form a covalent bond with the 5' phosphate of another nucleotide.

A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both.

A "removable" group, e.g., a label or a blocking group or protecting group, refers to a chemical group that can be removed from a dNTP analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a dNTP of dNTP analogue.

"Reversible blocking groups" or "reversible terminators" include a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethy reversible terminator.

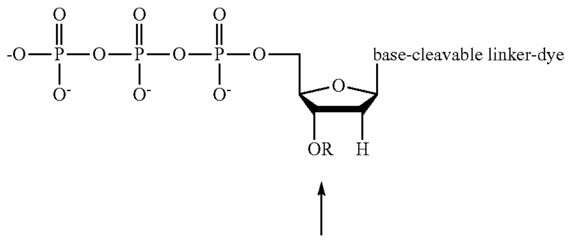

Reversible terminating group

3'-O-blocked reversible terminator

The term "non-covalent linker" is used in accordance with its ordinary meaning and refers to a divalent moiety which includes at least two molecules that are not covalently linked to each other but are capable of interacting with each other via a non-covalent bond (e.g. electrostatic interactions (e.g. ionic bond, hydrogen bond, halogen bond) or van der Waals interactions (e.g. dipole-dipole, dipole-induced dipole, London dispersion). In embodiments, the non-covalent linker is the result of two molecules that are not covalently linked to each other that interact with each other via a non-covalent bond.

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation).

The term "orthogonal detectable label" or "orthogonal detectable moiety" as used herein refer to a detectable label (e.g. fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox™-Labeled Tetrazine, Alexa Fluor® 488-Labeled SHA, Cy® 5-Labeled Streptavidin, and R6G-Labeled Dibenzocyclooctyne. ROX™ is a trademark of Applera Corporation. Alexa Fluor® is a trademark of Life Technologies Corporation. Cy® is a trademark of Cytiva.

A "detectable agent" or "detectable compound" or "detectable label" or "detectable moiety" is a composition detectable by spectroscopic, photochemical, biochemical, immunochemical, chemical, magnetic resonance imaging, or other physical means. For example, detectable agents include fluorophores (e.g. fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa Fluor® dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy®2 moiety, Cy® 3 moiety, Cy®5 moiety, Cy®7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable label is a fluorescent dye. In embodiments, the detectable label is a fluorescent dye capable of exchanging energy with another fluorescent dye (e.g., fluorescence resonance energy transfer (FRET) chromophores).

A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics, which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another: 1) Non-polar—Alanine (A), Leucine (L), Isoleucine (I), Valine (V), Glycine (G), Methionine (M); 2) Aliphatic—Alanine (A), Leucine (L), Isoleucine (I), Valine (V); 3) Acidic—Aspartic acid (D), Glutamic acid (E); 4) Polar—Asparagine (N), Glutamine (Q); Serine (S), Threonine (T); 5) Basic—Arginine (R), Lysine (K); 7) Aromatic—Phenylalanine (F), Tyrosine (Y), Tryptophan (W), Histidine (H); 8) Other—Cysteine (C) and Proline (P).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Percent identity often refers to the percentage of matching positions of two sequences for a contiguous section of positions, wherein the two sequences are aligned in such a way to maximize matching positions and minimize gaps of non-matching positions. In some embodiments, alignments are conducted wherein there are no gaps between the two sequences. In some instances, the alignment results in less than 5% gaps, less than 3% gaps, or less than 1% gaps. Additional methods of sequence comparison or alignment are also consistent with the disclosure.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithm with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. As used herein, percent (%) amino acid sequence identity is defined as the percentage of amino acids in a candidate sequence that is identical to the amino acids in a reference sequence, after aligning the sequences and introducing gaps, if necessary, to achieve the maximum percent sequence identity. Alignment for purposes of determining percent sequence identity can be achieved in various ways that are within the level of skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 700, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "position", "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. Similarly, the term "functionally equivalent to" in relation to an amino acid position refers to an amino acid residue in a protein that corresponds to a particular amino acid in a reference sequence. An amino acid "corresponds" to a given residue when it occupies the same essential structural position within the protein as the given residue. One skilled in the art will immediately recognize the identity and location of residues corresponding to a specific position in a protein (e.g., polymerase) in other proteins with different numbering systems. For example, by performing a simple sequence alignment with a protein (e.g., polymerase) the identity and location of residues corresponding to specific positions of said protein are identified in other protein sequences aligning to said protein. For example, a selected residue in a selected protein corresponds to methionine at position 129 when the selected residue occupies the same essential spatial or other structural relationship as a methionine at position 129. In some embodiments, where a selected protein is aligned for maximum homology with a protein, the position in the aligned selected protein aligning with methionine 129 is said to correspond to methionine 129. Instead of a primary sequence alignment, a three-dimensional structural alignment can also be used, e.g., where the structure of the selected protein is aligned for maximum correspondence with the methionine at position 129, and the overall structures compared. In this case, an amino acid that occupies the same essential position as methionine 129 in the structural model is said to correspond to the methionine 129 residue. Sequence alignments may be compiled using any of the standard alignment tools known in the art, such as for example BLAST and DIAMOND (Buchfink et al. Nat Methods 12, 59-60 (2015)), and the like.

The term "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand one nucleotide at a time.

The term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide, thereby releasing deoxyribonucleoside 5'-monophosphates one after another. One having skill in the art understands that an enzyme having 3'-5' exonuclease activity does not cleave DNA strands without terminal 3'-OH moieties. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

The terms "measure", "measuring", "measurement" and the like refer not only to quantitative measurement of a particular variable, but also to qualitative and semi-quantitative measurements. Accordingly, "measurement" also includes detection, meaning that merely detecting a change, without quantification, constitutes measurement.

A "polymerase-template complex" refers to a functional complex between a DNA polymerase and a DNA primer-template molecule (e.g., nucleic acid). In embodiments, the polymerase is non-covalently bound to a nucleic acid primer and the template nucleic acid molecule.

The terms "sequencing", "sequence determination", "determining a nucleotide sequence", and the like include determination of partial as well as full sequence information of the polynucleotide being sequenced. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide.

The term "sequencing reaction mixture" refers to an aqueous mixture that contains the reagents necessary to allow a dNTP or dNTP analogue to add a nucleotide to a DNA strand by a DNA polymerase. Exemplary mixtures include buffers (e.g., saline-sodium citrate (SSC), tris(hydroxymethyl)aminomethane or "Tris"), salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents or stabilizers (e.g., PEG, Tween®, BSA). Tween® is a registered trademark of Croda International PLC.

The term "solid substrate" means any suitable medium present in the solid phase to which an antibody or an agent can be covalently or non-covalently affixed or immobilized. Preferred solid substrates are glass. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor®, silica or silica-based materials including silicon and modified silicon, carbon, metals, inorganic glasses, optical fiber bundles, and polymers. Zeonor® is a registered trademark of Zeon Corporation.

The term "species", when used in the context of describing a particular compound or molecule species, refers to a population of chemically indistinct molecules. When used in the context of taxonomy, "species" is the basic unit of classification and a taxonomic rank. For example, in reference to the microorganism *Pyrococcus horikoshii, horikoshii* is a species of the genus *Pyrococcus.*

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

"Control" or "control experiment" is used in accordance with its plain ordinary meaning and refers to an experiment in which the subjects (e.g., enzymes) or reagents of the experiment are treated as in a parallel experiment except for omission of a procedure, reagent, or variable of the experiment (e.g., a polymerase not having one or more mutations relative to the polymerase being tested). In some instances, the control is used as a standard of comparison in evaluating experimental effects. In some embodiments, a control is the measurement of the activity of a protein in the absence of a mutation as described herein (including embodiments and examples). "Control polymerase" is defined herein as the polymerase against which the activity of the altered polymerase is compared. In one embodiment of the invention the control polymerase may comprise a wild type polymerase or an exo-variant thereof. Unless otherwise stated, by "wild type" it is generally meant that the polymerase comprises its natural amino acid sequence, as it would be found in nature. The invention is not limited to merely a comparison of activity of the polymerases as described herein against the wild type equivalent or exo-variant of the polymerase that is being altered. Many polymerases exist whose amino acid sequence has been modified (e.g., by amino acid substitution mutations) and which can prove to be a suitable control for use in assessing the modified nucleotide incorporation efficiencies of the polymerases as described herein. The control polymerase can, therefore, comprise any known polymerase, including mutant polymerases known in the art. The activity of the chosen "control" polymerase with respect to incorporation of the desired nucleotide analogues may be determined by an incorporation assay. In embodiments, the control includes performing the experiment with a wild type polymerase.

The term "modulate" is used in accordance with its plain ordinary meaning and refers to the act of changing or varying one or more properties. "Modulation" refers to the process of changing or varying one or more properties.

The term "kit" is used in accordance with its plain ordinary meaning and refers to any delivery system for delivering materials or reagents for carrying out a method of the invention. Such delivery systems include systems that allow for the storage, transport, or delivery of reaction reagents (e.g., nucleotides, enzymes, nucleic acid templates, etc. in the appropriate containers) and/or supporting materials (e.g., buffers, written instructions for performing the reaction, etc.) from one location to another location. For example, kits include one or more enclosures (e.g., boxes) containing the relevant reaction reagents and/or supporting materials. Such contents may be delivered to the intended recipient together or separately. For example, a first container may contain an enzyme, while a second container contains nucleotides. In embodiments, the kit includes vessels containing one or more enzymes, primers, adaptors, or other reagents as described herein. Vessels may include any structure capable of supporting or containing a liquid or solid material and may include tubes, vials, jars, containers, tips, etc. In embodiments, a wall of a vessel may permit the transmission of light through the wall. In embodiments, the vessel may be optically clear. The kit may include the enzyme and/or nucleotides in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Synthetic" DNA polymerases refer to non-naturally occurring DNA polymerases such as those constructed by synthetic methods, mutated parent DNA polymerases such as truncated DNA polymerases and fusion DNA polymerases (e.g., as described in U.S. Pat. No. 7,541,170). Variants of the parent DNA polymerase have been engineered by mutating residues using site-directed or random mutagenesis methods known in the art. The variant is expressed in an expression system such as *E. coli* by methods known in the art.

The term "isolated" means altered or removed from the natural state. For example, a nucleic acid or a polypeptide naturally present in a living animal is not isolated, but the same nucleic acid or polypeptide partially or completely separated from the coexisting materials of its natural state is isolated. An isolated nucleic acid or protein can exist in substantially purified form, or can exist in a non-native environment such as, for example, a host cell. In embodiments, "isolated" refers to a nucleic acid, polynucleotide, polypeptide, protein, or other component that is partially or completely separated from components with which it is normally associated (other proteins, nucleic acids, cells, etc.).

As used herein, the terms "biomolecule" or "analyte" refer to an agent (e.g., a compound, macromolecule, or small molecule), and the like derived from a biological system (e.g., an organism, a cell, or a tissue). The biomolecule may contain multiple individual components that collectively construct the biomolecule, for example, in embodiments, the biomolecule is a polynucleotide wherein the polynucleotide is composed of nucleotide monomers. The biomolecule may be or may include DNA, RNA, organelles, carbohydrates, lipids, proteins, or any combination thereof. These components may be extracellular. In some examples, the biomolecule may be referred to as a clump or aggregate of combinations of components. In some instances, the biomolecule may include one or more constituents of a cell but may not include other constituents of the cell. In embodiments, a biomolecule is a molecule produced by a biological system (e.g., an organism). The biomolecule may be any substance (e.g. molecule) or entity that is desired to be detected by the method of the invention. The biomolecule is the "target" of the assay method of the invention. The biomolecule may accordingly be any compound that may be desired to be detected, for example a peptide or protein, or nucleic acid molecule or a small molecule, including organic and inorganic molecules. The biomolecule may be a cell or a microorganism, including a virus, or a fragment or product thereof. Biomolecules of particular interest may thus include proteinaceous molecules such as peptides, polypeptides, proteins or prions or any molecule which includes a protein or polypeptide component, etc., or fragments thereof. The biomolecule may be a single molecule or a complex that contains two or more molecular subunits, which may or may not be covalently bound to one another, and which may be the same or different. Thus, in addition to cells or microorganisms, such a complex biomolecule may also be a protein complex. Such a complex may thus be a homo- or hetero-multimer. Aggregates of molecules e.g., proteins may also be target analytes, for example aggregates of the same protein or different proteins. The biomolecule may also be a complex between proteins or peptides and nucleic acid molecules such as DNA or RNA. Of particular interest may be the interactions between proteins and nucleic acids, e.g., regulatory factors, such as transcription factors, and interactions between DNA or RNA molecules.

As used herein, "biomaterial" refers to any biological material produced by an organism. In some embodiments, biomaterial includes secretions, extracellular matrix, proteins, lipids, organelles, membranes, cells, portions thereof, and combinations thereof. In some embodiments, cellular material includes secretions, extracellular matrix, proteins, lipids, organelles, membranes, cells, portions thereof, and combinations thereof. In some embodiments, biomaterial includes viruses. In some embodiments, the biomaterial is a replicating virus and thus includes virus infected cells. In embodiments, a biological sample includes biomaterials.

As used herein, the term "primed template DNA molecule" refers to a template DNA molecule which is associated with a primer (a short polynucleotide) that can serve as a starting point for DNA synthesis.

As used herein, the term "incorporating a nucleotide into a nucleic acid sequence" refers to the process of joining a cognate nucleotide to a nucleic acid primer by formation of a phosphodiester bond. As described herein, methods of incorporating a nucleotide into a nucleic acid sequence comprises combining in a reaction vessel: (i) a nucleic acid template, (ii) a nucleotide solution comprising a plurality of nucleotides, and (iii) a polymerase as described herein.

As used herein, the term "primer-template hybridization complex" refers to a double stranded nucleic acid complex formed as a result of a hybridization event between a DNA template molecule and a primer. In embodiments, the formation of a template complex enables elongation at the 3' end of the primer.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer). Amplification according to the present disclosure encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA (oligonucleotide ligation assay)/PCR, PCR/OLA, LDR/PCR, PCR/PCR/LDR, PCR/LDR, LCR/PCR, PCR/LCR (also known as combined chain reaction-CCR), and the like.

In some embodiments, amplification includes at least one cycle of the sequential procedures of: annealing at least one primer with complementary or substantially complementary sequences in at least one target nucleic acid; synthesizing at least one strand of nucleotides in a template-dependent manner using a polymerase; and optionally denaturing the newly-formed nucleic acid duplex to separate the strands. The cycle may or may not be repeated. Amplification can include thermocycling or can be performed isothermally.

As used herein, the term "rolling circle amplification (RCA)" refers to a nucleic acid amplification reaction that amplifies a circular nucleic acid template (e.g., single-stranded DNA circles) via a rolling circle process. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers including tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as a polymerase described herein. RCA may be performed by using any of the DNA polymerases described herein.

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification includes a nucleic acid amplification reaction including only one species of oligonucleotide primer immobilized to a surface or substrate. In certain embodiments solid phase amplification includes a plurality of different immobilized oligonucleotide primer species. In some embodiments solid phase amplification may include a nucleic acid amplification reaction including one species of oligonucleotide primer immobilized on a solid surface and a second different oligonucleotide primer species in solution. Multiple different species of immobilized or solution-based primers can be used.

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

Provided herein are methods and compositions for analyzing a sample (e.g., sequencing nucleic acids within a sample). A sample (e.g., a sample including nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid).

In some embodiments, a sample includes one or more nucleic acids, or fragments thereof. A sample can include nucleic acids obtained from one or more subjects. In some embodiments a sample includes nucleic acid obtained from a single subject. In some embodiments, a sample includes a mixture of nucleic acids. A mixture of nucleic acids can include two or more nucleic acid species having different nucleotide sequences, different fragment lengths, different origins (e.g., genomic origins, cell or tissue origins, subject origins, the like or combinations thereof), or combinations thereof.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

The methods and kits of the present disclosure may be applied, mutatis mutandis, to the sequencing of RNA, or to determining the identity of a ribonucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

II. Compositions & Kits

Provided herein are compositions including mutant polypeptides (i.e., mutant polymerases) exhibiting increased incorporation of nucleotides relative to a control (e.g., wildtype polymerase). Mutations in the polymerases described herein variously include one or more changes to amino acid residues present in the polypeptide sequence. Additions, substitutions, or deletions are all examples of mutations that are used to generate mutant polypeptides. Substitutions in some instances include the exchange of one amino acid for an alternative amino acid, and such alternative amino acids differ from the original amino acid with regard to size, shape, conformation, or chemical structure. Mutations in some instances are conservative or non-conservative. Conservative mutations comprise the substitution of an amino acid with an amino acid that possesses similar chemical properties. Additions often comprise the insertion of one or more amino acids at the N-terminal, C-terminal, or internal positions of the polypeptide. In some embodiments, additions include fusion polypeptides, wherein one or more additional polypeptides (i.e., a polypeptide from a different source) is connected (e.g., covalently linked to the N- or C-terminus) to the polymerase as described herein. Such additional polypeptides include domains with additional activity, or sequences with additional function (e.g., improve expression, aid purification, improve solubility, attach to a solid support, or other function).

Wild type polymerase sequences are typical initial sequences for protein or enzyme engineering to generate mutant polymerases. In some embodiments, a polypeptide differs from a wild-type sequence (naturally occurring) by at least one amino acid. Any number of mutations is introduced into a polypeptide or portion of a polypeptide described herein, such as 1, 2, 3, 4, 5, 6, 7, 8, 9, 10, 20, 50, or more than 50 mutations. In embodiments, the polymerase differs from a wild-type sequence by at least two amino acids. In embodiments, the polymerase differs from a wild-type sequence by at least three, four, five, or at least six amino acids.

In an aspect is provided a polymerase including one or more amino acid substitutions as described herein. In embodiments, the polymerase includes an amino acid sequence that is at least 50% identical to SEQ ID NO:1 (e.g., 50% identical, 60% identical, 70% identical, 80% identical, 90% identical, or greater); and includes an amino acid substitution, wherein the amino acid substitution is: a proline, tryptophan, phenylalanine, tyrosine, alanine, or glycine an amino acid position corresponding to position 216 of SEQ ID NO:1; an arginine, lysine, asparagine, glutamine, alanine, or glycine at an amino acid position corresponding to position 417 of SEQ ID NO:1; a valine, lysine, asparagine, glutamine, alanine, or glycine at an amino acid position corresponding to position 394 of SEQ ID NO:1; and/or an asparagine, glutamine, alanine, or glycine at an amino acid position corresponding to position 93 of SEQ ID NO:1.

In embodiments, the polymerase includes an amino acid sequence that is at least 80% identical to SEQ ID NO:1; and includes an amino acid substitution, wherein the amino acid substitution is: a proline, tryptophan, phenylalanine, tyrosine, alanine, or glycine an amino acid position corresponding to position 216 of SEQ ID NO:1; an arginine, lysine, asparagine, glutamine, alanine, or glycine at an amino acid position corresponding to position 417 of SEQ ID NO:1; a valine, lysine, asparagine, glutamine, alanine, or glycine at an amino acid position corresponding to position 394 of SEQ ID NO:1; or an asparagine, glutamine, alanine, or glycine at an amino acid position corresponding to position 93 of SEQ ID NO:1.

In embodiments, the polymerase includes an amino acid sequence that is at least 50%, 60%, 70%, 80%, 85%, 90%, 95%, or at least 99% identical to SEQ ID NO:1; and includes an amino acid substitution as described herein. In embodiments, the amino acid substitution is a proline, tryptophan, phenylalanine, tyrosine, alanine, or glycine an amino acid position corresponding to position 216 of SEQ ID NO:1. In embodiments, the amino acid substitution is an arginine, lysine, asparagine, glutamine, alanine, or glycine at an amino acid position corresponding to position 417 of SEQ ID NO:1. In embodiments, the amino acid substitution is a valine, lysine, asparagine, glutamine, alanine, or glycine at an amino acid position corresponding to position 394 of SEQ ID NO:1. In embodiments, the amino acid substitution is an asparagine, glutamine, alanine, or glycine at an amino acid position corresponding to position 93 of SEQ ID NO:1.

In another aspect is provided a polymerase including an amino acid sequence that is at least 85% identical to SEQ ID NO: 1; including a serine, threonine, tyrosine, alanine, or glycine at an amino acid position corresponding to position 87 of SEQ ID NO:1; an asparagine, glutamine, alanine, or glycine at an amino acid position corresponding to position 93 of SEQ ID NO:1; a valine, leucine, alanine, or glycine at an amino acid position corresponding to position 378 of SEQ ID NO:1; a glutamic acid, aspartic acid, alanine, glycine, or threonine at an amino acid position corresponding to position 536 of SEQ ID NO:1; and a glycine, alanine, valine, serine, or threonine at an amino acid position corresponding to position 578 of SEQ ID NO:1. In embodiments, the polymerase includes an arginine, histidine, asparagine, glutamine, alanine, or glycine at an amino acid position corresponding to position 366 of SEQ ID NO:1.

In embodiments, the polymerase includes an arginine, lysine, asparagine, or glutamine at the amino acid position corresponding to position 417 of SEQ ID NO:1. An amino acid sequence alignment can provide amino acid positions corresponding to position 417 of SEQ ID NO:1. For example, the amino acid position 414 of SEQ ID NO:2 corresponds to position 417 of SEQ ID NO:1. In embodiments, the polymerase is an arginine at the amino acid position corresponding to position 417 of SEQ ID NO:1. In embodiments, the polymerase is a lysine at the amino acid position corresponding to position 417 of SEQ ID NO:1. In embodiments, the polymerase is an asparagine at the amino acid position corresponding to position 417 of SEQ ID NO:1. In embodiments, the polymerase is a glutamine at the amino acid position corresponding to position 417 of SEQ ID NO:1.

In embodiments, the polymerase includes a valine, lysine, alanine, or glycine at the amino acid position corresponding to position 394 of SEQ ID NO:1. An amino acid sequence alignment can provide amino acid positions corresponding to position 394 of SEQ ID NO:1. For example, the amino acid position 391 of SEQ ID NO:2 corresponds to position 394 of SEQ ID NO:1. In embodiments, the polymerase is a valine at the amino acid position corresponding to position 394. In embodiments, the polymerase is a lysine at the amino acid position corresponding to position 394. In embodiments, the polymerase is an alanine at the amino acid position corresponding to position 394. In embodiments, the polymerase is a glycine at the amino acid position corresponding to position 394.

In embodiments, the polymerase includes a proline, tryptophan, phenylalanine, tyrosine, alanine, or glycine at the amino acid position corresponding to position 216 of SEQ ID NO:1; and includes a glutamic acid, aspartic acid, alanine, or glycine at an amino acid position corresponding to position 135 of SEQ ID NO:1.

In embodiments, the polymerase includes a proline at the amino acid position corresponding to position 216 of SEQ ID NO:1; and includes a glutamic acid, aspartic acid, alanine, or glycine at an amino acid position corresponding to position 135 of SEQ ID NO:1. In embodiments, the polymerase includes a tryptophan at the amino acid position corresponding to position 216 of SEQ ID NO:1; and includes a glutamic acid, aspartic acid, alanine, or glycine at an amino acid position corresponding to position 135 of SEQ ID NO:1.In embodiments, the polymerase includes a phenylalanine at the amino acid position corresponding to position 216 of SEQ ID NO:1; and includes a glutamic acid, aspartic acid, alanine, or glycine at an amino acid position corresponding to position 135 of SEQ ID NO:1. In embodiments, the polymerase includes a tyrosine at the amino acid position corresponding to position 216 of SEQ ID NO:1; and includes a glutamic acid, aspartic acid, alanine, or glycine at an amino acid position corresponding to position 135 of SEQ ID NO:1. In embodiments, the polymerase includes an alanine at the amino acid position corresponding to position 216 of SEQ ID NO:1; and includes a glutamic acid, aspartic acid, alanine, or glycine at an amino acid position corresponding to position 135 of SEQ ID NO:1. In embodiments, the polymerase includes a glycine at the amino acid position corresponding to position 216 of SEQ ID NO:1; and includes a glutamic acid, aspartic acid, alanine, or glycine at an amino acid position corresponding to position 135 of SEQ ID NO:1.

In embodiments, the polymerase includes a proline, tryptophan, phenylalanine, tyrosine, alanine, or glycine at the amino acid position corresponding to position 216 of SEQ ID NO:1; and includes a glutamic acid at an amino acid position corresponding to position 135 of SEQ ID NO:1. In embodiments, the polymerase includes a proline, tryptophan, phenylalanine, tyrosine, alanine, or glycine at the amino acid position corresponding to position 216 of SEQ ID NO:1; and includes an aspartic acid at an amino acid position corresponding to position 135 of SEQ ID NO:1. In embodiments, the polymerase includes a proline, tryptophan, phenylalanine, tyrosine, alanine, or glycine at the amino acid position corresponding to position 216 of SEQ ID NO:1; and includes an alanine at an amino acid position corresponding to position 135 of SEQ ID NO:1. In embodiments, the polymerase includes a proline, tryptophan, phenylalanine, tyrosine, alanine, or glycine at the amino acid position corresponding to position 216 of SEQ ID NO:1; and includes a glycine at an amino acid position corresponding to position 135 of SEQ ID NO:1.

In embodiments, the polymerase includes a glutamic acid, aspartic acid, alanine, glycine, or threonine at an amino acid position corresponding to position 536 of SEQ ID NO:1. An amino acid sequence alignment can provide amino acid positions corresponding to position 536 of SEQ ID NO:1. For example, the amino acid position 533 of SEQ ID NO:2 corresponds to position 536 of SEQ ID NO: 1. In embodiments, the polymerase includes a glutamic acid at an amino acid position corresponding to position 536. In embodiments, the polymerase includes an aspartic acid at an amino acid position corresponding to position 536. In embodiments, the polymerase includes an alanine at an amino acid position corresponding to position 536. In embodiments, the polymerase includes a glycine at an amino acid position corresponding to position 536. In embodiments, the polymerase includes a threonine at an amino acid position corresponding to position 536.

In embodiments, the polymerase includes a proline at the amino acid position corresponding to position 216; a glutamic acid, aspartic acid, alanine, or glycine at the amino acid position corresponding to position 135; and a glutamic acid, aspartic acid, alanine, glycine, or threonine at the amino acid position corresponding to position 536.

In embodiments, the polymerase includes a proline at an amino acid position corresponding to position 216; a glutamic acid or aspartic acid at the amino acid position corresponding to position 135; and a glutamic acid or aspartic acid at the amino acid position corresponding to position 536.

In embodiments, the polymerase includes a proline at the amino acid position corresponding to position 216; a glutamic acid at the amino acid position corresponding to position 135; and a glutamic acid at the amino acid position corresponding to position 536.

In embodiments, the polymerase includes a serine, threonine, tyrosine, alanine, or glycine at an amino acid position corresponding to position 87 of SEQ ID NO:1. An amino acid sequence alignment can provide amino acid positions corresponding to position 87 of SEQ ID NO:1. For example, the amino acid position 84 of SEQ ID NO:2 corresponds to position 87 of SEQ ID NO:1. In embodiments, the polymerase includes a serine at an amino acid position corresponding to position 87 of SEQ ID NO:1. In embodiments, the polymerase includes a threonine at an amino acid position corresponding to position 87 of SEQ ID NO:1. In embodiments, the polymerase includes a tyrosine at an amino acid position corresponding to position 87 of SEQ ID NO:1. In embodiments, the polymerase includes an alanine at an amino acid position corresponding to position 87 of SEQ ID NO:1. In embodiments, the polymerase includes a glycine at an amino acid position corresponding to position 87 of SEQ ID NO:1.

In embodiments, the polymerase includes a valine, leucine, alanine, or glycine at an amino acid position corresponding to position 378 of SEQ ID NO:1. An amino acid sequence alignment can provide amino acid positions corresponding to position 378 of SEQ ID NO:1. For example, the amino acid position 375 of SEQ ID NO:2 corresponds to position 378 of SEQ ID NO:1. In embodiments, the polymerase includes a valine at the amino acid position corresponding to position 378 of SEQ ID NO:1. In embodiments, the polymerase includes a leucine at the amino acid position corresponding to position 378 of SEQ ID NO:1. In embodiments, the polymerase includes an alanine at the amino acid position corresponding to position 378 of SEQ ID NO:1. In embodiments, the polymerase includes a glycine at the amino acid position corresponding to position 378 of SEQ ID NO:1.

In embodiments, the polymerase includes a lysine at the amino acid position corresponding to position 470 of SEQ ID NO:1. In embodiments, the polymerase includes a lysine at the amino acid position corresponding to position 474 of SEQ ID NO:1.

In embodiments, the polymerase includes a glycine, alanine, valine, serine, or threonine at an amino acid position corresponding to position 578 of SEQ ID NO:1. An amino acid sequence alignment can provide amino acid positions corresponding to position 578 of SEQ ID NO:1. For example, the amino acid position 575 of SEQ ID NO:2 corresponds to position 578 of SEQ ID NO:1. In embodiments, the polymerase includes a glycine at the amino acid position corresponding to position 578 of SEQ ID NO:1. In embodiments, the polymerase includes an alanine at the amino acid position corresponding to position 578 of SEQ ID NO:1. In embodiments, the polymerase includes a valine at the amino acid position corresponding to position 578 of SEQ ID NO:1. In embodiments, the polymerase includes a serine at the amino acid position corresponding to position 578 of SEQ ID NO:1. In embodiments, the polymerase includes a threonine at the amino acid position corresponding to position 578 of SEQ ID NO:1.

In embodiments, the polymerase includes an arginine, histidine, asparagine, glutamine, alanine, or glycine at an amino acid position corresponding to position 366 of SEQ ID NO:1. An amino acid sequence alignment can provide amino acid positions corresponding to position 366 of SEQ ID NO:1. For example, the amino acid position 363 of SEQ ID NO:2 corresponds to position 366 of SEQ ID NO:1. In embodiments, the polymerase includes an arginine at the amino acid position corresponding to position 366 of SEQ ID NO:1. In embodiments, the polymerase includes a histidine at the amino acid position corresponding to position 366 of SEQ ID NO:1. In embodiments, the polymerase includes an asparagine at the amino acid position corresponding to position 366 of SEQ ID NO:1. In embodiments, the polymerase includes a glutamine at the amino acid position corresponding to position 366 of SEQ ID NO:1. In embodiments, the polymerase includes an alanine at the amino acid position corresponding to position 366 of SEQ ID NO:1. In embodiments, the polymerase includes a glycine at the amino acid position corresponding to position 366 of SEQ ID NO:1.

In embodiments, the polymerase includes an alanine, lysine, arginine, histidine, asparagine, and glutamine at an amino acid position corresponding to position 8 of SEQ ID NO:1. In embodiments, the polymerase includes an alanine at an amino acid position corresponding to position 8 of SEQ ID NO:1. In embodiments, the polymerase includes a lysine at an amino acid position corresponding to position 8 of SEQ ID NO:1. In embodiments, the polymerase includes an arginine at an amino acid position corresponding to position 8 of SEQ ID NO:1. In embodiments, the polymerase includes a histidine at an amino acid position corresponding to position 8 of SEQ ID NO:1. In embodiments, the polymerase includes an asparagine at an amino acid position corresponding to position 8 of SEQ ID NO:1. In embodiments, the polymerase includes a glutamine at an amino acid position corresponding to position 8 of SEQ ID NO:1.

In embodiments, the polymerase includes a lysine at an amino acid position corresponding to position 8 and a proline at amino acid position corresponding to position 216 of SEQ ID NO:1. In embodiments, the polymerase includes a lysine at an amino acid position corresponding to position 8, a proline at amino acid position corresponding to position 216, and a valine at amino acid position corresponding to position 40 of SEQ ID NO:1. In embodiments, the polymerase includes a lysine at an amino acid position corresponding to position 8, a glutamic acid at amino acid position corresponding to position 135, and a proline at amino acid position corresponding to position 216 of SEQ ID NO:1. In embodiments, the polymerase includes a lysine at an amino acid position corresponding to position 8, a glutamic acid at amino acid position corresponding to position 135, a proline at amino acid position corresponding to position 216, and an asparagine at amino acid position corresponding to position 121 of SEQ ID NO:1. In embodiments, the polymerase includes a lysine at an amino acid position corresponding to position 8, a glutamic acid at amino acid position corresponding to position 135, a proline at amino acid position corresponding to position 216, and a serine at amino acid position corresponding to position 424 of SEQ ID NO:1.In embodiments, the polymerase includes a lysine at an amino acid position corresponding to position 8, a glutamic acid at amino acid position corresponding to position 135, and an aspartic acid at amino acid position corresponding to position 155 of SEQ ID NO:1. In embodiments, the polymerase includes a lysine at an amino acid position corresponding to position 8, a glutamic acid at amino acid position corresponding to position 135, a proline at amino acid position corresponding to position 216, an aspartic acid at amino acid position corresponding to position 155, a cysteine at amino acid position corresponding to position 184, and a glutamic acid at amino acid position corresponding to position 536 of SEQ ID NO:1. In embodiments, the polymerase includes a lysine at an amino acid position corresponding to position 8, a valine at amino acid position corresponding to position 40, an asparagine at amino acid position corresponding to position 121, a glutamic acid at amino acid position corresponding to position 131, a glutamic acid at amino acid position corresponding to position 135, an aspartic acid at amino acid position corresponding to position 155, a cysteine at amino acid position corresponding to position 184, a proline at amino acid position corresponding to position 216, a glutamic acid at amino acid position corresponding to position 536, and a glutamic acid at amino acid position corresponding to position 539 of SEQ ID NO:1.

In embodiments, the polymerase includes an aspartic acid at an amino acid position corresponding to position 155 of SEQ ID NO:1.

In embodiments, the polymerase includes a glutamic acid at an amino acid position corresponding to position 538 of SEQ ID NO:1.

In embodiments, the polymerase includes a glutamic acid at an amino acid position corresponding to position 539 of SEQ ID NO:1. In embodiments, the polymerase includes a glutamic acid at an amino acid position corresponding to position 538 and a glutamic acid at an amino acid position corresponding to position 539 of SEQ ID NO:1.

In embodiments, the polymerase includes a glutamic acid at an amino acid position corresponding to position 131 of SEQ ID NO:1.

In embodiments, the polymerase includes a glutamic acid at an amino acid position corresponding to position 132 of SEQ ID NO:1.

In another aspect is provided a polymerase including an amino acid sequence that is at least 50% identical to SEQ ID NO: 1; including one or more of the following amino acid substitutions: A324T, A394G, A394K, A394N, A394Q, A394V, A444I, D219N, D34A, D34E, D34N, D34Q, E239A, E239V, E486V, F198L, F47I, G401A, G401L, G401V, G417A, G417K, G417N, G417Q, G417R, G579A, G579S, G579T, G579Y, H485L, I119A, I119G, I119L, I119V, I179F, I378A, I378G, I378L, I378V, I93A, I93G, I93N, I93Q, K131E, K132E, K135A, K135D, K135E, K135G, K311N, K311Q, K311R, K366A, K366G, K366H, K366N, K366Q, K366R, K536A, K536D, K536E, K536G, K536T, K539E, L216A, L216F, L216G, L216P, L216W, L216Y, L381Q, L462A, L462G, L462I, L462L, L462V, L567M, P87A, P87G, P87S, P87T, P87Y, R552A, R552N, R552Q, S192A, S192C, S192G, S260N, S260Q, S487C, S578A, S578G, S578I, S578L, S578T, S578V, T203S, T231A, T231I, T231V, T434A, T434G, T434Y, V565A, V565G, V565M, W436R, Y343C, Y500A, Y500F, and/or Y500G. In embodiments, the polymerase includes an amino acid sequence that is at least 50%, 60%, 70%, 80%, 85%, 90%, 95%, or at least 99% identical to SEQ ID NO:1; and includes an amino acid substitution as described herein. In embodiments, the polymerase includes two or more of the mutations identified in the list above. In embodiments, the polymerase includes three or more of the mutations identified in the list above. In embodiments, the polymerase includes four or more of the mutations identified in the list above. In embodiments, the polymerase includes one of the mutations identified in the list above. In embodiments, the polymerase includes two of the mutations identified in the list above. In embodiments, the polymerase includes three of the mutations identified in the list above. In embodiments, the polymerase includes four of the mutations identified in the list above.

In another aspect is provided a polymerase including an amino acid sequence that is at least 50% identical to SEQ ID NO: 1; including one or more of the following amino acid substitutions: A83T, A83V, A324T, A394G, A394K, A394N, A394Q, A394V, A444I, D219N, D34A, D34E, D34N, D34Q, D121N, E239A, E239V, E486V, F198L, F47I, G155D, G155C, G184C, G401A, G401L, G401V, G417A, G417K, G417N, G417Q, G417R, G579A, G579S, G579T, G579Y, H485L, I40V, I119A, I119G, I119L, I119V, I179F, I378A, I378G, I378L, I378V, I93A, I93G, I93N, I93Q, K125R, K131A, K131D, K131E, K131G, K131T, K132A, K132D, K132E, K132G, K132T, K135A, K135D, K135E, K135G, K311N, K311Q, K311R, K366A, K366G, K366H, K366N, K366Q, K366R, K536A, K536D, K536E, K536G, K536T, K539A, K539D, K539E, K539G, K539T, L156P, L156H, L216A, L216F, L216G, L216P, L216W, L216Y, L381Q, L462A, L462G, L462I, L462L, L462V, L567M, P87A, P87G, P87S, P87T, P87Y, P264A, P424S, R552A, R552N, R552Q, S192A, S192C, S192G, S260N, S260Q, S487C, S578A, S578G, S578I, S578L, S578T, S578V, T15A, T15K, T15P, T203S, T231A, T231I, T231V, T434A, T434G, T434Y, V565A, V565G, V565M, W50P, W50R, W436R, Y120H, Y184A, Y343C, Y500A, Y500F, and/or Y500G. In embodiments, the polymerase includes an amino acid sequence that is at least 50%, 60%, 70%, 80%, 85%, 90%, 95%, or at least 99% identical to SEQ ID NO:1; and includes an amino acid substitution as described herein. In embodiments, the polymerase includes two or more of the mutations identified in the list above. In embodiments, the polymerase includes three or more of the mutations identified in the list above. In embodiments, the polymerase includes four or more of the mutations identified in the list above. In embodiments, the polymerase includes one of the mutations identified in the list above. In embodiments, the polymerase includes two of the mutations identified in the list above. In embodiments, the polymerase includes three of the mutations identified in the list above. In embodiments, the polymerase includes four of the mutations identified in the list above.

In embodiments, the polymerase includes one or more of the following amino acid substitutions: V19L, E20D, N31E, E33G, H35L, D34N, S36D, E37N, A49Q, L52M, K53E, I71V, N77H, A83N, D84E, R96K, L107F, I115L, K131E, K132E, K135E, T140P, V141L, Y156H, K157E, A164E, Q171E, E175R, L178D, I202L, T203S, K208N, T213K, L216P, G217P, V222I, R236K, F237Y, L262P, E267A, E272Q V276E, W277K, D280Q, H287R, C290F, R306K, S307N, R308P, Y310F, S318N, I323P, A324V, D325E, W327Y, S329T, M336I, K337Q, D341E, S349D, L351F, K354R, A355E, T356K, I370V, T373H, S374E, N409D, A411S, L416V, E418D, T421Y, Y439F, I467V, D469E, V470I, G516C, D520E, Y521A, D523T, I524T, K536E, K536T, K539E, E540K, E544D, R552S, M554G, P562N, D570S, and/or T571V.

In embodiments, the polymerase includes the amino acid substitution V19L. In embodiments, the polymerase includes the amino acid substitution E20D. In embodiments, the polymerase includes the amino acid substitution N31E. In embodiments, the polymerase includes the amino acid substitution E33G. In embodiments, the polymerase includes the amino acid substitution D34N. In embodiments, the polymerase includes the amino acid substitution H35L. In embodiments, the polymerase includes the amino acid substitution S36D. In embodiments, the polymerase includes the amino acid substitution E37N. In embodiments, the polymerase includes the amino acid substitution A49Q. In embodiments, the polymerase includes the amino acid substitution L52M. In embodiments, the polymerase includes the amino acid substitution K53E. In embodiments, the polymerase includes the amino acid substitution I71V. In embodiments, the polymerase includes the amino acid substitution N77H. In embodiments, the polymerase includes the amino acid substitution A83N. In embodiments, the polymerase includes the amino acid substitution D84E. In embodiments, the polymerase includes the amino acid substitution R96K. In embodiments, the polymerase includes the amino acid substitution L107F. In embodiments, the polymerase includes the amino acid substitution I115L. In embodiments, the polymerase includes the amino acid substitution K131E. In embodiments, the polymerase includes the amino acid substitution K132E. In embodiments, the polymerase includes the amino acid substitution K135E. In embodiments, the polymerase includes the amino acid substitution T140P. In embodiments, the polymerase includes the amino acid substitution V141L. In embodiments, the polymerase includes the amino acid substitution Y156H. In embodiments, the polymerase includes the amino acid substitution K157E. In embodiments, the polymerase includes the amino acid substitution A164E. In embodiments, the polymerase includes the amino acid substitution Q171E. In embodiments, the polymerase includes the amino acid substitution E175R. In embodiments, the polymerase includes the amino acid substitution L178D. In embodiments, the polymerase includes the amino acid substitution I202L. In embodiments, the polymerase includes the amino acid substitution T203S. In embodiments, the polymerase includes the amino acid substitution K208N. In embodiments, the polymerase includes the amino acid substitution T213K. In embodiments, the polymerase includes the amino acid substitution L216P. In embodiments, the polymerase includes the amino acid substitution G217P. In embodiments, the polymerase includes the amino acid substitution V222I. In embodiments, the polymerase includes the amino acid substitution R236K. In embodiments, the polymerase includes the amino acid substitution F237Y. In embodiments, the polymerase includes the amino acid substitution L262P. In embodiments, the polymerase includes the amino acid substitution E267A. In embodiments, the polymerase includes the amino acid substitution E272Q V276E. In embodiments, the polymerase includes the amino acid substitution W277K. In embodiments, the polymerase includes the amino acid substitution D280Q. In embodiments, the polymerase includes the amino acid substitution H287R. In embodiments, the polymerase includes the amino acid substitution C290F. In embodiments, the polymerase includes the amino acid substitution R306K. In embodiments, the polymerase includes the amino acid substitution S307N. In embodiments, the polymerase includes the amino acid substitution R308P. In embodiments, the polymerase includes the amino acid substitution Y310F. In embodiments, the polymerase includes the amino acid substitution S318N. In embodiments, the polymerase includes the amino acid substitution I323P. In embodiments, the polymerase includes the amino acid substitution A324V. In embodiments, the polymerase includes the amino acid substitution D325E. In embodiments, the polymerase includes the amino acid substitution W327Y. In embodiments, the polymerase includes the amino acid substitution S329T. In embodiments, the polymerase includes the amino acid substitution M336I. In embodiments, the polymerase includes the amino acid substitution K337Q. In embodiments, the polymerase includes the amino acid substitution D341E. In embodiments, the polymerase includes the amino acid substitution S349D. In embodiments, the polymerase includes the amino acid substitution L351F. In embodiments, the polymerase includes the amino acid substitution K354R. In embodiments, the polymerase includes the amino acid substitution A355E. In embodiments, the polymerase includes the amino acid substitution T356K. In embodiments, the polymerase includes the amino acid substitution I370V. In embodiments, the polymerase includes the amino acid substitution T373H. In embodiments, the polymerase includes the amino acid substitution S374E. In embodiments, the polymerase includes the amino acid substitution N409D. In embodiments, the polymerase includes the amino acid substitution A411S. In embodiments, the polymerase includes the amino acid substitution L416V. In embodiments, the polymerase includes the amino acid substitution E418D. In embodiments, the polymerase includes the amino acid substitution T421Y. In embodiments, the polymerase includes the amino acid substitution Y439F. In embodiments, the polymerase includes the amino acid substitution I467V. In embodiments, the polymerase includes the amino acid substitution D469E. In embodiments, the polymerase includes the amino acid substitution V470I. In embodiments, the polymerase includes the amino acid substitution G516C. In embodiments, the polymerase includes the amino acid substitution D520E. In embodiments, the polymerase includes the amino acid substitution Y521A. In embodiments, the polymerase includes the amino acid substitution D523T. In embodiments, the polymerase includes the amino acid substitution I524T. In embodiments, the polymerase includes the amino acid substitution K536E. In embodiments, the polymerase includes the amino acid substitution K536T. In embodiments, the polymerase includes the amino acid substitution K539E. In embodiments, the polymerase includes the amino acid substitution E540K. In embodiments, the polymerase includes the amino acid substitution E544D. In embodiments, the polymerase includes the amino acid substitution R552S. In embodiments, the polymerase includes the amino acid substitution M554G. In embodiments, the polymerase includes the amino acid substitution P562N. In embodiments, the polymerase includes the amino acid substitution D570S. In embodiments, the polymerase includes the amino acid substitution T571V.

For brevity, amino acid mutation nomenclature is used throughout this application. One having skill in the art would understand the amino acid mutation nomenclature, such that D141A refers to aspartic acid (single letter code is D), at position 141, is replaced with alanine (single letter code A). Likewise, it is understood that when an amino acid mutation nomenclature is used and the terminal amino acid code is missing, e.g., P411, it is understood that no mutation was made relative to the wild type. Additionally, for the avoidance of doubt, the wild type amino acid may be recited to emphasize that it is not mutated, for example P411P.

In embodiments, the polymerase includes the amino acid substitution A83T. In embodiments, the polymerase includes the amino acid substitution A83V. In embodiments, the polymerase includes the amino acid substitution A324T. In embodiments, the polymerase includes the amino acid substitution A394G. In embodiments, the polymerase includes the amino acid substitution A394K. In embodiments, the polymerase includes the amino acid substitution A394N. In embodiments, the polymerase includes the amino acid substitution A394Q. In embodiments, the polymerase includes the amino acid substitution A394V. In embodiments, the polymerase includes the amino acid substitution A444I. In embodiments, the polymerase includes the amino acid substitution D219N. In embodiments, the polymerase includes the amino acid substitution D34A. In embodiments, the polymerase includes the amino acid substitution D34E. In embodiments, the polymerase includes the amino acid substitution D34N. In embodiments, the polymerase includes the amino acid substitution D34Q. In embodiments, the polymerase includes the amino acid substitution D121N. In embodiments, the polymerase includes the amino acid substitution E239A. In embodiments, the polymerase includes the amino acid substitution E239V. In embodiments, the polymerase includes the amino acid substitution E486V. In embodiments, the polymerase includes the amino acid substitution F198L. In embodiments, the polymerase includes the amino acid substitution F47I. In embodiments, the polymerase includes the amino acid substitution G155C. In embodiments, the polymerase includes the amino acid substitution G155D. In embodiments, the polymerase includes the amino acid substitution G184C. In embodiments, the polymerase includes the amino acid substitution G401A. In embodiments, the polymerase includes the amino acid substitution G401L. In embodiments, the polymerase includes the amino acid substitution G401V. In embodiments, the polymerase includes the amino acid substitution G417A. In embodiments, the polymerase includes the amino acid substitution G417K. In embodiments, the polymerase includes the amino acid substitution G417N. In embodiments, the polymerase includes the amino acid substitution G417Q. In embodiments, the polymerase includes the amino acid substitution G417R. In embodiments, the polymerase includes the amino acid substitution G579A. In embodiments, the polymerase includes the amino acid substitution G579S. In embodiments, the polymerase includes the amino acid substitution G579T. In embodiments, the polymerase includes the amino acid substitution G579Y. In embodiments, the polymerase includes the amino acid substitution H485L. In embodiments, the polymerase includes the amino acid substitution 140V. In embodiments, the polymerase includes the amino acid substitution I119A. In embodiments, the polymerase includes the amino acid substitution I119G. In embodiments, the polymerase includes the amino acid substitution I119L. In embodiments, the polymerase includes the amino acid substitution I119V. In embodiments, the polymerase includes the amino acid substitution I179F. In embodiments, the polymerase includes the amino acid substitution I378A. In embodiments, the polymerase includes the amino acid substitution I378G. In embodiments, the polymerase includes the amino acid substitution I378L. In embodiments, the polymerase includes the amino acid substitution I378V. In embodiments, the polymerase includes the amino acid substitution I93A. In embodiments, the polymerase includes the amino acid substitution I93G. In embodiments, the polymerase includes the amino acid substitution I93N. In embodiments, the polymerase includes the amino acid substitution I93Q. In embodiments, the polymerase includes the amino acid substitution K125R. In embodiments, the polymerase includes the amino acid substitution K131A. In embodiments, the polymerase includes the amino acid substitution K131D. In embodiments, the polymerase includes the amino acid substitution K131E. In embodiments, the polymerase includes the amino acid substitution K131G. In embodiments, the polymerase includes the amino acid substitution K131T. In embodiments, the polymerase includes the amino acid substitution K132A. In embodiments, the polymerase includes the amino acid substitution K132D. In embodiments, the polymerase includes the amino acid substitution K132E. In embodiments, the polymerase includes the amino acid substitution K132G. In embodiments, the polymerase includes the amino acid substitution K132T. In embodiments, the polymerase includes the amino acid substitution K135A. In embodiments, the polymerase includes the amino acid substitution K135D. In embodiments, the polymerase includes the amino acid substitution K135E. In embodiments, the polymerase includes the amino acid substitution K135G. In embodiments, the polymerase includes the amino acid substitution L156H. In embodiments, the polymerase includes the amino acid substitution L156P. In embodiments, the polymerase includes the amino acid substitution K311N. In embodiments, the polymerase includes the amino acid substitution K311Q. In embodiments, the polymerase includes the amino acid substitution K311R. In embodiments, the polymerase includes the amino acid substitution K366A. In embodiments, the polymerase includes the amino acid substitution K366G. In embodiments, the polymerase includes the amino acid substitution K366H. In embodiments, the polymerase includes the amino acid substitution K366N. In embodiments, the polymerase includes the amino acid substitution K366Q. In embodiments, the polymerase includes the amino acid substitution K366R. In embodiments, the polymerase includes the amino acid substitution K536A. In embodiments, the polymerase includes the amino acid substitution K536D. In embodiments, the polymerase includes the amino acid substitution K536E. In embodiments, the polymerase includes the amino acid substitution K536G. In embodiments, the polymerase includes the amino acid substitution K536T. In embodiments, the polymerase includes the amino acid substitution K538A. In embodiments, the polymerase includes the amino acid substitution K538D. In embodiments, the polymerase includes the amino acid substitution K538E. In embodiments, the polymerase includes the amino acid substitution K538G. In embodiments, the polymerase includes the amino acid substitution K538T. In embodiments, the polymerase includes the amino acid substitution K539A. In embodiments, the polymerase includes the amino acid substitution K539D. In embodiments, the polymerase includes the amino acid substitution K539E. In embodiments, the polymerase includes the amino acid substitution K539G. In embodiments, the polymerase includes the amino acid substitution K539T. In embodiments, the polymerase includes the amino acid substitution L216A. In embodiments, the polymerase includes the amino acid substitution L216F. In embodiments, the polymerase includes the amino acid substitution L216G. In embodiments, the polymerase includes the amino acid substitution L216P. In embodiments, the polymerase includes the amino acid substitution L216W. In embodiments, the polymerase includes the amino acid substitution L216Y. In embodiments, the polymerase includes the amino acid substitution L381Q. In embodiments, the polymerase includes the amino acid substitution L462A. In embodiments, the polymerase includes the amino acid substitution L462G. In embodiments, the polymerase includes the amino acid substitution L462I. In embodiments, the polymerase includes the amino acid substitution L462L. In embodiments, the polymerase includes the amino acid substitution L462V. In embodiments, the polymerase includes the amino acid substitution L567M. In embodiments, the polymerase includes the amino acid substitution M8A. In embodiments, the polymerase includes the amino acid substitution M8H. In embodiments, the polymerase includes the amino acid substitution M8K. In embodiments, the polymerase includes the amino acid substitution M8N. In embodiments, the polymerase includes the amino acid substitution M8Q. In embodiments, the polymerase includes the amino acid substitution M8R. In embodiments, the polymerase includes the amino acid substitution P87A. In embodiments, the polymerase includes the amino acid substitution P87G. In embodiments, the polymerase includes the amino acid substitution P87S. In embodiments, the polymerase includes the amino acid substitution P87T. In embodiments, the polymerase includes the amino acid substitution P87Y. In embodiments, the polymerase includes the amino acid substitution P264A. In embodiments, the polymerase includes the amino acid substitution P424S. In embodiments, the polymerase includes the amino acid substitution R552A. In embodiments, the polymerase includes the amino acid substitution R552N. In embodiments, the polymerase includes the amino acid substitution R552Q. In embodiments, the polymerase includes the amino acid substitution S192A. In embodiments, the polymerase includes the amino acid substitution S192C. In embodiments, the polymerase includes the amino acid substitution S192G. In embodiments, the polymerase includes the amino acid substitution S260N. In embodiments, the polymerase includes the amino acid substitution S260Q. In embodiments, the polymerase includes the amino acid substitution S487C. In embodiments, the polymerase includes the amino acid substitution S578A. In embodiments, the polymerase includes the amino acid substitution S578G. In embodiments, the polymerase includes the amino acid substitution S578I. In embodiments, the polymerase includes the amino acid substitution S578L. In embodiments, the polymerase includes the amino acid substitution S578T. In embodiments, the polymerase includes the amino acid substitution S578V. In embodiments, the polymerase includes the amino acid substitution T15A. In embodiments, the polymerase includes the amino acid substitution T15K. In embodiments, the polymerase includes the amino acid substitution T15P. In embodiments, the polymerase includes the amino acid substitution T203S. In embodiments, the polymerase includes the amino acid substitution T231A. In embodiments, the polymerase includes the amino acid substitution T231I. In embodiments, the polymerase includes the amino acid substitution T231V. In embodiments, the polymerase includes the amino acid substitution T434A. In embodiments, the polymerase includes the amino acid substitution T434G. In embodiments, the polymerase includes the amino acid substitution T434Y. In embodiments, the polymerase includes the amino acid substitution V565A. In embodiments, the polymerase includes the amino acid substitution V565G. In embodiments, the polymerase includes the amino acid substitution V565M. In embodiments, the polymerase includes the amino acid substitution W50P. In embodiments, the polymerase includes the amino acid substitution W50R. In embodiments, the polymerase includes the amino acid substitution W436R. In embodiments, the polymerase includes the amino acid substitution Y120H. In embodiments, the polymerase includes the amino acid substitution Y184A. In embodiments, the polymerase includes the amino acid substitution Y343C. In embodiments, the polymerase includes the amino acid substitution Y500A. In embodiments, the polymerase includes the amino acid substitution Y500F. In embodiments, the polymerase includes the amino acid substitution Y500G.

In embodiments, the polymerase includes the amino acid substitution: D34E, F47I, P87S, I93N, I119V, K131E, K132E, I179F, S192C, F198L, T203S, L216P, D219N, T231I, E239G, S260N, K311R, A324T, Y343C, K366R, I378V, L381Q, A394V, G401V, G417R, W436R, A444V, A447T, L462I, H485L, E486V, S487C, Y500F, K536E, K539E, R552Q, V565M, L567M, S578G, or G579S. In embodiments, the polymerase includes the amino acid substitution D34E. In embodiments, the polymerase includes the amino acid substitution F47I. In embodiments, the polymerase includes the amino acid substitution P87S. In embodiments, the polymerase includes the amino acid substitution I93N. In embodiments, the polymerase includes the amino acid substitution I119V. In embodiments, the polymerase includes the amino acid substitution K131E. In embodiments, the polymerase includes the amino acid substitution K132E. In embodiments, the polymerase includes the amino acid substitution 1179F. In embodiments, the polymerase includes the amino acid substitution S192C. In embodiments, the polymerase includes the amino acid substitution F198L. In embodiments, the polymerase includes the amino acid substitution T203S. In embodiments, the polymerase includes the amino acid substitution L216P. In embodiments, the polymerase includes the amino acid substitution D219N. In embodiments, the polymerase includes the amino acid substitution T231I. In embodiments, the polymerase includes the amino acid substitution E239G. In embodiments, the polymerase includes the amino acid substitution S260N. In embodiments, the polymerase includes the amino acid substitution K311R. In embodiments, the polymerase includes the amino acid substitution A324T. In embodiments, the polymerase includes the amino acid substitution Y343C. In embodiments, the polymerase includes the amino acid substitution K366R. In embodiments, the polymerase includes the amino acid substitution I378V. In embodiments, the polymerase includes the amino acid substitution L381Q. In embodiments, the polymerase includes the amino acid substitution A394V. In embodiments, the polymerase includes the amino acid substitution G401V. In embodiments, the polymerase includes the amino acid substitution G417R. In embodiments, the polymerase includes the amino acid substitution W436R. In embodiments, the polymerase includes the amino acid substitution A444V. In embodiments, the polymerase includes the amino acid substitution A447T. In embodiments, the polymerase includes the amino acid substitution L462I. In embodiments, the polymerase includes the amino acid substitution H485L. In embodiments, the polymerase includes the amino acid substitution E486V. In embodiments, the polymerase includes the amino acid substitution S487C. In embodiments, the polymerase includes the amino acid substitution Y500F. In embodiments, the polymerase includes the amino acid substitution K536E. In embodiments, the polymerase includes the amino acid substitution K539E. In embodiments, the polymerase includes the amino acid substitution R552Q. In embodiments, the polymerase includes the amino acid substitution V565M. In embodiments, the polymerase includes the amino acid substitution L567M. In embodiments, the polymerase includes the amino acid substitution S578G. In embodiments, the polymerase includes the amino acid substitution or G579S.

In embodiments, the polymerase includes the amino acid substitution K135E; L216P; and K536E. In embodiments, the polymerase includes the amino acid substitution G417R. In embodiments, the polymerase includes the amino acid substitution K135E; and L216P. In embodiments, the polymerase includes the amino acid substitution A394V. In embodiments, the polymerase includes the amino acid substitution P87S; I93N; K366R; I378V; K536E; and S578G. In embodiments, the polymerase includes the amino acid substitution P87S; I93N; I378V; K536E; and S578G. In embodiments, the polymerase includes the amino acid substitution P87S; I93N; K135E; I378V; K536E; and S578G.

In embodiments, mutations may include substitution of the amino acid in the parent amino acid sequences with an amino acid, which is not the parent amino acid. In embodiments, the mutations may result in conservative amino acid changes. In embodiments, non-polar amino acids may be converted into polar amino acids (threonine, asparagine, glutamine, cysteine, tyrosine, aspartic acid, glutamic acid or histidine) or the parent amino acid may be changed to an alanine.

In an aspect is provided a polymerase including an amino acid sequence that is at least 50% identical to SEQ ID NO: 1; including a proline, tryptophan, phenylalanine, tyrosine, alanine, or glycine at an amino acid position corresponding to position 216 of SEQ ID NO:1; and a glutamic acid, aspartic acid, alanine, or glycine at an amino acid position corresponding to position 135 of SEQ ID NO:1. In embodiments, the polymerase includes an amino acid sequence that is at least 50%, 60%, 70%, 80%, 85%, 90%, 95%, or at least 99% identical to SEQ ID NO:1; and includes an amino acid substitution as described herein. In embodiments, the polymerase includes an amino acid sequence that is 80% identical to SEQ ID NO: 1; including a proline, tryptophan, phenylalanine, tyrosine, alanine, or glycine at an amino acid position corresponding to position 216 of SEQ ID NO:1; and a glutamic acid, aspartic acid, alanine, or glycine at an amino acid position corresponding to position 135 of SEQ ID NO:1. In embodiments, the polymerase includes a proline at the amino acid position corresponding to position 216 of SEQ ID NO:1. In embodiments, the polymerase further includes a glutamic acid, aspartic acid, alanine, glycine, or threonine at an amino acid position corresponding to position 536 of SEQ ID NO:1.

In embodiments, the polymerase includes a glutamic acid, aspartic acid, alanine, glycine, or threonine at an amino acid position corresponding to position 538 of SEQ ID NO:1. In embodiments, the polymerase includes a glutamic acid at an amino acid position corresponding to position 538 of SEQ ID NO:1. In embodiments, the polymerase includes an aspartic acid at an amino acid position corresponding to position 538 of SEQ ID NO:1. In embodiments, the polymerase includes an alanine at an amino acid position corresponding to position 538 of SEQ ID NO:1. In embodiments, the polymerase includes a glycine at an amino acid position corresponding to position 538 of SEQ ID NO:1. In embodiments, the polymerase includes a threonine at an amino acid position corresponding to position 538 of SEQ ID NO:1.

In embodiments, the polymerase includes a proline, tryptophan, phenylalanine, tyrosine, alanine, or glycine at the amino acid position corresponding to position 216; a glutamic acid, aspartic acid, alanine, or glycine at an amino acid position corresponding to position 135; a glutamic acid, aspartic acid, alanine, glycine, or threonine at an amino acid position corresponding to position 536; and glutamic acid, aspartic acid, alanine, glycine, or threonine at amino acid position corresponding to position 538 of SEQ ID NO:1. In embodiments, the polymerase includes a proline at an amino acid position corresponding to position 216; a glutamic acid or aspartic acid at the amino acid position corresponding to position 135; a glutamic acid or aspartic acid at the amino acid position corresponding to position 536; and a glutamic acid and amino acid position corresponding to position 538 of SEQ ID NO:1. In embodiments, the polymerase includes a proline at the amino acid position corresponding to position 216; a glutamic acid at the amino acid position corresponding to position 135; a glutamic acid at the amino acid position corresponding to position 536; and a glutamic acid and amino acid position corresponding to position 538 of SEQ ID NO:1.

In embodiments, the polymerase includes a glutamic acid, aspartic acid, alanine, glycine, or threonine at an amino acid position corresponding to position 539 of SEQ ID NO:1. In embodiments, the polymerase includes a glutamic acid at an amino acid position corresponding to position 539 of SEQ ID NO:1. In embodiments, the polymerase includes an aspartic acid at an amino acid position corresponding to position 539 of SEQ ID NO:1. In embodiments, the polymerase includes an alanine at an amino acid position corresponding to position 539 of SEQ ID NO:1. In embodiments, the polymerase includes a glycine at an amino acid position corresponding to position 539 of SEQ ID NO:1. In embodiments, the polymerase includes a threonine at an amino acid position corresponding to position 539 of SEQ ID NO:1. In embodiments, the polymerase includes a glutamic acid, aspartic acid, alanine, glycine, or threonine at an amino acid position corresponding to position 538 and a glutamic acid, aspartic acid, alanine, glycine, or threonine at an amino acid position corresponding to position 539 of SEQ ID NO:1. In embodiments, the polymerase includes a glutamic acid at an amino acid position corresponding to position 538 and a glutamic acid at an amino acid position corresponding to position 539 of SEQ ID NO:1.

In embodiments, the polymerase includes a proline, tryptophan, phenylalanine, tyrosine, alanine, or glycine at the amino acid position corresponding to position 216; a glutamic acid, aspartic acid, alanine, or glycine at an amino acid position corresponding to position 135; a glutamic acid, aspartic acid, alanine, glycine, or threonine at an amino acid position corresponding to position 536; and glutamic acid, aspartic acid, alanine, glycine, or threonine at amino acid position corresponding to position 539 of SEQ ID NO:1. In embodiments, the polymerase includes a proline at an amino acid position corresponding to position 216; a glutamic acid or aspartic acid at the amino acid position corresponding to position 135; a glutamic acid or aspartic acid at the amino acid position corresponding to position 536; and a glutamic acid and amino acid position corresponding to position 539 of SEQ ID NO:1. In embodiments, the polymerase includes a proline at the amino acid position corresponding to position 216; a glutamic acid at the amino acid position corresponding to position 135; a glutamic acid at the amino acid position corresponding to position 536; and a glutamic acid and amino acid position corresponding to position 539 of SEQ ID NO:1.

In embodiments, the polymerase includes a proline, tryptophan, phenylalanine, tyrosine, alanine, or glycine at the amino acid position corresponding to position 216; glutamic acid, aspartic acid, alanine, glycine, or threonine at an amino acid position corresponding to position 131; a glutamic acid, aspartic acid, alanine, or glycine at an amino acid position corresponding to position 135; a glutamic acid, aspartic acid, alanine, glycine, or threonine at an amino acid position corresponding to position 536; and glutamic acid, aspartic acid, alanine, glycine, or threonine at amino acid position corresponding to position 539 of SEQ ID NO:1. In embodiments, the polymerase includes a proline at an amino acid position corresponding to position 216; a glutamic acid or aspartic acid at the amino acid position corresponding to position 131; a glutamic acid or aspartic acid at the amino acid position corresponding to position 135; a glutamic acid or aspartic acid at the amino acid position corresponding to position 536; and a glutamic acid and amino acid position corresponding to position 539 of SEQ ID NO:1. In embodiments, the polymerase includes a proline at the amino acid position corresponding to position 216; a glutamic acid at the amino acid position corresponding to position 131; a glutamic acid at the amino acid position corresponding to position 135; a glutamic acid at the amino acid position corresponding to position 536; and a glutamic acid and amino acid position corresponding to position 539 of SEQ ID NO:1.

In embodiments, the polymerase includes a glutamic acid, aspartic acid, alanine, glycine, or threonine at an amino acid position corresponding to position 131 of SEQ ID NO:1. In embodiments, the polymerase includes a glutamic acid at an amino acid position corresponding to position 131 of SEQ ID NO:1. In embodiments, the polymerase includes an aspartic acid at an amino acid position corresponding to position 131 of SEQ ID NO:1. In embodiments, the polymerase includes an alanine at an amino acid position corresponding to position 131 of SEQ ID NO:1. In embodiments, the polymerase includes a glycine at an amino acid position corresponding to position 131 of SEQ ID NO:1. In embodiments, the polymerase includes a threonine at an amino acid position corresponding to position 131 of SEQ ID NO:1.

In embodiments, the polymerase includes a proline, tryptophan, phenylalanine, tyrosine, alanine, or glycine at the amino acid position corresponding to position 216; a glutamic acid, aspartic acid, alanine, or glycine at an amino acid position corresponding to position 135; a glutamic acid, aspartic acid, alanine, glycine, or threonine at an amino acid position corresponding to position 536; and a glutamic acid and amino acid position corresponding to position 131 of SEQ ID NO:1. In embodiments, the polymerase includes a proline at an amino acid position corresponding to position 216; a glutamic acid or aspartic acid at the amino acid position corresponding to position 135; a glutamic acid or aspartic acid at the amino acid position corresponding to position 536; and a glutamic acid and amino acid position corresponding to position 131 of SEQ ID NO:1. In embodiments, the polymerase includes a proline at the amino acid position corresponding to position 216; a glutamic acid at the amino acid position corresponding to position 135; a glutamic acid at the amino acid position corresponding to position 536; and a glutamic acid and amino acid position corresponding to position 131 of SEQ ID NO:1.

In embodiments, the polymerase includes a glutamic acid, aspartic acid, alanine, glycine, or threonine at an amino acid position corresponding to position 132 of SEQ ID NO:1. In embodiments, the polymerase includes a glutamic acid at an amino acid position corresponding to position 132 of SEQ ID NO:1. In embodiments, the polymerase includes an aspartic acid at an amino acid position corresponding to position 132 of SEQ ID NO:1. In embodiments, the polymerase includes an alanine at an amino acid position corresponding to position 132 of SEQ ID NO:1. In embodiments, the polymerase includes a glycine at an amino acid position corresponding to position 132 of SEQ ID NO:1. In embodiments, the polymerase includes a threonine at an amino acid position corresponding to position 132 of SEQ ID NO:1.

In embodiments, the polymerase includes a proline, tryptophan, phenylalanine, tyrosine, alanine, or glycine at the amino acid position corresponding to position 216; a glutamic acid, aspartic acid, alanine, or glycine at an amino acid position corresponding to position 135; a glutamic acid, aspartic acid, alanine, glycine, or threonine at an amino acid position corresponding to position 536; and a glutamic acid and amino acid position corresponding to position 132 of SEQ ID NO:1. In embodiments, the polymerase includes a proline at an amino acid position corresponding to position 216; a glutamic acid or aspartic acid at the amino acid position corresponding to position 135; a glutamic acid or aspartic acid at the amino acid position corresponding to position 536; and a glutamic acid and amino acid position corresponding to position 132 of SEQ ID NO:1. In embodiments, the polymerase includes a proline at the amino acid position corresponding to position 216; a glutamic acid at the amino acid position corresponding to position 135; a glutamic acid at the amino acid position corresponding to position 536; and a glutamic acid and amino acid position corresponding to position 132 of SEQ ID NO:1.

In an aspect is provided a polymerase including an amino acid sequence that is at least 80% identical to SEQ ID NO: 1; including an arginine, lysine, asparagine, glutamine, alanine, or glycine at an amino acid position corresponding to position 417 of SEQ ID NO:1. In embodiments, the polymerase includes an arginine at the amino acid position corresponding to position 417 of SEQ ID NO:1. In embodiments, the polymerase includes a lysine at the amino acid position corresponding to position 417 of SEQ ID NO:1. In embodiments, the polymerase includes an asparagine at the amino acid position corresponding to position 417 of SEQ ID NO:1. In embodiments, the polymerase includes a glutamine at the amino acid position corresponding to position 417 of SEQ ID NO:1. In embodiments, the polymerase includes an alanine at the amino acid position corresponding to position 417 of SEQ ID NO:1. In embodiments, the polymerase includes a glycine at the amino acid position corresponding to position 417 of SEQ ID NO:1. In embodiments, the polymerase includes an amino acid sequence that is at least 85% identical to SEQ ID NO: 1.

In an aspect is provided a polymerase including an amino acid sequence that is at least 85% identical to SEQ ID NO: 1; including a valine, lysine, asparagine, glutamine, alanine, or glycine at an amino acid position corresponding to position 394 of SEQ ID NO:1. In embodiments, the polymerase includes a valine at the amino acid position corresponding to position 394 of SEQ ID NO:1. In embodiments, the polymerase includes a lysine at the amino acid position corresponding to position 394 of SEQ ID NO:1. In embodiments, the polymerase includes an asparagine at the amino acid position corresponding to position 394 of SEQ ID NO:1. In embodiments, the polymerase includes a glutamine at the amino acid position corresponding to position 394 of SEQ ID NO:1. In embodiments, the polymerase includes an alanine at the amino acid position corresponding to position 394 of SEQ ID NO:1. In embodiments, the polymerase includes a glycine at the amino acid position corresponding to position 394 of SEQ ID NO:1.

In embodiments, the polymerase is a polymerase as described in Table 3. In embodiments, the polymerase is MS-36, having the mutations as described in Table 3. In embodiments, the polymerase is MS-37, having the mutations as described in Table 3. In embodiments, the polymerase is MS-43, having the mutations as described in Table 3. In embodiments, the polymerase is MS-45, having the mutations as described in Table 3. In embodiments, the polymerase is MS-46, having the mutations as described in Table 3. In embodiments, the polymerase is MS-52, having the mutations as described in Table 3. In embodiments, the polymerase is MS-53, having the mutations as described in Table 3. In embodiments, the polymerase is MS-54, having the mutations as described in Table 3. In embodiments, the polymerase is MS-55, having the mutations as described in Table 3. In embodiments, the polymerase is MS-58, having the mutations as described in Table 3. In embodiments, the polymerase is MS-59, having the mutations as described in Table 3. In embodiments, the polymerase is MS-103, having the mutations as described in Table 3. In embodiments, the polymerase is MS-207, having the mutations as described in Table 3. In embodiments, the polymerase is MS-209, having the mutations as described in Table 3. In embodiments, the polymerase is MS-210, having the mutations as described in Table 3. In embodiments, the polymerase is MS-211, having the mutations as described in Table 3. In embodiments, the polymerase is MS-216, having the mutations as described in Table 3.

In embodiments, the polymerase is a recombinant DNA polymerase. In embodiments, the recombinant DNA polymerase is homologous to a Φ29 DNA polymerase or mutant thereof, a Taq polymerase, an exonuclease deficient Taq polymerase, a DNA Pol I polymerase, a T7 polymerase, an RB69 polymerase, a T5 polymerase, or a polymerase corresponding to a Klenow fragment of a DNA Pol I polymerase. For example, the recombinant DNA polymerase can be homologous to a wild-type or exonuclease deficient Φ29 DNA polymerase, e.g., as described in U.S. Pat. Nos. 5,001,050, 5,198,543, or 5,576,204. Similarly, the recombinant DNA polymerase can be homologous to Φ29, B103, GA-1, PZA, Φ15, BS32, M2Y, Nf, G1, Cp-1, PRD1, PZE, SFS, Cp-5, Cp-7, PR4, PR5, PR722, or L17, or the like. For nomenclature, see also, Meijer et al. (2001) "Φ29 Family of Phages" Microbiology and Molecular Biology Reviews, 65(2):261-287, which is incorporated herein by reference for all purposes.

In embodiments, the composition includes a plurality of native DNA nucleotides including a plurality of dATP (2'-deoxyadenosine-5'-triphosphate) nucleotides, dCTP (2'-deoxycytidine-5'-triphosphate) nucleotides, dTTP (2'-deoxythymidine-5'-triphosphate) nucleotides, and dGTP (2'-deoxyguanosine-5'-triphosphate) nucleotides. In embodiments, the composition includes a plurality of dATP (2'-deoxyadenosine-5'-triphosphate) nucleotides, dCTP (2'-deoxycytidine-5'-triphosphate) nucleotides, dTTP (2'-deoxythymidine-5'-triphosphate) nucleotides, and dGTP (2'-deoxyguanosine-5'-triphosphate) nucleotides. In embodiments, the composition includes a plurality of native DNA nucleotides including a plurality of dATP nucleotides, dCTP nucleotides, dTTP nucleotides, or dGTP nucleotides. In embodiments, the composition includes a plurality of dATP nucleotides, dCTP nucleotides, dTTP nucleotides, or dGTP nucleotides. In embodiments, the composition includes a plurality of dATP nucleotides. In embodiments, the composition includes a plurality of dCTP nucleotides. In embodiments, the composition includes a plurality of dTTP nucleotides. In embodiments, the composition includes a plurality of dGTP nucleotides. In embodiments, the composition includes a plurality of dUTP (2'-deoxycytidine-5'-triphosphate) nucleotides. In embodiments, the composition consists of a plurality of dA nucleotides, a plurality of dC nucleotides, a plurality of dT nucleotides, and a plurality of dG nucleotides. In embodiments, the composition consists of a plurality of dA nucleotides, a plurality of dC nucleotides, a plurality of dT nucleotides, a plurality of dU nucleotides, and a plurality of dG nucleotides.

In embodiments, the composition includes a plurality of native RNA nucleotides (i.e., native ribonucleotides) including a plurality of ATP (adenosine-5'-triphosphate) nucleotides, CTP (cytidine-5'-triphosphate) nucleotides, UTP (uridine-5'-triphosphate) nucleotides, and GTP (guanosine-5'-triphosphate) nucleotides. In embodiments, the composition includes a plurality of native RNA nucleotides including a plurality of ATP nucleotides, CTP nucleotides, UTP nucleotides, or GTP nucleotides. In embodiments, the composition includes a plurality of ATP nucleotides. In embodiments, the composition includes a plurality of CTP nucleotides. In embodiments, the composition includes a plurality of UTP nucleotides. In embodiments, the composition includes a plurality of GTP nucleotides. In embodiments, the composition consists of a plurality of A ribonucleotides, a plurality of C ribonucleotides, a plurality of U ribonucleotides, and a plurality of G ribonucleotides.

In embodiments, the composition includes a plurality of cleavable site nucleotides. The term "cleavable site nucleotide" refers to a nucleotide that allows for controlled cleavage of the polynucleotide strand following contact with a cleaving agent (e.g., uracil DNA glycosylase (UDG)). Additional examples of cleavable site nucleotides include deoxyuracil triphosphates (dUTPs), deoxy-8-oxo-guanine triphosphates (d-8-oxoGs), methylated nucleotides, or ribonucleotides. In embodiments, the cleavable site nucleotide is dUTP and the cleaving agent is UDG. In embodiments, the cleavable site nucleotide is a ribonucleotide and the cleaving agent is RNase. In embodiments, the cleavable site nucleotide is 8-oxo-7,8-dihydroguanine (8oxoG) and the cleaving agent is formamidopyrimidine DNA glycosylase (Fpg). In embodiments, the cleavable site nucleotide is 5-methylcytosine and the cleaving agent is McrBC.

In embodiments, the cleavable site includes one or more deoxyuracil triphosphates (dUTPs), deoxy-8-oxo-guanine triphosphates (d-8-oxoGs), methylated nucleotides, or ribonucleotides. In embodiments, the cleavable site includes one or more deoxyuracil triphosphates (dUTPs). In embodiments, the cleavable site includes one or more deoxy-8-oxo-guanine triphosphates (d-8-oxoGs). In embodiments, the cleavable site includes one or more methylated nucleotides. In embodiments, the cleavable site includes one or more ribonucleotides. The one or more cleavable sites may include a modified nucleotide, ribonucleotide, or a sequence containing a modified or unmodified nucleotide that is specifically recognized by a cleavage agent. The cleavable site(s) may be deoxyuracil triphosphate (dUTP), deoxy-8-Oxo-guanine triphosphate (d-8-oxoG), or other modified nucleotide(s), such as those described, for example, in US 2012/0238738, which is incorporated herein by reference for all purposes, and include modified ribonucleotides and deoxyribonucleotides including abasic sugar phosphates, inosine, deoxyinosine, 2,6-diamino-4-hydroxy-5-formamidopyrimidine (foramidopyrimidine-guanine, (fapy)-guanine), 8-oxoadenine, 1,N6-ethenoadenine, 3-methyladenine, 4,6-diamino-5-formamidopyrimidine, 5,6-dihydrothymine, 5,6-dihydroxyuracil, 5-formyluracil, 5-hydroxy-5-methylhydanton, 5-hydroxycytosine, 5-hydroxymethylcystosine, 5-hydroxymethyluracil, 5-hydroxyuracil, 6-hydroxy-5,6-dihydrothymine, 6-methyladenine, 7,8-dihydro-8-oxoguanine (8-oxoguanine), 7-methylguanine, aflatoxin B1-fapy-guanine, fapy-adenine, hypoxanthine, methyl-fapy-guanine, methyltartonylurea and thymine glycol. In embodiments, the cleavable site includes an abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent. In embodiments, the cleavable site includes one or more ribonucleotides. In embodiments, the cleavable site includes 2 to 5 ribonucleotides. In embodiments, the cleavable site includes one ribonucleotide. In embodiments, the cleavable sites can be cleaved at or near a modified nucleotide or bond by enzymes or chemical reagents, collectively referred to here and in the claims as "cleaving agents." Examples of cleaving agents include DNA repair enzymes, glycosylases, DNA cleaving endonucleases, or ribonucleases. For example, cleavage at dUTP may be achieved using uracil DNA glycosylase and endonuclease VIII (USER™, NEB, Ipswich, Mass.), as described in U.S. Pat. No. 7,435,572. In embodiments, when the modified nucleotide is a ribonucleotide, the cleavable site can be cleaved with an endoribonuclease. In embodiments, cleaving an extension product includes contacting the cleavable site with a cleaving agent, wherein the cleaving agent includes a reducing agent, sodium periodate, RNase, formamidopyrimidine DNA glycosylase (Fpg), endonuclease, restriction enzyme, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNase (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C.

In an aspect is provided a kit. In embodiments, the kit includes a polymerase as described herein. In embodiments, the kit includes the reagents and containers useful for performing the methods as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, for example, deoxyribonucleotides, ribonucleotides, and/or modified nucleotides), buffers, salts, and/or labels (e.g., fluorophores).

In embodiments, the kit includes a solid support (i.e., a substrate), and reagents for sample preparation and purification, amplification, and/or sequencing (e.g., one or more sequencing reaction mixtures). In embodiments, amplification reagents and other reagents may be provided in lyophilized form. In embodiments, amplification reagents and other reagents may be provided in a container which the lyophilized reagent may be reconstituted.

In embodiments, the kit includes components useful for circularizing template polynucleotides using a ligation enzyme (e.g., CircLigase™ enzyme, Taq DNA Ligase, HiFi Taq DNA Ligase, T4 ligase, SplintR® ligase, or Ampligase® DNA Ligase). For example, such a kit further includes the following components: (a) reaction buffer for controlling pH and providing an optimized salt composition for a ligation enzyme (e.g., CircLigase™ enzyme, Taq DNA Ligase, HiFi Taq DNA Ligase, T4 ligase, SplintR® ligase, or Ampligase® DNA Ligase), and (b) ligation enzyme cofactors. In embodiments, the kit further includes instructions for use thereof. CircLigase™ and Ampligase® are trademarks of Epicentre. SplintR® is a registered trademark of NEB.

In embodiments, kits described herein include a polymerase. In embodiments, the polymerase is a DNA polymerase. In embodiments, the kit includes a strand-displacing polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a strand-displacing polymerase, such as a polymerase as described herein.

In embodiments, the kit includes a sequencing solution, hybridization solution, and/or extension solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can include one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffered solution can contain one or more divalent cations at a concentration sufficient to permit hybridization of a nucleic acid. In some embodiments, a concentration can be more than about 1 μM, more than about 2 μM, more than about 5 μM, more than about 10 μM, more than about 25 μM, more than about 50 μM, more than about 75 μM, more than about 100 μM, more than about 200 μM, more than about 300 μM, more than about 400 μM, more than about 500 M, more than about 750 μM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1 M. In embodiments, the buffered solution includes about 10 mM Tris, about 20 mM Tris, about 30 mM Tris, about 40 mM Tris, or about 50 mM Tris. In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.05 mM EDTA, about 0.1 mM EDTA, about 0.25 mM EDTA, about 0.5 mM EDTA, about 1.0 mM EDTA, about 1.5 mM EDTA or about 2.0 mM EDTA. In embodiments, the buffered solution includes about 0.01% Triton™ X-100, about 0.025% Triton™ X-100, about 0.05% Triton™ X-100, about 0.1% Triton™ X-100, or about 0.5% Triton™ X-100. In embodiments, the buffered solution includes 20 mM Tris pH 8.0, 100 mM NaCl, 0.1 mM EDTA, 0.025% Triton™ X-100. In embodiments, the buffered solution includes 20 mM Tris pH 8.0, 150 mM NaCl, 0.1 mM EDTA, 0.025% Triton™ X-100. In embodiments, the buffered solution includes 20 mM Tris pH 8.0, 300 mM NaCl, 0.1 mM EDTA, 0.025% Triton™ X-100. In embodiments, the buffered solution includes 20 mM Tris pH 8.0, 400 mM NaCl, 0.1 mM EDTA, 0.025% Triton™ X-100. In embodiments, the buffered solution includes 20 mM Tris pH 8.0, 500 mM NaCl, 0.1 mM EDTA, 0.025% Triton™ X-100. Triton™ is a registered trademark of Dow Chemical Company.

In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

III. Methods

In an aspect is provided a method of incorporating a nucleotide into a primed nucleic acid template (e.g., a primer hybridized to a template nucleic acid). In embodiments, the method includes combining in a reaction vessel: (i) a primer hybridized to a nucleic acid template, (ii) a nucleotide solution including a plurality of nucleotides, and (iii) a polymerase, wherein the polymerase is a polymerase as described herein.

In embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the template polynucleotide includes double-stranded DNA. In embodiments, the method of forming the template polynucleotide includes ligating a hairpin adapter to an end of a linear polynucleotide. In embodiments, the method of forming the template polynucleotide includes ligating hairpin adapters to both ends of the linear polynucleotide. In embodiments, the method of forming the template polynucleotide includes ligating a Y-shaped adapter to an end of a linear polynucleotide. In embodiments, the method of forming the template polynucleotide includes ligating a Y-shaped adapter to both ends of a linear polynucleotide.

In embodiments, the template polynucleotide is about 100 to 1000 nucleotides in length. In embodiments, the template polynucleotide is about 350 nucleotides in length. In embodiments, the template polynucleotide is about 10, 20, 50, 100, 150, 200, 300, or 500 nucleotides in length. The template polynucleotide molecules can vary length, such as about 100-300 nucleotides long, about 300-500 nucleotides long, or about 500-1000 nucleotides long. In embodiments, the template polynucleotide molecular is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the template polynucleotide molecule is about 150 nucleotides. In embodiments, the template polynucleotide is about 100-1000 nucleotides long. In embodiments, the template polynucleotide is about 100-300 nucleotides long. In embodiments, the template polynucleotide is about 300-500 nucleotides long. In embodiments, the template polynucleotide is about 500-1000 nucleotides long. In embodiments, the template polynucleotide molecule is about 100 nucleotides. In embodiments, the template polynucleotide molecule is about 300 nucleotides. In embodiments, the template polynucleotide molecule is about 500 nucleotides. In embodiments, the template polynucleotide molecule is about 1000 nucleotides.

In embodiments the template polynucleotide (e.g., genomic template DNA) is first treated to form single-stranded linear fragments (e.g., ranging in length from about 50 to about 600 nucleotides). Treatment typically entails fragmentation, such as by chemical fragmentation, enzymatic fragmentation, or mechanical fragmentation, followed by denaturation to produce single-stranded DNA fragments. In embodiments, the template polynucleotide includes an adapter. The adaptor may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the primer includes a barcode that is 10-50, 20-30, or 4-12 nucleotides in length. In embodiments, the adapter includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments, the template polynucleotide is single-stranded DNA, double-stranded DNA, single-stranded RNA, or double-stranded RNA. In embodiments, the template is single-stranded DNA or single-stranded RNA and is about 10, 20, 50, 100, 150, 200, 300, 500, or 1000 nucleotides in length. In embodiments, the template polynucleotide is double-stranded DNA or double-stranded RNA and is about 10, 20, 50, 100, 150, 200, 300, 500, or 1000 base pairs in length. In embodiments, the template polynucleotide includes single-stranded circular DNA. In embodiments, the template polynucleotide is single-stranded circular DNA. In embodiments, the template polynucleotide includes double-stranded DNA. In embodiments, the template polynucleotide is double-stranded DNA. In embodiments, the template polynucleotide includes single-stranded RNA. In embodiments, the template polynucleotide is single-stranded RNA. In embodiments, the template polynucleotide includes double-stranded RNA. In embodiments, the template polynucleotide is double-stranded RNA. In embodiments, the template polynucleotide includes primer binding sequences that are complementary to one or more substrate-bound primers. In embodiments, the substrate-bound primers are immobilized to a substrate by a covalent linker. In embodiments, the substrate-bound primers are immobilized to a solid support at the 5' end, preferably via a covalent attachment. In embodiments, the template polynucleotide includes primer binding sequences that are complementary to one or more immobilized primers. In embodiments, the immobilized primers are immobilized to a matrix (e.g., a matrix in a cell) by a covalent linker. In embodiments, the immobilized primers are attached to a matrix at the 5' end, preferably via a covalent attachment. In embodiments, at least some of the substrate-bound primers are phosphorothioated primers. In embodiments, a fraction of the total of the substrate-bound primers are phosphorothioated primers. In embodiments, at least some of the immobilized primers are phosphorothioated primers. In embodiments, a fraction of the total of the immobilized primers are phosphorothioated primers.

In another aspect is provided a method of amplifying a nucleic acid sequence, the method including hybridizing a nucleic acid template to a primer to form a primer-template hybridization complex; contacting the primer-template hybridization complex with a DNA polymerase and a plurality of nucleotides, wherein the DNA polymerase is the polymerase is as described herein; and subjecting the primer-template hybridization complex to conditions which enable the polymerase to incorporate one or more nucleotides into the primer-template hybridization complex to generate amplification products, thereby amplifying a nucleic acid sequence.

In embodiments, the nucleic acid template is DNA, RNA, or analogs thereof. In embodiments, the nucleic acid template includes a primer hybridized to the template. In embodiments, the nucleic acid template is a primer. Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkaline conditions, followed by neutralization. Thus, a "primer" is complementary to a nucleic acid template, and complexes by hydrogen bonding or hybridization with the template to give a primer/template complex for initiation of synthesis by a polymerase, which is extended by the addition of covalently bonded bases linked at their 3' end complementary to the template in the process of DNA synthesis. The DNA template for an amplification reaction will typically include a double-stranded region having a free 3' hydroxyl group which serves as a primer or initiation point for the addition of further nucleotides in the reaction. In embodiments, the primer is hybridized to a polynucleotide in suitable hybridization conditions (e.g., saline-sodium citrate (SSC) buffer (pH 7.0), which is commonly used in nucleic acid hybridization techniques at concentrations from 0.1× to 20×). For example, hybridization may occur in the presence of an hybridization solution as described herein. For example, the hybridization solution may include 40% (v/v) formamide, 5×SSC, 5×Denhardt's solution, 0.1% (w/v) SDS, and dextran sulfate. In embodiments, the hybridization solution includes a buffered solution including salts (e.g., NaCl or KCl), a surfactant (e.g., Triton™ X-100 or Tween®-20), and, optionally, a chelator. In embodiments, the hybridization solution has a pH of about 7.5, 8.0, 8.2, 8.4, 8.6, 8.8, or 9.0. In embodiments, the hybridization solution includes NaCl or KCl, Tris (e.g., pH 8.0), Triton™ X-100, and a chelator (e.g., EDTA). In embodiments, the hybridization solution includes NaCl, Tris (e.g., pH 8.5), Triton™ X-100, and a chelator (e.g., EDTA). In embodiments, the hybridization solution includes NaCl, Tris (e.g., pH 8.8), Triton™ X-100, and a chelator (e.g., EDTA). In embodiments, the hybridization solution includes NaCl, Tris (e.g., pH 8.5), Tween®-20, and a chelator (e.g., EDTA). In embodiments, the hybridization solution includes NaCl, Tris (e.g., pH 8.8), Tween®-20, and a chelator (e.g., EDTA). In embodiments, the hybridization solution includes 3 M NaCl, 0.1 M Tris-HCl (pH 6.8), 0.1 M $NaPO_4$ buffer (pH 6.8), and 50 mM EDTA. In embodiments, the hybridization solution includes formamide. In embodiments, the hybridization solution includes dextran sulfate. In embodiments, the hybridization solution includes 140 mM HEPES, pH 8.0, containing 1% SDS, 1.7 M NaCl, 7×Denhardt's solution, 0.2 mM EDTA, and 3% PEG. In embodiments, the hybridization solution includes acetonitrile at 25-50% by volume, formamide at 5-10% by volume; 2-(N-morpholino)ethanesulfonic acid (MES); and polyethylene glycol (PEG) at 5-35%. In some embodiments, the hybridization solution further includes betaine.

In embodiments, extending is performed in the presence of an extension solution. In embodiments, the extension solution includes a buffered solution including salts (e.g., NaCl or KCl), a surfactant (e.g., Triton™ X-100 or Tween®-20), and a chelator. In embodiments, the extension solution includes nucleotides and a polymerase (e.g., a polymerase as described herein). In embodiments, the polymerase is a strand-displacing polymerase as described herein. In embodiments, the extension solution includes about 0.5, about 1, about 2, about 3, about 4, about 5, about 6, about 7, about 8, about 9, about 10, about 11, about 12, about 13, about 14, or about 15 mM $Mg^{2+}$. In embodiments, the extension solution includes a dNTP mixture including dATP, dCTP, dGTP and dTTP (for DNA amplification) or dATP, dCTP, dGTP and dUTP (for RNA amplification). In embodiments, the extension solution has a pH of about 7.5, 8.0, 8.2, 8.4, 8.6, 8.8, or 9.0. In embodiments, the extension solution includes Tris-HCl (e.g., pH 8.0), salt (e.g, NaCl or KCl), $MgSO_4$, a surfactant (e.g., Tween®-20 or Triton™ X-100), dNTPs, BstLF, betaine (e.g., between about 0 to about 3.5M betaine), and/or DMSO (e.g., between about 0% to about 12% DMSO). In embodiments, the extension solution includes bicine (e.g., pH 8.5), salt (e.g., NaCl or KCl), $MgSO_4$, a surfactant (e.g., Tween-20 or Triton X-100), dNTPs, BstLF, (e.g., between about 0 to about 3.5M betaine), and/or DMSO (e.g., between about 0% to about 12% DMSO).

In embodiments, the hybridization solution and/or the extension solution includes a buffer such as, phosphate buffered saline (PBS), succinate, citrate, histidine, acetate, Tris, TAPS, MOPS, PIPES, HEPES, MES, and the like. The choice of appropriate buffer will generally be dependent on the target pH of the hybridization solution and/or the extension solution. In general, the desired pH of the buffer solution will range from about pH 4 to about pH 8.4. In some embodiments, the buffer pH may be at least 4.0, at least 4.5, at least 5.0, at least 5.5, at least 6.0, at least 6.2, at least 6.4, at least 6.6, at least 6.8, at least 7.0, at least 7.2, at least 7.4, at least 7.6, at least 7.8, at least 8.0, at least 8.2, or at least 8.4. In some embodiments, the buffer pH may be at most 8.4, at most 8.2, at most 8.0, at most 7.8, at most 7.6, at most 7.4, at most 7.2, at most 7.0, at most 6.8, at most 6.6, at most 6.4, at most 6.2, at most 6.0, at most 5.5, at most 5.0, at most 4.5, or at most 4.0. Any of the lower and upper values described in this paragraph may be combined to form a range included within the present disclosure, for example, in some instances, the desired pH may range from about 6.4 to about 7.2. Those of skill in the art will recognize that the buffer pH may have any value within this range, for example, about 7.25.

Suitable detergents for use in the hybridization solution and/or the extension solution include, but are not limited to, zwitterionic detergents (e.g., 1-Dodecanoyl-sn-glycero-3-phosphocholine, 3-(4-tert-Butyl-1-pyridinio)-1-propanesulfonate, 3-(N,N-Dimethylmyristylammonio)propanesulfonate, 3-(N,NDimethylmyristylammonio) propanesulfonate, ASB-C80, C7BzO, CHAPS, CHAPS hydrate, CHAPSO, DDMAB, Dimethylethylammonium-propane sulfonate, N,N-Dimethyldodecylamine Noxide, N-Dodecyl-N,N-dimethyl-3-ammonio-1-propanesulfonate, or N-Dodecyl-N,N-dimethyl-3-ammonio-1-propanesulfonate) and anionic, cationic, and non-ionic detergents. Examples of nonionic detergents include poly(oxyethylene) ethers and related polymers (e.g. Brij®, TWEEN®, TWEEN®-20, TRITON™, TRITON™ X-100 and IGEPAL® CA-630), bile salts, and glycosidic detergents. In embodiments, the hybridization solution and/or the extension solution include antioxidants and reducing agents, carbohydrates, BSA, polyethylene glycol, dextran sulfate, betaine, other additives.

In embodiments, the method includes amplifying the polynucleotide via an isothermal amplification process. Isothermal amplification processes include rolling-circle amplification (RCA), strand displacement amplification (SDA), loop-mediated isothermal amplification (LAMP), smart amplification process (SMAP), isothermal and chimeric primer-initiated amplification (ICAN), and simple method for amplifying RNA targets (SMART). In these techniques, the extension reaction proceeds at a constant temperature, for example using strand displacement reactions. Amplification can be completed in a single step, by incubating the mixture of samples, primers, DNA polymerase with strand displacement activity, and substrates at a constant temperature (e.g., about 25° C. to about 40° C.). This reduces the number of steps required, eliminating thermal ramping steps and reducing the total cycle time for each amplification cycle, while simultaneously decreasing the reaction time required for each cycle. In embodiments, the method includes an amplification technique capable of amplifying a circular template polynucleotide. In embodiments, the method includes exponential rolling circle amplification (eRCA). Exponential RCA is similar to the linear process except that it uses a second primer having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5(1994)). In embodiments, the method includes hyberbranched rolling circle amplification (HRCA). Hyperbranched RCA uses a second primer complementary to the first amplification product. This allows products to be replicated by a strand-displacement mechanism, which can yield a drastic amplification within an isothermal reaction (Lage et al., Genome Research 13:294-307 (2003), which is incorporated herein by reference in its entirety).

Strand displacement amplification (SDA) relies on a strand displacement DNA polymerase and nicking endonuclease, which are used in repeated nicking and extending steps to generate downstream displacement strands capable of participating in exponential amplification (Walker et al. Nucleic Acids Res. 20:1691-1696 (1992)). Loop-mediated isothermal amplification (LAMP) utilizes DNA polymerase in the presence of four specially designed primers to recognize six distinct sequences of target DNA, which enables the target DNA to be synthesized and displaced to produce a stem-loop DNA structure (Notomi et al. Nucleic Acids Res. 28:e63 (2000)). Smart amplification process (SMAP) is an isothermal nucleic acid amplification method that uses strand displacing Aac DNA polymerase, asymmetrical primers, and mismatch binding protein Taq MutS to amplify target alleles with minimal background amplification (Mitani et al. Nat. Methods. 4:257-62 (2007)). Isothermal and chimeric primer-initiated amplification (ICAN) relies on a pair of 5'-DNA-RNA-3' chimeric primers, thermostable RNaseH and a strand displacing DNA polymerase to amplify target DNA (Uemori et al. J Biochem. 142:283-92 (2007)). Simple method for amplifying RNA targets (SMART) relies on initially capturing target RNA using a target specific primers immobilized to the surface of magnetic beads, followed by hybridizing target RNA sequences to highly specific amplifiable SMART probes to facilitate the reverse transcription of the target RNA to cDNA and amplification of the target templates (McCalla et al. J Mol Diagn. 14: 328-335 (2012)). In embodiments, the template polynucleotide includes single-stranded circular DNA. In embodiments, the template polynucleotide is single-stranded circular DNA. In embodiments, the template polynucleotide includes double-stranded DNA. In embodiments, the template polynucleotide is double-stranded DNA. In embodiments, the template polynucleotide includes single stranded RNA. In embodiments, the template polynucleotide is single stranded RNA. In embodiments, the template polynucleotide includes double stranded RNA. In embodiments, the template polynucleotide is double stranded RNA. In embodiments, the method further includes forming the template polynucleotide by ligating ends of a linear polynucleotide (e.g., a single stranded polynucleotide) together to form a circular template polynucleotide. In embodiments, the method further includes forming the template polynucleotide by ligating a hairpin adapter to an end of a linear polynucleotide. In embodiments, the method includes forming the template polynucleotide includes ligating hairpin adapters to both ends of the linear polynucleotide thereby forming a circular template polynucleotide. In embodiments, the template polynucleotide is single-stranded circular DNA. Methods for forming circular DNA templates are known in the art, for example linear polynucleotides are circularized in a non-template driven reaction with circularizing ligase, such as CircLigase™, Taq DNA Ligase, HiFi Taq DNA Ligase, T4 ligase, or Ampligase® DNA Ligase. In embodiments, the method of forming the template polynucleotide includes ligating ends of a linear polynucleotide together. In embodiments, the two ends of the template polynucleotide are ligated directly together. In embodiments, the two ends of the template polynucleotide are ligated together with the aid of a bridging oligonucleotide (sometimes referred to as a splint oligonucleotide) that is complementary with the two ends of the template polynucleotide. In embodiments, the bridging oligonucleotide contains the amplification primer.

Circular polynucleotides of virtually any sequence can be produced using a variety of techniques (see for example U.S. Pat. No. 5,426,180; Dolinnaya et al. Nucleic Acids Research, 21: 5403-5407 (1993); or Rubin et al. Nucleic Acids Research, 23: 3547-3553 (1995), which are incorporated herein by reference). In embodiments, the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length. In embodiments, the circular polynucleotide is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides in length. In embodiments, the circular polynucleotide molecule is about 100-1000 nucleotides in length. In embodiments, the circular polynucleotide molecule is about 100-300 nucleotides in length. In embodiments, the circular polynucleotide molecule is about 300-500 nucleotides in length. In embodiments, the circular polynucleotide molecule is about 500-1000 nucleotides in length. In embodiments, the circular polynucleotide molecule is about 100 nucleotides. In embodiments, the initial template polynucleotide molecule is about 300 nucleotides. In embodiments, the circular polynucleotide molecule is about 500 nucleotides. In embodiments, the circular polynucleotide molecule is about 1000 nucleotides. Circular polynucleotides may be conveniently isolated by a conventional purification column, digestion of non-circular DNA by one or more appropriate exonucleases, or both.

In embodiments, the template polynucleotide is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length. In embodiments, the circular polynucleotide includes at least one cleavable site. In embodiments, the method includes forming the template polynucleotide. The template polynucleotide can be a circular, dumbbell-shaped, or other closed nucleic acid molecule configuration that does not have a free 3' or 5' end. Typical library preparation steps may be performed on a linear template such that it is circularized (e.g., such as the protocols described in Kershaw, C. J., & O'Keefe, R. T. (2012) 941, 257-269). The initial template polynucleotide molecules can vary length, such as about 100-300 nucleotides long, about 300-500 nucleotides long, or about 500-1000 nucleotides long. In embodiments, the initial template polynucleotide molecular is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the initial template polynucleotide molecule is about 150 nucleotides. In embodiments, the initial template polynucleotide is about 100-1000 nucleotides long. In embodiments, the initial template polynucleotide is about 100-300 nucleotides long. In embodiments, the initial template polynucleotide is about 300-500 nucleotides long. In embodiments, the initial template polynucleotide is about 500-1000 nucleotides long. In embodiments, the initial template polynucleotide molecule is about 100 nucleotides. In embodiments, the initial template polynucleotide molecule is about 300 nucleotides. In embodiments, the initial template polynucleotide molecule is about 500 nucleotides. In embodiments, the initial template polynucleotide molecule is about 1000 nucleotides.

In embodiments, the method includes cycling between a first temperature and a second temperature, wherein the difference between the first temperature and the second temperature is no greater than 20° C. In embodiments, the method includes cycling between a first temperature and a second temperature, wherein the difference between the first temperature and the second temperature is no greater than 19° C. In embodiments, the method includes cycling between a first temperature and a second temperature, wherein the difference between the first temperature and the second temperature is no greater than 18° C. In embodiments, the method includes cycling between a first temperature and a second temperature, wherein the difference between the first temperature and the second temperature is no greater than 16° C. In embodiments, the method includes cycling between a first temperature and a second temperature, wherein the difference between the first temperature and the second temperature is 10° C. to 18° C. In embodiments, the method includes cycling between a first temperature and a second temperature, wherein the difference between the first temperature and the second temperature is 12° C. to 18° C.

In embodiments, the method includes cycling between a first temperature and a second temperature, wherein the difference between the first temperature and the second temperature is 18° C. In embodiments, the method includes cycling between a first temperature and a second temperature, wherein the difference between the first temperature and the second temperature is 19° C. In embodiments, the method includes cycling between a first temperature and a second temperature, wherein the difference between the first temperature and the second temperature is 1° C. to 19° C. In embodiments, the method includes cycling between a first temperature and a second temperature, wherein the difference between the first temperature and the second temperature is 10° C. to 19° C. In embodiments, the method includes cycling between a first temperature and a second temperature, wherein the difference between the first temperature and the second temperature is 12° C. to 18° C.

In embodiments, extending the amplification primer includes incubation with the polymerase (e.g., a polymerase described herein) in suitable conditions and for a suitable amount of time. In embodiments, the step of extending the amplification primer includes incubation with the polymerase (i) for about 10 seconds to about 30 minutes, and/or (ii) at a temperature of about 20° C. to about 50° C. In embodiments, incubation with the polymerase is for about 0.5 minutes to about 16 minutes. In embodiments, incubation with the polymerase is for about 0.5 minutes to about 10 minutes. In embodiments, incubation with the polymerase is for about 1 minutes to about 5 minutes. In embodiments, the method includes amplifying a template polynucleotide by extending an amplification primer with a polymerase for about 10 seconds to about 30 minutes. In embodiments, the method includes amplifying a template polynucleotide by extending an amplification primer with a polymerase for about 30 seconds to about 16 minutes. In embodiments, the method includes amplifying a template polynucleotide by extending an amplification primer with a polymerase for about 30 seconds to about 10 minutes. In embodiments, the method includes amplifying a template polynucleotide by extending an amplification primer with a polymerase for about 30 seconds to about 5 minutes. In embodiments, the method includes amplifying a template polynucleotide by extending an amplification primer with a polymerase for about 1 second to about 5 minutes. In embodiments, the method includes amplifying a template polynucleotide by extending an amplification primer with a polymerase for about 1 second to about 2 minutes.

In embodiments, incubation with the polymerase is at a temperature of about 35° C. to 42° C. In embodiments, incubation with the polymerase is at a temperature of about 37° C. to 40° C. In embodiments, incubation with the thermostable polymerase is at a temperature of about 40° C. to 80° C. In embodiments, the method includes amplifying a template polynucleotide by extending an amplification primer with a polymerase at a temperature of about 20° C. to about 50° C. In embodiments, the method includes amplifying a template polynucleotide by extending an amplification primer with a polymerase at a temperature of about 30° C. to about 50° C. In embodiments, the method includes amplifying a template polynucleotide by extending an amplification primer with a polymerase at a temperature of about 25° C. to about 45° C. In embodiments, the method includes amplifying a template polynucleotide by extending an amplification primer with a polymerase at a temperature of about 35° C. to about 45° C. In embodiments, the method includes amplifying a template polynucleotide by extending an amplification primer with a polymerase at a temperature of about 35° C. to about 42° C. In embodiments, the method includes amplifying a template polynucleotide by extending an amplification primer with a polymerase at a temperature of about 37° C. to about 40° C.

In embodiments, the polymerase is contacted with the amplification primer and template polynucleotide in the absence of dNTPs; optionally, excess polymerase is removed; and amplification buffer with dNTPs is added to initiate amplification. In embodiments, the polymerase is contacted with the amplification primer and template polynucleotide in the absence of dNTPs; and optionally, excess polymerase is removed. In embodiments, the amplification primer is hybridized to the template polynucleotide prior to contact with the polymerase. For example, the amplification primer and template polynucleotide form a complex, and the polymerase subsequently binds to this complex. In embodiments, the polymerase is contacted with the amplification primer and template polynucleotide in the absence of dNTPs and/or $Mg^{2+}$.

In an aspect is provided a method of amplifying a template polynucleotide, the method including: contacting a template polynucleotide with an amplification primer, and amplifying the template polynucleotide by extending an amplification primer with a polymerase to generate an extension product including one or more complements of the template polynucleotide; wherein the polymerase is a polymerase as described herein. In embodiments, the method includes amplifying the circular oligonucleotide by extending an amplification primer hybridized to the circular oligonucleotide with a strand-displacing polymerase (e.g., a polymerase as described herein), wherein the amplification primer extension generates an extension product including multiple complements of the circular oligonucleotide. In embodiments, the method further includes sequencing the circular oligonucleotide. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which are incorporated herein by reference in their entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

In embodiments, sequencing includes sequencing-by-binding (see, e.g., U.S. Pat. Pubs. US2017/0022553 and US2019/0048404, each of which are incorporated herein by reference in their entirety). As used herein, "sequencing-by-binding" refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide. As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by Nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US Patent Publication 2018/0274024, WO 2017/205336, US Patent Publication 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, generating a sequencing read includes determining the identity of the nucleotides in the template polynucleotide (or complement thereof). In embodiments, a sequencing read, e.g., a first sequencing read or a second sequencing read, includes determining the identity of a portion (e.g., 1, 2, 5, 10, 20, 50 nucleotides) of the total template polynucleotide. In embodiments the first sequencing read determines the identity of 5-10 nucleotides and the second sequencing read determines the identity of more than 5-10 nucleotides (e.g., 11 to 200 nucleotides). In embodiments the first sequencing read determines the identity of more than 5-10 nucleotides (e.g., 11 to 200 nucleotides) and the second sequencing read determines the identity of 5-10 nucleotides.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. These such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera or other suitable detection means).

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step. In embodiments, the methods of sequencing a nucleic acid include a sequencing solution. The sequencing solution includes (a) an adenine nucleotide, or analog thereof; (b) (i) a thymine nucleotide, or analog thereof, or (ii) a uracil nucleotide, or analog thereof; (c) a cytosine nucleotide, or analog thereof; and (d) a guanine nucleotide, or analog thereof In embodiments, the method includes amplifying the template polynucleotide in a cell. In embodiments, the method includes amplifying the template polynucleotide in a tissue. In embodiments, the method includes amplifying the template polynucleotide one a solid support (e.g., a multiwell container or a flowcell). In embodiments, the amplification primer is immobilized on a solid support.

In embodiments, the method includes incorporating one or more cleavable sites into the amplification product. For example, in embodiments, the method includes contacting the primed DNA template with a composition including a plurality of native DNA nucleotides and cleavable site nucleotides, thereby forming a plurality of amplification products, wherein the amplification products include a cleavable site nucleotide at a different position relative to each other.

In embodiments, the polymerases described herein have improved polymerase activity (i.e., improved relative to a control). Polymerase activity, in some instances, includes the measurable quantity $k_{cat}$, $k_{cat}/K_m$, or yields of incorporated nucleotides for a given time period. In embodiments, the polymerases described herein have increased extension activity (i.e., increased relative to a control). Increased extension activity variously refers to an increase in reaction kinetics (increased $k_{cat}$), increased $K_D$, decreased $K_m$, increased $k_{cat}/K_m$ ratio, faster turnover rate, higher turnover number, or other metric that is beneficial to the use of the polypeptide for nucleic acid extension with nucleotides. The polypeptides described herein often incorporate at least 30% more nucleotides than the wild-type polymerase in total or in a given duration of time.

In embodiments, the polymerases described herein often incorporate at least 10%, 20%, 30%, 50%, 75%, 100%, 125%, 150%, 200%, 500%, more nucleotides than a control (e.g., the wild-type polymerase) for a fixed amount of time and same nucleotide concentration. In embodiments, the polymerases described herein incorporate nucleotides at least 1.5, 2, 2.5, 5, 10, 15, 20, 25, or at least 50 times faster than a control (e.g., the wild-type polymerase) for a fixed amount of time. Such measurements are often measured under conditions such as a set period of time, such as at least, at most, or exactly 1, 2, 3, 5, 8, 10, 15, 20, or more than 20 minutes. Such measurements are often measured under conditions such as a set nucleotide concentration, such as less than 10 μM, 20 μM, 50 μM, 100 μM, 200 μM, 300 μM, 500 μM, or more than 500 μM, or any concentration within the range identified herein.

In embodiments, the methods described herein further includes detecting the amplification product (e.g., detecting via sequencing method, or for example, by fluorescent detection methods).

EXAMPLES

Example 1. Development of Polymerase Variants

DNA amplification has many applications in molecular biology research and medical diagnostics. There are two main strategies for amplifying a defined sequence of nucleic acid: polymerase chain reaction (PCR) and isothermal amplification. The polymerase chain reaction relies upon thermal cycling to denature dsDNA templates, followed by annealing primers at specific sites in the denatured template, and extension of the primers by a thermostable DNA polymerase. Isothermal amplification of DNA, as the name implies, typically includes amplification of the dsDNA at a defined temperature. The lack of thermal cycling in isothermal amplification technologies reduces equipment needs and improves the time to answer, especially for point-of-care applications.

A variety of isothermal amplification methods have been developed, for example, strand displacement amplification (SDA) (Walker, G. T. et al. Nucleic Acids Res 20, 1691-6 (1992); and Walker, G. T., Little, M. C, Nadeau, J. G. & Shank, D. D. PNAS 89, 392-6 (1992)), rolling circle amplification (RCA) (Fire, A. & Xu, S. Q. PNAS 92, 4641-5 (1995)), cross priming amplification (CPA) (Xu, G. et al. Sci. Rep. 2, 246; (2012)) and loop mediated amplification (LAMP) (Notomi, T. et al. Nucleic Acids Res 28, e63 (2000)). While some isothermal amplification mechanisms depend upon multiple enzymes, e.g., nickases, recombinases, and ligases, to achieve continuous replication, RCA and LAMP require only polymerases (e.g., a polymerase described herein) and primers. These methods, like many other isothermal amplification methods, require the use of a DNA polymerase with a strong strand displacement activity to displace downstream DNA, thereby enabling continuous replication without thermal cycling. Thus, a DNA polymerase suitable for these methods must be a stable DNA polymerase with a strong strand displacement activity.

One such DNA polymerase, Phi29 DNA polymerase, is a monomeric enzyme of 66 kDa, a DNA-dependent enzyme belonging to the eukaryotic-type family of DNA polymerases (family B). Referred to as proofreading, phi29 contains an exonuclease domain that catalyzes 3'→5' exonucleolysis of mismatched nucleotides, thereby enhancing replication fidelity at least 100-fold. Additionally, wild-type phi29 DNA polymerase reliably binds to single stranded DNA, and performs DNA synthesis without processivity cofactors, accounting for the highest known processivity (>70 kb) among other DNA polymerases. Strong processivity, robust strand displacement activity, and high accuracy allow the enzyme to amplify whole genomes with minimal amplification bias compared to PCR based amplification methods.

FIG. 3 provides an alignment of seven sequences described herein. A portion of the entire amino acid sequence is shown, aligning the wild type polymerase (SEQ ID NO:1) to BSTP6 (SEQ ID NO:12), MinWT (SEQ ID NO:2), BSTP4 (SEQ ID NO:8), Whiting18 (SEQ ID NO:17), Phage M2 (SEQ ID NO:20), and Beecentumtrevirus (SEQ ID NO:22). The alignment highlights a negative three (−3) frameshift in amino acid positions of MinWT, BSTP4, Whiting18, Phage M2, and Beecentumtrevirus relative to wild type, wherein the amino acid positions are shifted by three positions. For example, the amino acid position 312 of the wild type sequence corresponds to the amino acid position 309 if BSTP4 (SEQ ID NO:8). Amino acid substitutions relative to the wild type sequence are shaded.

Structural analysis of DNA polymerases portray the enzymes as analogous to a human right hand, with three domains: a 'fingers' domain that interacts with the incoming dNTP and paired template base, and that closes at each nucleotide addition step; a 'palm' domain that catalyzes the phosphoryl-transfer reaction; and a 'thumb' domain that interacts with duplex DNA. Compared with the structure of other family B DNA polymerases, phi29 DNA polymerase shows a common (right hand) fold containing palm, thumb and fingers subdomains. The main structural difference between phi29 DNA polymerase and other family B DNA polymerases is the presence of two additional subdomains, called TPR1 and TPR2, that are insertions between the fingers and palm subdomains. TPR2 helps to form a narrow tunnel around the downstream DNA, forcing separation of the second strand before its entry into polymerase active site. Additionally the palm, thumb, TPR1, and TPR2 subdomains form a doughnut-shaped structure around the upstream duplex product, providing maximal DNA-binding stability which enhances processivity in a manner analogous to sliding-clamp proteins. The unique structure provides high processivity and strand displacement activity, which enables phi29 DNA polymerase to be used in isothermal multiple displacement amplification (MDA) or rolling circle amplification (RCA).

Diagnostics and therapeutic interventions rely on amplification technologies using the phi29 DNA polymerase and have several advantages compared to classical PCR DNA amplification methods. For example, amplification products (e.g., amplicons) synthesized by the phi29 DNA polymerase can be much larger comparing to those obtained by PCR. Additionally, isothermal DNA amplification reactions do not require special laboratory equipment such as thermal cyclers. These advantages make phi29 DNA polymerase suitable for detection and analysis of known and unknown circular viral genomes, replication of pathogenic plasmids, amplification of very small DNA samples, e.g., replication from filter paper samples containing a blood spot, and for in situ transcript and proteomic detection. The ability to perform reactions at increased temperature would be advantageous so that amplification reaction kinetics would be faster. Phi29 DNA polymerase is a typical mesophilic enzyme with an optimal reaction temperature of about 30° C. to about 40° C. Elevated reaction temperatures could improve DNA amplification efficiency and decrease formation of template-independent, non-specific reaction products. The relatively low working temperature of phi29 DNA polymerase limits its application; a more thermostable enzyme could be used in many more DNA amplification techniques, generate more product, work faster, and increase amplification reaction sensitivity.

Attempts to improve phi29 DNA polymerase have been performed by introducing amino acid mutations. For example, exonuclease activity was reduced by introducing an alanine at acid moiety at positions 12, 14, or 16 as described in U.S. Pat. No. 5,198,543, which is incorporated herein by reference. Efforts to reduce the processivity (i.e., increase the amount of time a nucleotide analog resides in the binding pocket of the enzyme) of the polymerase for single molecule applications are described in US Pub. 2008/0108082, which is incorporated herein by reference. Previous attempt to evolve a mesophilic polymerase was described in Povilaitis et al. Protein Engineering, Design & Selection, 2016, vol. 29 no. 12, pp. 617-628). The alternative, that is improving the processivity, i.e., reducing the residence time, and improving strand displacing activity of phi29, without sacrificing the accuracy or stability of phi29 enzymes remains a challenge. Disclosed herein, inter alia, are solutions to these and other problems in the art.

Materials. All reagents and enzymes (DpnI, AlwNI, restriction endonucleases, phi29 DNA polymerase) were purchased from NEB, unless otherwise specified. The oligonucleotides were purchased from Integrated DNA Technologies (IDT). Plasmid pET21b(+)/MS-0 is the wild-type phi29 DNA polymerase expression plasmid, plasmid pET21b(+)/MS-0-Chis contains phi29 DNA polymerase gene fused to the 6×His-tag at the C-terminus of the protein. In general, purification tags may be added to the polymerase (recombinantly or chemically) and include, e.g., polyhistidine tags, $His_6$-tags, biotin, avidin, GST sequences, BTag sequences, S tags, SNAP-tags, enterokinase sites, thrombin sites, antibodies or antibody domains, antibody fragments, antigens, receptors, receptor domains, and/or receptor fragments. Both plasmids were constructed at Singular Genomics Systems, Inc.

DNA manipulation and protein expression. The pET21b (+)/MS-0 (wt) plasmid encoding the wild-type phi29 DNA polymerase was used to transform *E. coli* BL21 STAR™ (DE3)cells (ThermoFisher). The *E. coli* cells carrying expression plasmid were grown at 37° C. until OD600 of 1 was reached. The protein expression was induced by adding IPTG to a final concentration of 1 mM and cells were grown for another 6 h at 30° C. Phi29 DNA polymerase genes containing single mutations were constructed using plasmid pET21b(+)/MS-O-Chis) where the phi29 polymerase gene was fused to the 6×His tag at the C-terminus of the protein.

Library construction. The initial library of genes coding for mutant phi29 DNA polymerases was generated by error-prone PCR using the GeneMorph II kit (Agilent). Mutagenic PCR was performed using epPCR-F (5'-CTT-TAAGAAGGAGATATACAGAATTCATGAAACATA TG*C-3' (SEQ ID NO:53) and epPCR-R (5'-GTTAGCAGCCGGATCTCAGT*G-3' (SEQ ID NO:54) primers, target DNA, and a PCR program with 20 amplification cycles as recommended by the manufacturer. The '*' in the primer sequence is indicative of a phosphorothioate bond between the two nucleotides to be resistant to exonuclease activity. The target DNA (i.e., the parent DNA) was digested using 20 U DpnI restriction enzyme (NEB) for 2 hours at 37° C. After digestion the product was run on an agarose gel and the band of interest was excised and purified using Zymoclean™ Gel DNA Recovery Kit (Zymo Research) followed by an additional purification using a column cleanup kit (Monarch® kit, NEB). The mutagenized error-prone PCR product was assembled with the linearized pET21b(+) vector using Gibson Assembly with 2×HiFi assembly kit (NEB). The insert DNA was combined with vector DNA. The Gibson assembly mix was incubated at 50° C. for 30 minutes and then purified using a column cleanup kit (Monarch® kit, NEB) and eluted into 8 µL. 2 µL eluted DNA was then added to 50 µL T7 electrocompetent cells made in-house and electroporated. Dilutions of $1:10^4$, $1:10^5$, and $1:10^6$ were plated to calculate library size. The transformed T7 cell culture was then miniprepped and the DNA was transformed into electrocompetent BL21 STAR™ (DE3) cells made in-house, with the same dilution series to ensure adequate library size. The library in BL21 cells was preserved in frozen stocks with 15% glycerol and at least $3\times10^8$ cells per vial.

Compartmentalized self-replication (CSR). Directed evolution of enzymes is a process that mimics natural selection in vitro. Compartmentalized self-replication is a method of directed evolution where a library containing mutated variants of the enzyme of interest goes through rounds of selective pressure, and over time, the most active or best performing variants are enriched in the library, compared to less active variants, as described in Abil, Z., & Ellington, A. D. (2018). *Current Protocols in Chemical Biology,* 10, 1-17. During CSR, the enzyme variants and its own encoding genes are compartmentalized in oil emulsions, together with dNTPs and primers. During the emulsion PCR, each enzyme that can surpass the selective pressure is able to replicate its own encoding gene and pass to the next round of selection. Over time, the best performers are enriched in the library. The selection scheme for a faster Phi29 DNAP polymerase was based on the CSR strategy (Ghadessy F J, Ong J L, Holliger P. Directed evolution of polymerase function by compartmentalized self-replication. Proc Natl Acad Sci USA. 2001 Apr. 10; 98(8):4552-7) with some modification.

BL21 STAR™ (DE3) cells transformed with the variant phi29 library were grown for 24 hours in 20 mL MagicMedia™ autoinduction media (ThermoFisher) supplemented with 100 μg/mL ampicillin, at 30° C., inoculated directly with 1 mL frozen stock. After 24 hours growth the cells (100 μL of cells) were lysed and run on an SDS-PAGE gel to ensure protein expression. $5\times10^8$ cells were harvested and washed three times with 500 μL SN-buffer (a buffer including 0.05 M Tris HCl, pH 7.5) before re-suspending in 500 μL buffer. $5\times10^7$ cells were then added to a reaction mix consisting of 1 mM dNTPs, 1 M each of six forward and six reverse primers spanning the pET21b(+) plasmid, hen egg lysozyme, bovine serum albumin, and 1×SN-buffer, which comprised the aqueous phase of the emulsion. 300 μL aqueous phase was added on top of oil phase (mineral oil (Sigma) with 2% ABIL® EM 90 (Glenn Corp.) and 0.055% Triton™ X-100 (Dow Chemical Company)) with a mini-stir bar. The mixture was emulsified by vibrating the tubes in a TissueLyser LT at 42 Hz for 4 min at 4° C. The emulsions were then incubated for 5 minutes at room temperature to allow lysozyme to lyse the cells. The emulsions were incubated at 37° C. on a heating block for variable time periods during the selection, ranging from 2 hours to 0 minutes. After the desired time period the reaction was stopped by incubation at 80° C. for 15 minutes. The aqueous phase was extracted using diethyl ether (Merck) and ethyl acetate (Sigma-Aldrich), as described in Williams et al. (Williams, R. et al. (2006) Nat. Methods, 3, 545-550). After chlorophorm/phenol (Sigma) extraction and ethanol precipitation, reaction products were dissolved in 50 μL of 1× CutSmart® buffer (NEB), 2 μL of DpnI (20 U/μL) and 1 μL AlwNI (10 U/μL) restriction endonucleases to digest methylated parental DNA and to linearize the concatemers generated by RCA. The reaction was incubated for 16 hours at 37° C. followed by enzyme inactivation for 15 minutes at 80° C. Digested DNA was purified using a column purification kit (Monarch® NEB). RCA products were amplified by recovery PCR using primers spanning the entire phi29 coding region of the pET21b(+) vector with the appropriate 5' and 3' overhangs for Gibson assembly. The insert was then gel-purified and transformed back into *E. coli* for a subsequent round of CSR selection.

Additional variants were produced via modeling and rationale design to reduce unproductive binding to single stranded oligonucleotides. For example, MS-207; MS-208; MS-209; MS-210; MS-211; MS-212; MS-213; MS-214; and MS-215 were generated by analyzing the crystal structure of the wild type binding to a single stranded oligonucleotide. It was determined that positively charged K135 in the exonuclease (also referred to as "exo") domain and K536 in the thumb domain are about 12 Å to 18 Å away from the active center (see FIG. 2B), and possibly involved in non-specific binding of DNA oligo by supporting the negatively charged phosphate backbone of the DNA. This region has a relatively higher density of positively charged amino acids (e.g., K131, K132, K538, and K539) and mutations to the amino acids believed to be stabilizing the phosphate backbone of the DNA were considered.

Example 2. Quantifying Processivity

Measuring the effects of the directed evolution using an in house developed a rolling circle amplification (RCA) assay and an exponential rolling circle amplification assay (eRCA) enabled us to identify which point mutations resulted in faster nucleotide incorporation.

Rolling Circle Amplification (RCA) Assays: RCA reactions contained 1×SG buffer (Tris HCl (pH 7.5 at 25° C.), $(NH_4)_2SO_4$, $MgCl_2$), 1 mM dNTPs, 0.1 nM single-stranded circular DNA, 4 μM SYTO™ 9 intercalating dye (ThermoFisher) to monitor amplification, 1 μM phosphorothioated primer-1 and 1 μM phosphorothioated primer-2 (for linear RCA only 1 μM phosphorothioated primer-2 is used), BSA, and 60-450 nM of the phi29 variant in a total reaction volume of 25 μL. Reactions were monitored using CFX96™ Real-Time System (Bio-Rad) by incubating at 37° C. for 2 hours and taking measurements with the SYBR filter every minute followed by 20 minutes at 65° C. to heat inactivate protein. Fluorescence measurements were normalized to start at a fluorescence value of 0 at t=0 by subtracting the initial fluorescence value from all subsequent measurements of a given reaction.

Each assay included testing the variant in triplicate, and suitable controls (e.g., wild-type and/or a no-template control). Upon binding to a dsDNA amplification product, the nucleic acid stain provides a strong fluorescent signal, the intensity of which is proportional to the amount of amplification products being generated. The fluorescence of the nucleic acid stain is continuously monitored over time to a point of saturation, enabling the quantification of a halftime. Reported in Table 1 is the variant and the relative halftime (i.e., relative to the wild-type). The relative halftime was calculated as the difference between average halftime for the variant and the average halftime for the wild-type. The average halftime recorded for the wild-type DNA polymerase is 15.6 minutes. Any improvement in kinetics (i.e., faster processivity) is reported as a negative value, whereas slower incorporation is provided as a positive value. The variants are referred to internally by an "MS" prefix and a sequential number in which they were identified. MS was chosen as a prefix in honor of Spanish biochemist Margarita Salas and her pioneering efforts to understand phi-29 enzymes (see Salas M. Bacteriophage. 2016 Dec. 15; 6(4): e1271250).

TABLE 1

Phi29 variants and a relative average halftime as quantified in the eRCA assay. Following measurements in triplicate, the variance in the relative average halftime +/− 2.0 min. The relative halftime was calculated as the difference between average halftime for the variant and the average halftime for the wild-type. For some variants, a halftime was not determined due to the lack of signal saturation during the assay time constraints and are indicated as having a relative halftime beyond ten minutes (min) (10.0+).

| Internal Ref | Rel $t_{1/2}$ (min) | Internal Ref | Rel $t_{1/2}$ (min) |
|---|---|---|---|
| MS-0 | 0.0 | MS-47 | −1.1 |
| MS-103 | −11.5 | MS-48 | −2.6 |
| MS-203 | 10.0+ | MS-49 | −8.0 |
| MS-204 | 10.0+ | MS-50 | −3.1 |
| MS-30 | −6.5 | MS-52 | −14.4 |
| MS-31 | −3.0 | MS-53 | −10.5 |
| MS-33 | −4.6 | MS-54 | −10.7 |
| MS-34 | −4.2 | MS-55 | −8.7 |
| MS-35 | −4.1 | MS-58 | −11.7 |
| MS-36 | −12.6 | MS-59 | −10.6 |
| MS-37 | −9.0 | MS-60 | −7.8 |
| MS-38 | −7.8 | MS-63 | −6.6 |
| MS-40 | −5.0 | MS-65 | −7.4 |
| MS-42 | −5.4 | MS-68 | −7.2 |
| MS-43 | −10.3 | MS-91 | −1.6 |
| MS-44 | −4.8 | MS-92 | −6.5 |
| MS-45 | −8.7 | MS-210 | −12.3 |
| MS-46 | −10.5 | MS-211 | −8.0 |

TABLE 1-continued

Phi29 variants and a relative average halftime as quantified in the eRCA assay. Following measurements in triplicate, the variance in the relative average halftime +/− 2.0 min. The relative halftime was calculated as the difference between average halftime for the variant and the average halftime for the wild-type. For some variants, a halftime was not determined due to the lack of signal saturation during the assay time constraints and are indicated as having a relative halftime beyond ten minutes (min) (10.0+).

| Internal Ref | Rel $t_{1/2}$ (min) | Internal Ref | Rel $t_{1/2}$ (min) |
|---|---|---|---|
| MS-207 | −10.6 | MS-212 | 0.0 |
| MS-208 | −8.3 | MS-213 | −5.7 |
| MS-209 | −12.4 | MS-214 | −6.1 |
| | | MS-216 | −8.8 |

Some of the variants and the relative average halftime are graphically depicted in FIG. 1. For example, variants MS-103, MS-207, MS-209, MS-210, MS-92, MS-63, MS-91, MS-68, and MS-65 displayed notably faster kinetics and the rapid generation of amplification products, relative to the wild-type polymerase (MS-0). The point mutations for each variant are provided in Table 3. A single point mutation relative to the wild type enzyme (i.e., relative to SEQ ID NO:1) can confer accelerated processivity and strand displacement. For example, MS-30 (K536E), MS-30, MS-33, MS-34, MS-35, MS-40, MS-43, MS-44, MS-47, MS-49, MS-55, MS-58, MS-91, and MS-92 all include a single point mutation and are faster than wild-type at generating amplification products. Interestingly, the point mutation K135E alone provides a fast enzyme (MS-49), however the inclusion of an additional mutation as found in MS-203 (K135E; T368D) and MS-204 (K135E; K512D), significantly retards the amplification rate such that MS-203 and MS-204 were among the worst performing enzymes for increased processivity. The combination of K135E and L216P, as found in MS-63, resulted in about a 42% increase in amplification rates relative to the wild-type over the same time interval. The combination of K135E, L216P, and K536E, as found in MS-103, provides one of the fastest enzymes, a 73% increase in amplification rates. Interestingly, additional point mutations proximate to the active exo center, such as K131E or K132E, resulted in even faster processivity than the combination of K135E, L216P, and K536E point mutations alone (e.g., MS-209 and MS-210). As shown in Table 3, the combination of point mutations to the exo domain (e.g., K131E, K132E, and K135E), K536E from the thumb domain, and L216P from the palm domain resulted in polymerase variants with improved processivity of the dsDNA amplification products. Improved performance by these polymerase variants (e.g., MS-103, MS-209, and MS-210) were hypothesized to result from the reduction of positive charge in the exo and thumb domains as the native exo and thumb domains harbored positively charged residues, such as K131, K132, K135, K536, K538, and K539 (as shown in FIG. 2B). Additionally, an important point mutation observed in variants with improved processivity compared to the wild type enzyme was L216P as polymerase variants with this point mutation exhibited at least 66% increase in amplification kinetics compared to the wild type enzyme (e.g., see MS-43, MS-52, MS-103, MS-207, MS-209, MS-210 in Table 3). Interestingly, the L216P point mutation alone resulted in 66% increase in amplification rates compared to the wild type enzyme (see MS-43 in Tables 1 and 3). As illustrated in FIG. 2B, these lysine residues encompass the surface of the exo tunnel and are hypothesized to participate in non-specific binding to the negatively charged backbone of DNA as some of the residues (i.e., K135 and K536) are 12-18 Å away from the active exo center; this is a reasonable distance for these residues to participate in electrostatic interactions with the DNA oligonucleotide in the active exo center and therefore decrease the processivity of the phi29 DNA polymerase. Efforts were focused on targeting these positively charged residues in the exo and thumb domains. For example, MS-216 harbored two point mutations in the thumb domain (K536E and K539E), two point mutations in the exo domain (K131E and K135E), and L216P in the palm domain, which resulted in improved processivity compared to the wild type by 8.8 minutes (as shown in Tables 1 and 3 and FIG. 4). Without wishing to be bound by any theory, it is suspected that the rate of eRCA (and also RCA) is limited by the rate of repriming, wherein the polymerase occasionally engages in non-productive binding to ssDNA. The mutations introduced in the polymerases increase the rate at which amplification products are generated.

Figure 4:
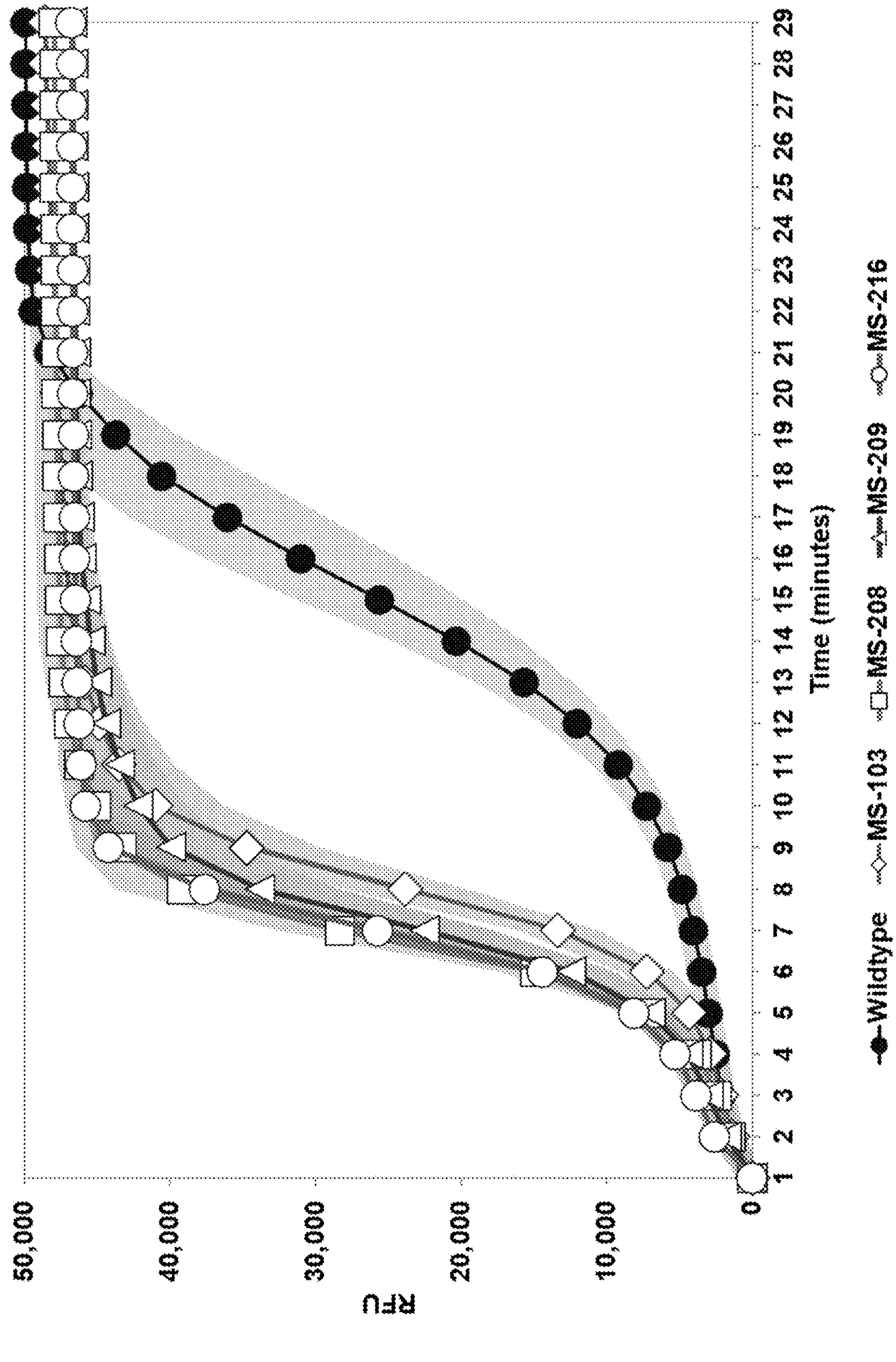
FIG. 4 provides amplification plots of the fluorescence of SYTO™ 9 dye used to monitor the generation of amplicons from wild type phi29 DNA polymerase and variants thereof in an exponential rolling circle amplification assay as detailed in Example 2. All the variants of phi29 DNA polymerase depicted in FIG. 4 harbor K135E, L216P, and K536E point mutations but differ based on whether they harbor additional point mutations: K131E, K132E, and/or K539E. Amplification plots for MS-103, MS-208, MS-209, and MS-216 are shown with open diamonds, squares, triangles, and circles, respectively, and these variants represent a subset of the superior variants disclosed herein. Variants depicted in FIG. 4 exhibited superior nucleotide processivity and facilitate faster amplification compared to wildtype phi29 DNA polymerase (shown in the plot with closed circles). Amplification plots shown are corrected for baseline fluorescence. Each amplification plot depicts the average relative fluorescence units (RFU) from triplicate measurements at each timepoint for each variant and wildtype enzyme. Shaded regions above and below each amplification plot signify the standard deviation relative from the average RFU at each timepoint for each variant and/or wild type.

In addition to evaluating relative halftimes of the variants, comparative analysis of the amplification plots from exponential rolling circle amplification assay with phi29 DNA polymerase variants and wildtype enzyme provide a supplemental view for how selected variants facilitate faster amplification compared to wildtype phi29 DNA polymerase. As shown in FIG. 4, a subset of superior variants, such as MS-103, MS-208, MS-209, and MS-216, generate amplicons faster than the wildtype enzyme in an exponential rolling circle amplification assay. All the variants of phi29 DNA polymerase depicted in FIG. 4 harbor K135E, L216P, and K536E point mutations but differ based on whether they harbor additional point mutations: K131E, K132E, and/or K539E.

Quantitative Real-Time Polymerase Chain Reaction, better known as qPCR, is a sensitive and specific technique for the detection of nucleic acids. qPCR works by amplifying the target DNA sequence using a specific set of primers that bind to the target sequence. The qPCR reaction produces millions of copies of the target sequence, which can then be measured and quantified, that is, qPCR generates a signal response that is proportional to the amount of nucleic acid material present in the sample. The Cq (or cycle threshold) is a measure of the quantity of target DNA present in a sample, referring to the cycle number at which the amount of fluorescence exceeds the background. The Cq value is used to compare the amount of target DNA present in two samples. For example, a the lower the Cq value, the higher the amount of target DNA present in the sample, while a higher Cq value indicates a lower amount of the target sequence in the sample. Table 2 reports on the measured Cq values for some of the variants provided herein. The experimental conditions include 900 mM of the enzyme, 1 mM dNTPs, 1 μM of each primer, 4 μM SYTO™ 9, 4 mM DTT, 2.5% glycerol, 0.2 mg/mL BSA, 0.1 nM template, 50 mM Tris, pH 7.5, 12 mM $MgCl_2$, $(NH_4)_2SO_4$, and Tween® 20.

TABLE 2

Mutant polymerase variants and their measured Cq values.

| Internal Ref | Cq (+/−0.25) |
|---|---|
| MS-0 | 20.1 |
| MS-207 | 9.9 |
| MS-208 | 12.2 |
| MS-209 | 8.2 |
| MS-210 | 8.2 |
| MS-211 | 12.4 |

TABLE 2-continued

| Mutant polymerase variants and their measured Cq values. | |
|---|---|
| Internal Ref | Cq (+/−0.25) |
| MS-212 | 20.5 |
| MS-213 | 14.8 |
| MS-214 | 14.4 |

TABLE 3

The mutant polymerase variants and their point mutations.

| Internal Ref | Amino Acid Mutation(s) Relative to SEQ ID NO: 1 |
|---|---|
| MS-0 | none |
| MS-103 | K135E; L216P; K536E |
| MS-203 | K135E; T368D |
| MS-204 | K135E; K512D |
| MS-30 | K536E |
| MS-31 | Y500F; K536E; S578I |
| MS-33 | I119V |
| MS-34 | S192C |
| MS-35 | K311R |
| MS-36 | P87S; I93N; I378V; K536E; S578G |
| MS-37 | D34E; G401V; L462I |
| MS-38 | K366R; A444V; K536E |
| MS-40 | V514I |
| MS-42 | L381Q; H485L; E486V |
| MS-43 | L216P |
| MS-44 | V509L |
| MS-45 | V565M; G579S |
| MS-46 | S260N; G417R |
| MS-47 | A447T |
| MS-48 | F47I; W436R |
| MS-49 | K135E |
| MS-50 | M8I; T203S; L216P |
| MS-52 | L216P; T231I |
| MS-53 | I179F; Y343C; S487C |
| MS-54 | E239G; T434S |
| MS-55 | R552Q |
| MS-58 | F198L |
| MS-59 | V19L; K132M; K536E |
| MS-60 | D219N; A324T; L567M |
| MS-63 | K135E; L216P |
| MS-65 | P87S; I93N; K135E; I378V; K536E; S578G |
| MS-68 | P87S; I93N; K366R; I378V; K536E; S578G |
| MS-91 | A394V |
| MS-92 | G417R |
| MS-207 | K538E; K135E; L216P; K536E |
| MS-208 | K539E; K135E; L216P; K536E |
| MS-209 | K131E; K135E; L216P; K536E |
| MS-210 | K132E; K135E; L216P; K536E |
| MS-211 | K538E; K539E; K135E; L216P; K536E |
| MS-212 | K131E; K132E; K135E; L216P; K536E |
| MS-213 | K538E; K131E; K135E; L216P; K536E |
| MS-214 | K539E; K132E; K135E; L216P; K536E |
| MS-215 | K538E; K539E; K131E; K132E; K135E; L216P; K536E |
| MS-216 | K539E; K131E; K135E; L216P; K536E |

Example 3. Polymerase Variants for Sequencing

Phi29 DNA polymerase variants are applied in DNA nanoball-based sequencing, real-time DNA sequencing from single polymerase molecules, and some nanopore sequencing methods. For example, nanopore sequencing approaches commercialized by Pacific Biosciences, the polymerase-assisted nanopore sequencing technology analyzes polynucleotide sequences as a function of changes in electrical current. Typically, this approach requires polymerases to perform incorporation at elevated salt concentrations, e.g., about 0.3 M KCl, which strains the DNA binding and enzymatic processivity due to the poor salt tolerance of wild-type phi29. Means for improving the salt tolerance of these enzymes include fusing a secondary protein to the terminus of the phi29 polymerase. For example, previous studies have reported that chimeric phi29 polymerases (i.e., a phi29 polymerase or a mutant thereof covalently linked to a second protein) produced by fusing one or two helix-hairpin-helix (HhH)2 domains increase DNA binding without decreasing processivity (de Vega, M et al. Proc Natl Acad Sci USA 107: 16506-16511 (2010). More recently, Gao et al. described fusing eight repeats of the (HhH)2 domains E-L topoisomerase V (Topo V) from the hyperthermophile *Methanopyrus kandleri* to the C-terminus of the phi29 polymerase (Gao et al., Microbial Biotechnology Volume 14, Issue 4, pp 1642-1656 (2021)) to improve the salt tolerance.

The variants described herein may be fused to an additional protein (e.g., an additional protein is covalently linked to the C-terminus of the variant described herein). For example, the BR3 polymerase contains negatively charged residues and random coils, and may be fused to a polymerase described herein. Additional fusions contemplated herein include Gss-polymerase derivatives, or the Sto7d protein (from *Sulfolobus tokodaii*).

Additionally, when using a phi29 polymerase for sequencing applications, the 3'-5' exonuclease proofreading activity of phi29 DNA polymerase can cause undesired degradation.

Figure 2A:
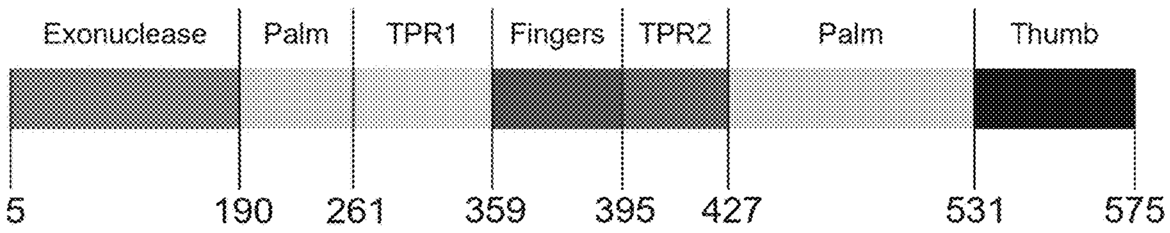
FIGS. 2A and 2B.
Figure 2B:
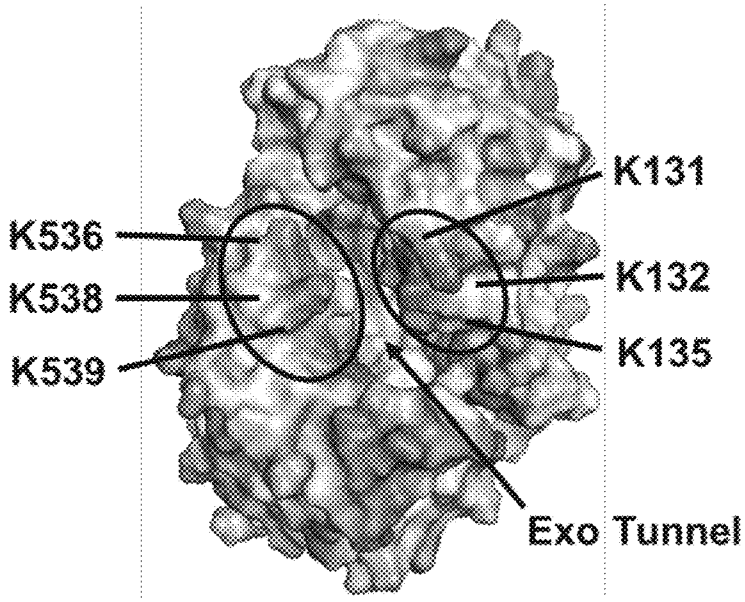

The functional domains responsible for the exonuclease activity are primarily located in Exo-I, Exo-II and Exo-III motifs in the N-terminus, as illustrated in FIG. 2A, spanning amino acid positions 5 to 195 of SEQ ID NO:1. Amino acid residues, such as aspartic acid at position 12 (D12), glutamic acid at position 14 (E14), aspartic acid at position 66 (D66), tyrosine at position 165 (Y165), aspartic acid at position 169 (D169), are understood to be specifically involved in the exonuclease activity. However, these amino acid residues are also closely related to the strand-displacement ability of the DNA polymerase. Therefore, substituting these residues may impact the strand-displacement activity of phi29 DNA polymerase. For example, amino acid substitutions such as T15I (i.e. mutation of threonine at position 15 into isoleucine) or N62D mutation (i.e. mutation of asparagine at position 62 into aspartic acid) reduces the 3'-5' exonuclease activity of phi29 DNA polymerase significantly while remaining the strand-displacement activity, however the phi29 DNA polymerase variant with T15I or N62D substitution tolerates the insertion of mismatched nucleotides due to greatly reduced ability of stabilizing single-stranded DNA, thus exhibiting largely lower fidelity.

Example 4. Point of Care Applications

Point-of-care (POC) diagnostics are medical tools, instruments, compositions and/or devices enabling disease diagnosis, typically within in a patient community and outside a traditional hospital setting. The ideal diagnostic test should meet the “ASSURED” criteria: Affordable, Sensitive, Specific, User-friendly, Rapid and robust, Equipment-free and Delivered to those who need it. POC methods are preferably simple and do not require a heat source or stable power supply as these are typically not available at POC. Thus, enzymes and reagents used should work at ambient temperatures.

Detecting biomolecules, such as nucleic acids, typically require some sort of amplification to produce a sufficient quantity to enable robust detection. PCR technology has a high potential, however it still has strict limitations and requires the use of electrically powered thermal cycling equipment for repeated heating and cooling processes and skilled personnel to run the equipment. Non-PCR based methods, in particular Isothermal Amplification (IA) methods, have emerged as promising approaches. In these methods, nucleic acid amplification takes place at constant temperatures and has no need for high precision temperature cycling and control, or enzymes stable at high temperatures. Isothermal amplification methods are reported to have analytical sensitivities and specificities comparable to PCR as well as a higher tolerance to inhibitory compounds, while allowing shorter time to results and easier use. These features make isothermal amplification methods highly desirable for those developing POC molecular diagnostics platforms and aiming to meet "ASSURED" criteria. A number of different methods have in the last decade been published for isothermal amplification of nucleic acids, such as for example as summarized in Gill P, Ghaemi A. Nucleic acid isothermal amplification technologies: a review. Nucleosides Nucleotides Nucleic Acids. 2008 March; 27(3):224-43; and/or Botella JR. Point-of-Care DNA Amplification for Disease Diagnosis and Management. Annu Rev Phytopathol. 2022 Aug. 26; 60:1-20. Isothermal amplification approaches typically rely on the inherent strand displacement activity of the polymerase used in the reaction. The term strand displacement describes the ability of the polymerase to displace downstream DNA encountered during synthesis/extension.

Provided herein are polymerases and enzymes, capable of being used in point-of-care applications and/or isothermal amplification techniques. For example, a sample including a nucleic acid of interest (e.g., a pathogenic nucleic acid sequence, such as SARS-CoV-2) is combined in a reaction vessel with a circularizable (e.g., a padlock probe) template, with a ligase (e.g., SplintR® ligase), a polymerase as described herein, a plurality of nucleotides, and a colorimetric probe, such as RHthio-$CuSO_4$. The colorimetric probe changes color upon to formation of pyrophosphate resulting from isothermal gene amplification if the nucleic acid of interest is present.

ADDITIONAL EMBODIMENTS

Embodiment 1. A polymerase comprising an amino acid sequence that is at least 80% identical to SEQ ID NO:1; comprising an amino acid substitution, wherein said amino acid substitution is: a proline, tryptophan, phenylalanine, tyrosine, alanine, or glycine an amino acid position corresponding to position 216 of SEQ ID NO:1; an arginine, lysine, asparagine, glutamine, alanine, or glycine at an amino acid position corresponding to position 417 of SEQ ID NO:1; a valine, lysine, asparagine, glutamine, alanine, or glycine at an amino acid position corresponding to position 394 of SEQ ID NO:1; and/or an asparagine, glutamine, alanine, or glycine at an amino acid position corresponding to position 93 of SEQ ID NO:1.

Embodiment 2. The polymerase of Embodiment 1, wherein the polymerase comprises an arginine, lysine, asparagine, or glutamine at the amino acid position corresponding to position 417.

Embodiment 3. The polymerase of Embodiment 1, wherein the polymerase comprises an arginine at the amino acid position corresponding to position 417.

Embodiment 4. The polymerase of Embodiment 1, wherein the polymerase comprises a valine, lysine, alanine, or glycine at the amino acid position corresponding to position 394.

Embodiment 5. The polymerase of Embodiment 1, wherein the polymerase comprises a valine at the amino acid position corresponding to position 394.

Embodiment 6. The polymerase of Embodiment 1, wherein the polymerase comprises a proline, tryptophan, phenylalanine, tyrosine, alanine, or glycine at the amino acid position corresponding to position 216; and further comprises a glutamic acid, aspartic acid, alanine, or glycine at an amino acid position corresponding to position 135 of SEQ ID NO:1.

Embodiment 7. The polymerase of Embodiment 1, wherein the polymerase comprises a proline, tryptophan, phenylalanine, tyrosine, alanine, or glycine at the amino acid position corresponding to position 216; and further comprises a glutamic acid at an amino acid position corresponding to position 135 of SEQ ID NO:1.

Embodiment 8. The polymerase of any one of Embodiments 1 to 7, wherein the polymerase further comprises a glutamic acid, aspartic acid, alanine, glycine, or threonine at an amino acid position corresponding to position 536 of SEQ ID NO:1.

Embodiment 9. The polymerase of any one of Embodiments 1 to 8, wherein the polymerase comprises a proline at the amino acid position corresponding to position 216; a glutamic acid, aspartic acid, alanine, or glycine at the amino acid position corresponding to position 135; and a glutamic acid, aspartic acid, alanine, glycine, or threonine at the amino acid position corresponding to position 536.

Embodiment 10. The polymerase of any one of Embodiments 1 to 8, wherein the polymerase comprises a proline at an amino acid position corresponding to position 216; a glutamic acid or aspartic acid at the amino acid position corresponding to position 135; and a glutamic acid or aspartic acid at the amino acid position corresponding to position 536.

Embodiment 11. The polymerase of any one of Embodiments 1 to 8, wherein the polymerase comprises a proline at the amino acid position corresponding to position 216; a glutamic acid at the amino acid position corresponding to position 135; and a glutamic acid at the amino acid position corresponding to position 536.

Embodiment 12. The polymerase of any one of Embodiments 1 to 11, further comprising a serine, threonine, tyrosine, alanine, or glycine at an amino acid position corresponding to position 87 of SEQ ID NO:1.

Embodiment 13. The polymerase of any one of Embodiments 1 to 11, further comprising a serine at an amino acid position corresponding to position 87 of SEQ ID NO:1.

Embodiment 14. The polymerase of any one of Embodiments 1 to 13, further comprising a valine, leucine, alanine, or glycine at an amino acid position corresponding to position 378 of SEQ ID NO:1.

Embodiment 15. The polymerase of any one of Embodiments 1 to 13, further comprising a valine at an amino acid position corresponding to position 378 of SEQ ID NO:1.

Embodiment 16. The polymerase of any one of Embodiments 1 to 15, further comprising a glycine, alanine, valine, serine, or threonine at an amino acid position corresponding to position 578 of SEQ ID NO:1.

Embodiment 17. The polymerase of any one of Embodiments 1 to 15, further comprising a glycine at an amino acid position corresponding to position 578 of SEQ ID NO:1.

Embodiment 18. The polymerase of any one of Embodiments 1 to 17, further comprising an arginine, histidine, asparagine, glutamine, alanine, or glycine at an amino acid position corresponding to position 366 of SEQ ID NO:1.

Embodiment 19. The polymerase of any one of Embodiments 1 to 17, further comprising an arginine, at an amino acid position corresponding to position 366 of SEQ ID NO:1.

Embodiment 20. The polymerase of any one of Embodiments 1 to 19, further comprising an alanine, lysine, arginine, histidine, asparagine, and glutamine at an amino acid position corresponding to position 8 of SEQ ID NO:1.

Embodiment 21. The polymerase of any one of Embodiments 1 to 20, further comprising a glutamic acid and amino acid position corresponding to position 538 of SEQ ID NO:1.

Embodiment 22. The polymerase of any one of Embodiments 1 to 21, further comprising a glutamic acid and amino acid position corresponding to position 539 of SEQ ID NO:1.

Embodiment 23. The polymerase of any one of Embodiments 1 to 22, further comprising a glutamic acid and amino acid position corresponding to position 131 of SEQ ID NO:1.

Embodiment 24. The polymerase of any one of Embodiments 1 to 23, further comprising a glutamic acid and amino acid position corresponding to position 132 of SEQ ID NO:1.

Embodiment 25. A polymerase comprising an amino acid sequence that is at least 80% identical to SEQ ID NO: 1; comprising an amino acid substitution, wherein said amino acid substitution comprises A324T, A394G, A394K, A394N, A394Q, A394V, A444I, D219N, D34A, D34E, D34N, D34Q, E239A, E239V, E486V, F198L, F47I, G401A, G401L, G401V, G417A, G417K, G417N, G417Q, G417R, G579A, G579S, G579T, G579Y, H485L, I119A, I119G, I119L, I119V, I179F, I378A, I378G, I378L, I378V, I93A, I93G, I93N, I93Q, K131A, K131D, K131E, K131G, K131T, K132A, K132D, K132E, K132G, K132T, K135A, K135D, K135E, K135G, K311N, K311Q, K311R, K366A, K366G, K366H, K366N, K366Q, K366R, K536A, K536D, K536E, K536G, K536T, K539A, K539D, K539E, K539G, K539T, L216A, L216F, L216G, L216P, L216W, L216Y, L381Q, L462A, L462G, L462I, L462L, L462V, L567M, P87A, P87G, P87S, P87T, P87Y, R552A, R552N, R552Q, S192A, S192C, S192G, S260N, S260Q, S487C, S578A, S578G, S578I, S578L, S578T, S578V, T203S, T231A, T231I, T231V, T434A, T434G, T434Y, V565A, V565G, V565M, W436R, Y343C, Y500A, Y500F, or Y500G.

Embodiment 26. The polymerase of Embodiment 25, comprising the amino acid substitution: D34E, F47I, P87S, I93N, I119V, K131E, K132E, K135E, I179F, S192C, F198L, T203S, L216P, D219N, T231I, E239G, S260N, K311R, A324T, Y343C, K366R, I378V, L381Q, A394V, G401V, G417R, W436R, A444V, A447T, L462I, H485L, E486V, S487C, Y500F, K536E, K539E, R552Q, V565M, L567M, S578G, or G579S.

Embodiment 27. The polymerase of Embodiment 25, comprising the amino acid substitutions: i) K135E; L216P; and K536E; ii) G417R; iii) K135E and L216P; iv) A394V; v) P87S; I93N; K366R; I378V; K536E; and S578G; vi) P87S; I93N; I378V; K536E; and S578G; or vii) P87S; I93N; K135E; I378V; K536E; and S578G.

Embodiment 28. A polymerase comprising an amino acid sequence that is at least 80% identical to SEQ ID NO: 1; comprising a proline, tryptophan, phenylalanine, tyrosine, alanine, or glycine at an amino acid position corresponding to position 216 of SEQ ID NO:1; and a glutamic acid, aspartic acid, alanine, or glycine at an amino acid position corresponding to position 135 of SEQ ID NO:1.

Embodiment 29. The polymerase of Embodiment 28, comprising a proline at the amino acid position corresponding to position 216.

Embodiment 30. The polymerase of Embodiments 28 or 29, further comprising a glutamic acid, aspartic acid, alanine, glycine, or threonine at an amino acid position corresponding to position 536 of SEQ ID NO:1.

Embodiment 31. The polymerase of any one of Embodiments 28 to 30, further comprising a glutamic acid, aspartic acid, alanine, glycine, or threonine at an amino acid position corresponding to position 538 of SEQ ID NO:1.

Embodiment 32. The polymerase of any one of Embodiments 28 to 31, further comprising a glutamic acid, aspartic acid, alanine, glycine, or threonine at an amino acid position corresponding to position 539 of SEQ ID NO:1.

Embodiment 33. The polymerase of any one of Embodiments 28 to 32, further comprising a glutamic acid, aspartic acid, alanine, glycine, or threonine at an amino acid position corresponding to position 131 of SEQ ID NO:1.

Embodiment 34. The polymerase of any one of Embodiments 28 to 33, further comprising a glutamic acid, aspartic acid, alanine, glycine, or threonine at an amino acid position corresponding to position 132 of SEQ ID NO:1.

Embodiment 35. A polymerase comprising an amino acid sequence that is at least 85% identical to SEQ ID NO: 1; comprising an arginine, lysine, asparagine, glutamine, alanine, or glycine at an amino acid position corresponding to position 417 of SEQ ID NO:1.

Embodiment 36. A polymerase comprising an amino acid sequence that is at least 85% identical to SEQ ID NO: 1; comprising a valine, lysine, asparagine, glutamine, alanine, or glycine at an amino acid position corresponding to position 394 of SEQ ID NO:1.

Embodiment 37. A polymerase comprising an amino acid sequence that is at least 85% identical to SEQ ID NO: 1; comprising a serine, threonine, tyrosine, alanine, or glycine at an amino acid position corresponding to position 87 of SEQ ID NO:1; an asparagine, glutamine, alanine, or glycine at an amino acid position corresponding to position 93 of SEQ ID NO:1; a valine, leucine, alanine, or glycine at an amino acid position corresponding to position 378 of SEQ ID NO:1; a glutamic acid, aspartic acid, alanine, glycine, or threonine at an amino acid position corresponding to position 536 of SEQ ID NO:1; and a glycine, alanine, valine, serine, or threonine at an amino acid position corresponding to position 578 of SEQ ID NO:1.

Embodiment 38. The polymerase of Embodiment 37, further comprising an arginine, histidine, asparagine, glutamine, alanine, or glycine at an amino acid position corresponding to position 366 of SEQ ID NO:1.

Embodiment 39. A method of incorporating a nucleotide into a nucleic acid sequence comprising combining in a reaction vessel: i) a nucleic acid template, ii) a nucleotide solution comprising a plurality of nucleotides, and (iii) a polymerase, wherein the polymerase is a polymerase of claim any one of Embodiments 1 to 38.

Embodiment 40. A method of amplifying a nucleic acid sequence, said method comprising: a) hybridizing a nucleic acid template to a primer to form a primer-template hybridization complex; b) contacting said primer-template hybridization complex with a DNA polymerase and a plurality of nucleotides, wherein the DNA polymerase is the polymerase of claim any one of Embodiments 1 to 38; and c) subjecting the primer-template hybridization complex to conditions which enable the polymerase to incorporate one or more nucleotides into the primer-template hybridization complex to generate amplification products, thereby amplifying a nucleic acid sequence.

Embodiment 41. A method of amplifying a template polynucleotide, the method comprising: contacting a template polynucleotide with an amplification primer, and amplifying the template polynucleotide by extending an amplification primer with a polymerase to generate an extension product comprising one or more complements of the template polynucleotide; wherein said polymerase is a polymerase of any one of Embodiments 1 to 38.

Embodiment 42. The method of Embodiment 41, comprising amplifying the template polynucleotide in a cell.

Embodiment 43. The method of Embodiment 41, comprising amplifying the template polynucleotide in a tissue.

Embodiment 44. The method of Embodiment 41, wherein said amplification primer is immobilized on a solid support.

Embodiment 45. A polymerase comprising an amino acid sequence that is at least 80% identical to SEQ ID NO: 1; comprising a proline, tryptophan, phenylalanine, tyrosine, alanine, or glycine at an amino acid position corresponding to position 216 of SEQ ID NO:1.

Embodiment 46. A polymerase of Embodiment 45, comprising a proline at amino acid position corresponding to position 216.

Embodiment 47. A polymerase of Embodiment 45 or Embodiment 46, further comprising a glutamic acid, aspartic acid, alanine, or glycine at an amino acid position corresponding to position 135 of SEQ ID NO:1.

Embodiment 48. A polymerase of Embodiment 45 or Embodiment 46, comprising a glutamic acid at an amino acid position corresponding to position 135.

Embodiment 49. A polymerase of any one of Embodiments 45 to 48, further comprising a glutamic acid, aspartic acid, alanine, glycine, or threonine at an amino acid position corresponding to position 536 of SEQ ID NO:1.

Embodiment 50. A polymerase of any one of Embodiments 45 to 48, comprising a glutamic acid at an amino acid position corresponding to position 536.

Embodiment 51. A polymerase of any one of Embodiments 45 to 50, further comprising a glutamic acid, aspartic acid, alanine, glycine, or threonine at an amino acid position corresponding to position 538 of SEQ ID NO:1.

Embodiment 52. A polymerase of any one of Embodiments 45 to 51, further comprising a glutamic acid, aspartic acid, alanine, glycine, or threonine at an amino acid position corresponding to position 539 of SEQ ID NO:1.

Embodiment 53. A polymerase of any one of Embodiments 45 to 52, further comprising a glutamic acid, aspartic acid, alanine, glycine, or threonine at an amino acid position corresponding to position 131 of SEQ ID NO:1.

Embodiment 54. A polymerase of any one of Embodiments 45 to 53, further comprising a glutamic acid, aspartic acid, alanine, glycine, or threonine at an amino acid position corresponding to position 132 of SEQ ID NO:1.

Embodiment 55. A polymerase of any one of Embodiments 45 to 54, comprising the amino acid substitution: K131E, K135E, L216P, and K536E.

Embodiment 56. A polymerase of any one of Embodiments 45 to 54, comprising the amino acid substitution: K135E, L216P, K536E, and K539E.

```
SEQUENCES
WT;
SEQ ID NO: 1:
MKHMPRKMYSCDFETTTKVEDCRVWAYGYMNIEDHSEYKIGNSLD

EFMAWVLKVQADLYFHNLKFDGAFIINWLERNGFKWSADGLPNTY

NTIISRMGQWYMIDICLGYKGKRKIHTVIYDSLKKLPFPVKKIAK

DFKLTVLKGDIDYHKERPVGYKITPEEYAYIKNDIQIIAEALLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWLSNVDLELMKEHYDLYNVEYISGLKFKATTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRAKYL

RQKTYIQDIYMKEVDGKLVEGSPDDYTDIKFSVKCAGMTDKIKKE

VTFENFKVGFSRKMKPKPVQVPGGVVLVDDTFTIK

Min WT;
SEQ ID NO: 2:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYKITPEEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPAQMYSRLLPYGEPIVFEG

KYVWDEDYPLHIQHIRCEFELKEGYIPTIQIKRSRFYKGNEYLKS

SGGEIADLWLSNVDLELMKEHYDLYNVEYISGLKFKATTGLFKDF

IDKWTYIKTTSEGAIKQLAKLMLNSLYGKFASNPDVTGKVPYLKE

NGALGFRLGEEETKDPVYTPMGVFITAWARYTTITAAQACYDRII

YCDTDSIHLTGTEIPDVIKDIVDPKKLGYWAHESTFKRAKYLRQK

TYIQDIYMKEVDGKLVEGSPDDYTDIKFSVKCAGMTDKIKKEVTF

ENFKVGFSRKMKPKPVQVPGGVVLVDDTFTIK

Salasvirus phi29;
SEQ ID NO: 3:
MKHMPRKMYSCDFETTTKVEDCRVWAYGYMNIEDHSEYKIGNSLD

EFMAWVLKVQADLYFHNLKFDGAFIINWLERNGFKWSADGLPNTY

NTIISRMGQWYMIDICLGYKGKRKIHTVIYDSLKKLPFPVKKIAK

DFKLTVLKGDIDYHKERPVGYKITPEEYAYIKNDIQIIAEALLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWLSNVDLELMKEHYDLYNVEYISGLKFKATTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRAKYL
```

-continued

RQKTYIQDIYMKEVDGKLVEGSPDDYTDIKFSVKCAGMTDKIKKE

VTFENFKVGFSRKMKPKPVQVPGGVVLVDDTFTIK

DNA polymerase *Bacillus* phage phi29.1:
SEQ ID NO: 4:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYKITPEEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPAQMYSRLLPYGEPIVFEG

KYVWDEDYPLHIQHIRCEFELKEGYIPTIQIKRSRFYKGNEYLKS

SGGEIADLWLSNVDLELMKEHYDLYNVEYISGLKFKATTGLFKDF

IDKWTYIKTTSEGAIKQLAKLMLNSLYGKFASNPDVTGKVPYLKE

NGALGFRLGEEETKDPVYTPMGVFITAWARYTTITAAQACYDRII

YCDTDSIHLTGTEIPDVIKDIVDPKKLGYWAHESTFKRAKYLRQK

TYIQDIYMKEVDGKLVEGSPDDYTDIKFSVKCAGMTDKIKKEVTF

ENFKVGFSRKMKPKPVQVPGGVVLVDDTFTIK

DNA polymerase, partial *Tannerella* sp.
oral taxon BU063 isolate;
SEQ ID NO: 5:
GGFTWLNDRFKEKEIGEGMVFDVNSLYPAQMYSRLLPYGEPIVFE

GKYVWDEDYPLHIQHIRCEFELKEGYIPTIQIKRSRFYKGNEYLK

SSGGEIADLWLSNVDLELMKEHYDLYNVEYISGLKFKATTGLFKD

FIDKWTYIKTTSEGAIKQLAKLMLNSLYGKFASNPDVTGKVPYLK

ENGALGFRLGEEETKDPVYTPMGVFITAWARYTTITAAQACYDRI

IYCDTDSIHLTGTEIPDVIKDIVDPKKLGYWAHESTFKRAKYLRQ

KTYIQDIYMKEVDGKLVEGSPDDYTDIKFSVKCAGMTDKIKKEVT

FENFKVGFSRKMKPKPVQVPGGVVLVDDTFTIK

DNA polymerase *Tannerella* sp. oral taxon
BU063 isolate Cell 6/7/9;
SEQ ID NO: 6:
MYSRLLPYGEPIVFEGKYVWDEDYPLHIQHIRCEFELKEGYIPTI

QIKRSRFYKGNEYLKSSGGEIADLWLSNVDLELMKEHYDLYNVEY

ISGLKFKATTGLFKDFIDKWTYIKTTSEGAIKQLAKLMLNSLYGK

FASNPDVTGKVPYLKENGALGFRLGEEETKDPVYTPMGVFITAWA

RYTTITAAQACYDRIIYCDTDSIHLTGTEIPDVIKDIVDPKKLGY

WAHESTFKRAKYLRQKTYIQDIYMKEVDGKLVEGSPDDYTDIKFS

VKCAGMTDKIKKEVTFENFKVGFSRKMKPKPVQVPGGVVLVDDTF

TIK

*Escherichia coli* HPP;
SEQ ID NO: 7:
MASMTGGQQMGRIRMPRKMYSCDFETTTKVEDCRVWAYGYMNIED

HSEYKIGNSLDEFMAWVLKVQADLYFHNLKFDGAFIINWLERNGF

KWSADGLPNTYNTIISRMGQWYMIDICLGYKGKRKIHTVIYDSLK

KLPFPVKKIAKDFKLTVLKGDIDYHKERPVGYKITPEEYAYIKND

IQIIAEALLIQFKQGLDRMTAGSDSLKGFKDIITTKKFKKVFPTL

-continued

SLGLDKEVRYAYRGGFTWLNDRFKEKEIGEGMVFDVNSLYPAQMY

SRLLPYGEPIVFEGKYVWDEDYPLHIQHIRCEFELKEGYIPTIQI

KRSRFYKGNEYLKSSGGEIADLWLSNVDLELMKEHYDLYNVEYIS

GLKFKATTGLFKDFIDKWTYIKTTSEGAIKQLAKLMLNSLYGKFA

SNPDVTGKVPYLKENGALGFRLGEEETKDPVYTPMGVFITAWARY

TTITAAQACYDRIIYCDTDSIHLTGTEIPDVIKDIVDPKKLGYWA

HESTFKRAKYLRQKTYIQDIYMKEVDGKLVEGSPDDYTDIKFSVK

CAGMTDKIKKEVTFENFKVGFSRKMKPKPVQVPGGVVLVDDTFTI

KLEHHHHHH

DNA polymerase *Bacillus* phage BSTP4;
SEQ ID NO: 8:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYKITPEEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPAQMYSRLLPYGEPIAFEG

KYVWDEDYPLHIQHIRCEFELKEGYIPTIQIKRSRFYKGNEYLKS

SGGEIADLWLSNVDLELMKEHYDLYNVEYISGLKFKATTGLFKDF

IDKWTYIKTTSEGAIKQLAKLMLNSLYGKFASNPDVTGKVPYLKE

NGALGFRLGEEETKDPVYTPMGVFITAWARYTTITAAQACYDRII

YCDTDSIHLTGTEIPDVIKDIVDPKKLGYWAHESTFKRAKYLRQK

TYIQDIYMKEVDGKLVEGSPDDYTDIKFSVKCAGMTDKIKKEVTF

ENFKVGFSRKMKPKPVQVPGGVVLVDDTFTIK

*Bacillus* phage phi29 UPP.1;
SEQ ID NO: 9:
MKHMPRKMYSCDFETTTKVEDCRVWAYGYMNIEDHSEYKIGNSLD

EFMAWVLKVQADLYFHNLKFDGAFIINWLERNGFKWSADGLPNTY

NTIISRMGQWYMIDICLGYKGKRKIHTVIYDSLKKLPFPVKKIAK

DFKLTVLKGDIDYHKERPVGYKITPEEYAYIKNDIQIIAERLLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWLSNVDLELMKEHYDLYNVEYISGLKFKATTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRVKYL

RQKTYIQDIYMKEVDGKLVEGSPDDYTDIKFSVKCAGMTDKIKKE

VTFENFKVGFSRKMKPKPVQVPGGVVLVDDTFTIK

*Bacillus* phage phi29 UPP.2;
SEQ ID NO: 10:
MKHMPRKMYSCDFETTTKVEDCRVWAYGYMNIEDHSEYKIGNSLD

EFMAWVLKVQADLYFHNLKFDGAFIINWLERNGFKWSADGLPNTY

-continued

NTIISRMGQWYMIDICLGYKGKRKIHTVIYDSLKKLPFPVKKIAK

DFKLTVLKGDIDYHKERPVGYKITPEEYAYIKNDIQIIAERLLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWLSNVDLELMKEHYDLYNVEYISGLKFKVTTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRAKYL

RQKTYIQDIYMKEVDGKLVEGSPDDYTDIKFSVKCAGMTDKIKKE

VTFENFKVGFSRKMKPKPVQVPGGVVLVDDTFTIK

Chain A, DNA polymerase Salasvirus phi29;
SEQ ID NO: 11:
MKHMPRKMYSCAFETTTKVEDCRVWAYGYMNIEDHSEYKIGNSLD

EFMAWVLKVQADLYFHNLKFAGAFIINWLERNGFKWSADGLPNTY

NTIISRMGQWYMIDICLGYKGKRKIHTVIYDSLKKLPFPVKKIAK

DFKLTVLKGDIDYHKERPVGYKITPEEYAYIKNDIQIIAEALLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWLSNVDLELMKEHYDLYNVEYISGLKFKATTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRAKYL

RQKTYIQDIYMKEVDGKLVEGSPDDYTDIKFSVKCAGMTDKIKKE

VTFENFKVGFSRKMKPKPVQVPGGVVLVDDTFTIK

Primer terminal protein *Bacillus* phage BSTP6;
SEQ ID NO: 12:
MKHMPRKMYSCDFETTTKVEDCRVWAYGYMNIENHSEYKIGNSLD

EFMAWVLKVQADLYFHNLKFDGAFIINWLERNGFKWSADGLPNTY

NTIISRMGQWYMIDICLGYKGKRKIHTVIYDSLKKLPFPVKKIAK

DFKLTVLKGDIDYHKERPVGYKITPEEYAYIKNDIQIIAEALLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWVSNVDLELMKEHYDLYNVEYISGLKFKATTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRAKYL

RQKTYIQDIYMKEVDGKLVEGSPDDYTDIKFSVKCAGMTDKIKKE

VTFDNFKVGFSRKMKPKPVQVPGGVVLVDDTFTIK

-continued

*Bacillus velezensis* HP;
SEQ ID NO: 13:
MNIEDHSDYKIGNSLDEFMAWAMKVQADLYFHNLKFDGAFIINWL

ERNGFKWSADGLPNTYNTIISRMGQWYMIDICLGYKGKRKIHTVI

YDSLKKLPFPVKKIAKDFKLTVLKGDIDYHKERPVGYKITPEEYA

YIKNDIQIIAEALLIQFKQGLDRMTAGSDSLKGFKDIITTKKFKK

VFPTLSLGLDKEVRYAYRGGFTWLNDRFKEKEIGEGMVFDVNSLY

PAQMYSRLLPYGEPIVFEGKYVWDEDYPLHIQHIRCEFELKEGYI

PTIQIKRSRFYKGNEYLKSSGGEIADLWLSNVDLELMKEHYDLYN

VEYISGLKFKATTGLFKDFIDKWTYIKTTSEGAIKQLAKLMLNSL

YGKFASNPDVTGKVPYLKENGALGFRLGEEETKDPVYTPMGVFIT

AWARYTTITAAQACYDRIIYCDTDSIHLTGTEIPDVIKDIVDPKK

LGYWAHESTFKRAKYLRQKTYIQDIYMKEVDGKLVEGSPDDYTDI

KFSVKCAGMTDKIKKEVTFENFKVGFSRKMKPKPVQVPGGVVLVD

DTFTIK

*Bacillus velezensis*, HPP.2;
SEQ ID NO: 14:
MSRKMYSCDFETTTKVEDCRVWAYGYMNIEDHSDYKIGNSLDEFM

AWAMKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYKITPEEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPAQMYSRLLPYGEPIVFEG

KYVWDEDYPLHIQHIRCEFELKEGYIPTIQIKRSRFYKGNEYLKS

SGGEIADLWLSNVDLELMKEHYDLYNVEYISGLKFKATTGLFKDF

IDKWTYIKTTSEGAIKQLAKLMLNSLYGKFASNPDVTGKVPYLKE

NGALGFRLGEEETKDPVYTPMGVFITAWARYTTITAAQACYDRII

YCDTDSIHLTGTEIPDVIKDIVDPKKLGYWAHESTFKRAKYLRQK

TYIQDIYMKEVDGKLVEGSPDDYTDIKFSVKCAGMTDKIKKEVTF

ENFKVGFSRKMKPKPVQVPGGVVLVDDTFTIK

DNA polymerase *Bacillus* phage Arbo1;
SEQ ID NO: 15:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYEITPDEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPAQMYSRLLPYGEPIVFEG

KYVWDEDYPLHIQHIRCEFELKEGYIPTIQIKRSRFYKGNEYLKS

SGGEIADLWVSNVDLELMKEHYDLYNVEYISGLKFKATTGLFKDF

IDKWTHIKTTSEGAIKQLAKLMLNSLYGKFASNPDVTGKVPYLKE

NGALGFRLGEEETKDPVYTPMGVFITAWARYTTITAAQACFDRII

YCDTDSIHLTGTEIPDVIKDIVDPKKLGYWAHESTFKRAKYLRQK

-continued

TYIQDIYMKEVDGKLVEGSPDDYTTIKFSVKCAGMTDKIKKEVTF

DNFKVGFSRKMKPKPVQVPGGVVLVDDTFTIK

H3027_gp06 *Bacillus* phage PZA;
SEQ ID NO: 16:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYEITPDEYAYIKNDIQIIAEALLIQFKQ

GLDRMTAGSDDLKGFKDIITTKKFKKVFPTLSLGLDKEVRYAYRG

GFTWLNDRFKEKEIGEGMVFDVNSLYPAQMYSRLLPYGEPIVFEG

KYVWDEDYPLHIQHIRCEFELKEGYIPTIQIKRSRFYKGNEYLKS

SGGEIADLWVSNVDLELMKEHYDLYNVEYISGLKFKATTGLFKDF

IDKWTHIKTTSEGAIKQLAKLMLNSLYGKFASNPDVTGKVPYLKE

NGALGFRLGEEETKDPVYTPMGVFITAWARYTTITAAQACFDRII

YCDTDSIHLTGTEIPDVIKDIVDPKKLGYWAHESTFKRAKYLRQK

TYIQDIYMKEVDGKLVEGSPDDYTTIKFSVKCAGMTDKIKKEVTF

ENFKVGFSRKMKPKPVQVPGGVVLVDDTFTIK

*Bacillus* phage Whiting18;
SEQ ID NO: 17:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYEITPDEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPAQMYSRLLPYGEPIVFEG

KYVWDEDYPLHIQHIRCEFELKEGYIPTIQIKRSRFYKGNEYLKS

SGGEIADLWVSNVDLELMKEHYDLYNVEYISGLKFKATTGLFKDF

IDKWTHIKTTSEGAIKQLAKLMLNSLYGKFASNPDVTGKVPYLKE

NGALGFRLGEEETKDPVYTPMGVFITAWARYTTITAAQACFDRII

YCDTDSIHLTGTETPDVIKDIVDPKKLGYWAHESTFKRAKYLRQK

TYIQDIYMKEVDGKLVEGSPDDYTTIKFSVKCAGMTDKIKKEVTF

DNFKVGFSRKMKPKPVQVPGGVVLVDDTFTIK

DNA polymerase *Bacillus* phage vB_BveP-Goe6;
SEQ ID NO: 18:
MPRKMYSCDFETTTKVEDCRVWAYGYMNIEDHSEYKIGNSLDEFM

AWVLKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYKITPEEYAYIKNDIQIIAEALLIQFKQ

GLDRMTAGSDSLKGFKDIITTKKFKKVFPTLSLGLDKEVRYAYRG

GFTWLNDRFKEKEIGEGMVFDVNSLYPSQMYSRLLPYGEPIVFEG

KYVWDEDYPLHIQHIRCEFELKEGYIPTIQIKRSRFYKGNEYLKS

SGGEIADLWLSNVDLELMKEHYDLYNVEYISGLKFKATTGLFKDF

IDKWTYIKTTSEGAIKQLAKLMLNSLYGKFASNPDVTGKVPYLKE

NGALGFRLGEEETKDPVYTPMGVFITAWARYTTITAAQACYDRII

YCDTDSIHLTGTEIPDVIKDIVDDNKLGYWAHESTFKRAKYLRQK

TYIQDIYMKEVNGKPVPASPDDYTFIKFSVKCAGMTDKIKKEVTF

DNFKVGFSRKMKPKPVQVPGGVVLVDDTFTIK

DNA polymerase protein *Bacillus* phage TBA3;
SEQ ID NO: 19:
MPRKMYSCDFETTTKVEDCRVWAYGYMNIEDHSEYKIGNSLDEFM

AWVMKVQADLYFHNLKFDGAFIINWLERNGFKWSADGLPNTYNTI

ISRMGQWYMIDICLGYKGKRKIHTVIYDSLKKLPFPVKKIAKDFK

LTVLKGDIDYHKERPVGYKITPEEYAYIKNDIQIIAEALLIQFKQ

GLDRMTAGSDSLKGFKDIITAKKFKKVFPTLSLGLDKEVRYAYRG

GFTWLNDRFKDKEIGEGMVFDVNSLYPSQMYTRLLPYGEPIVFEG

KYVWDEDYPLHIQHIRCEFELKEGYIPTIQIKRSRFYKGNEYLKS

SGGEIADLWLSNVDLELMKEHYDLYNVEYISGLKFKATTGLFKDF

IDKWTYIKTTSEGAIKQLAKLMLNSLYGKFASNPDVTGKVPYLKE

NGALGFRLGEEETKDPVYTPMGVFITAWARYTTITAAQACYDRII

YCDTDSIHLTGTEIPDVIKDIVDDNKLGYWAHESTFKRAKYLRQK

TYIQDIYMKEVDGKPVPASPDDYTFIKFSVKCAGMTDKIKKEVTF

ENFKVGFSRKMKPKPVQVPGGVVLVDDTFTIK

*Bacillus* phage M2;
SEQ ID NO: 20:
MSRKMFSCDFETTTKLDDCRVWAYGYMEIGNLDNYKIGNSLDEFM

QWVMEIQADLYFHNLKFDGAFIVNWLEQHGFKWSNEGLPNTYNTI

ISKMGQWYMIDICFGYKGKRKLHTVIYDSLKKLPFPVKKIAKDFQ

LPLLKGDIDYHTERPVGHEITPEEYEYIKNDIEIIARALDIQFKQ

GLDRMTAGSDSLKGFKDILSTKKFNKVFPKLSLPMDKEIRKAYRG

GFTWLNDKYKEKEIGEGMVFDVNSLYPSQMYSRPLPYGAPIVFQG

KYEKDEQYPLYIQRIRFEFELKEGYIPTIQIKKNPFFKGNEYLKN

SGVEPVELYLTNVDLELIQEHYELYNVEYIDGFKFREKTGLFKDF

IDKWTYVKTHEEGAKKQLAKLMLNSLYGKFASNPDVTGKVPYLKD

DGSLGFRVGDEEYKDPVYTPMGVFITAWARFTTITAAQACYDRII

YCDTDSIHLTGTEVPEIIKDIVDPKKLGYWAHESTFKRAKYLRQK

TYIQDIYVKEVDGKLKECSPDEATTTKFSVKCAGMTDTIKKKVTF

DNFAVGFSSMGKPKPVQVNGGVVLVDSVFTIK

DNA polymerase *Bacillus* phage vB_BsuP-Goe1;
SEQ ID NO: 21:
MSRKMFSCDFETTTKLDDCRVWAYGYMEIGNLDNYKIGNSLDEFM

KWVMEIQADLYFHNLKFDGAFIVNWLEQHGFKWSNEGLPNTYHTI

ISKMGQWYMIDICFGYRGKRKLHTVIYDSLKKLPFPVKKIAKDFQ

LPLLKGDIDYHTERPVGHEITPEEYEYIKNDIEIIARALDIQFKQ

GLDRMTAGSDSLKGFKDILSTKKFNKVFPKLSLPMDKEIRKAYRG

GFTWLNDKYKEKEIGEGMVFDVNSLYPSQMYSRPLPYGAPIVFQG

KYEKDEQYPLYIQRIRFEFELKEGYIPTIQIKKNPFFKGNEYLKN

SGAEPVELYLTNVDLELIQEHYELYNVEYIDGFKFREKTGLFKDF

-continued

IDKWTYVKTHEEGAKKQLAKLMLNSLYGKFASNPDVTGKVPYLKD

DGSLGFRVGDEEYKDPVYTPMGVFITAWARFTTITAAQACYDRII

YCDTDSIHLTGTEVPEIIKDIVDPKKLGYWAHESTFKRAKYLRQK

TYIQDIYVKEVDGKLKECSPDEATTTKFSVKCAGMTDTIKKKVTF

DNFKVGFSSMGKPKPVQVNGGVVLVDSVFTIK

DNA polymerase Beecentumtrevirus Nf;
SEQ ID NO: 22:
MSRKMFSCDFETTTKLDDCRVWAYGYMEIGNLDNYKIGNSLDEFM

QWVMEIQADLYFHNLKFDGAFIVNWLEQHGFKWSNEGLPNTYNTI

ISKMGQWYMIDICFGYRGKRKLHTVIYDSLKKLPFPVKKIAKDFQ

LPLLKGDIDYHTERPVGHEITPEEYEYIKNDIEIIARALDIQFKQ

GLDRMTAGSDSLKGFKDILSTKKFNKVFPKLSLPMDKEIRKAYRG

GFTWLNDKYKEKEIGEGMVFDVNSLYPSQMYSRPLPYGAPIVFQG

KYEKDEQYPLYIQRIRFEFELKEGYIPTIQIKKNPFFKGNEYLKN

SGVEPVELYLTNVDLELIQEHYELYNVEYIDGFKFREKTGLFKDF

IDKWTYVKTHEEGAKKQLAKLMLNSLYGKFASNPDVTGKVPYLKD

DGSLGFRVGDEEYKDPVYTPMGVFITAWARFTTITAAQACYDRII

YCDTDSIHLTGTEVPEIIKDIVDPKKLGYWAHESTFKRAKYLRQK

TYIQDIYVKEVDGKLKECSPDEATTTKFSVKCAGMTDTIKKKVTF

DNFAVGFSSMGKPKPVQVNGGVVLVDSVFTIK

DNA polymerase Beecentumtrevirus B103;
SEQ ID NO: 23:
MPRKMFSCDFETTTKLDDCRVWAYGYMEIGNLDNYKIGNSLDEFM

QWVMEIQADLYFHNLKFDGAFIVNWLEHHGFKWSNEGLPNTYNTI

ISKMGQWYMIDICFGYKGKRKLHTVIYDSLKKLPFPVKKIAKDFQ

LPLLKGDIDYHAERPVGHEITPEEYEYIKNDIEIIARALDIQFKQ

GLDRMTAGSDSLKGFKDILSTKKFNKVFPKLSLPMDKEIRRAYRG

GFTWLNDKYKEKEIGEGMVFDVNSLYPSQMYSRPLPYGAPIVFQG

KYEKDEQYPLYIQRIRFEFELKEGYIPTIQIKKNPFFKGNEYLKN

SGAEPVELYLTNVDLELIQEHYEMYNVEYIDGFKFREKTGLFKEF

IDKWTYVKTHEKGAKKQLAKLMFDSLYGKFASNPDVTGKVPYLKE

DGSLGFRVGDEEYKDPVYTPMGVFITAWARFTTITAAQACYDRII

YCDTDSIHLTGTEVPEIIKDIVDPKKLGYWAHESTFKRAKYLRQK

TYIQDIYAKEVDGKLIECSPDEATTTKFSVKCAGMTDTIKKKVTF

DNFRVGFSSTGKPKPVQVNGGVVLVDSVFTIK

DNA polymerase *Cytobacillus* phage Bfsp1;
SEQ ID NO: 24:
MARKQFMCDFETTTDIDDCRVWAYGYMEIGNKQNYKIGNSIEEFM

EWAEKSRSDIYFHNLKFDGSFIVNWLLNNGYTWEHMNEKSGKPKT

FTTIISNMGQWYMVDICYGRKGKRLLHTKIYDSLKKLPFSVKQIA

KAFKLPIMKGDIDYTKPRPVGYEITPDEEEYIYGDLFIVASALET

QFEQGLTKMTSGSDSLSGFKDILTPKMFDKFFPVLDLRIDSEIRK

AYRGGFTWVNDTIQGQTIGEGMVFDVNSLYPSRMYDCDLPYGTPE

KFEGEYTYNETYPLYIQVLKCSFELKEGYIPTIQLKQTARYRDNE

-continued

YLKSSNHEIETLYVTNVDLELIKEHYDLYDVEYLGGYMFKKKNDL

FREFIDYWMHIKITSTGAIKQLAKLMLNSLYGKFASNPVVTGKIP

YLKEDGRNGFKLPVKEGEFQEVKGKLIPVIDEEYKEPVYTAMGAF

ITAWARHYTITTAQKCFDRICYCDTDSIHIKGTEIPEVIKDIIDP

DKLGYWNHESTFIRAKFIRQKTYIEDTCFKMVEKNGKLEKVGAGL

DDYEFTEIEVKCAGMPENLKKYVTWENFNVFNEDMLLPARDGYWY

GKLMPKQVPGGVVLVESDFAIR

DNA polymerase *Bacillus* phage vB_Bpu_PumA1;
SEQ ID NO: 25:
MARKKYSCDFETTTDPLDCRVWAYGYMEIGKDSNYKIGNSLDEFM

EWVSKCNADLYFHNLRFDGEFILIWLLQNGFKWSDKRKPEPMTFN

GVISRDNAVYRYDICYGYTNSGKKIHTVIYDSYKKLPYPVKVIAK

AFNLTQLKGDIDYDAYRPVGHKITKEEYKYIYNDIKIIADALKIQ

FEQGLKKMTIGSDSLNGFKSIFGKKQFEKTFPVLDMLTDDFIRLS

YKGGFTWLNPKFANIVINKGRVYDVNSMYPAIMYNELLPYGVPVR

FKGKYEKDDKYPLYIQQISCIFELKEGKIPMIQVKNEPLKFKGSE

YLTSSKGYEVKLTLTNVELELFLENYKLNCVEYLGGYKFRGVRGL

FKTFIDKWMNIKMNSEGAIRELAKLMLNNLYGKFATNPDVTGKYP

ELKEDGSLGFKMKPRELSEPVYTAMGSFITAYGRCMTVRTGQSCY

DRFIYADTDSVHVAGNEDIPEIADKIDSKKLGYWDHEATFETGKY

VRSKAYFLNLYAKKVVKDGEEIIKPCGEEEATTRKRKVACAGMPE

TLRNIVPFEEFKIGYTGTRLAPRHVKGGIVLVDAPYTLKEDIWRY

A

FF38_11041 *Lucilia cuprina*;
SEQ ID NO: 26:
MARKRPIRITKNDRAEYKRLSKNAKSKLNRTVKNYGIDLSNDVDI

PKLSDFKTRKEFNDWKQKITSFTSRSNQEYQFRKNEYGVVASVKE

LNEIKRNTKKAQKIAKEKIDKAMKLDFYVEGERQGKVKDRIKLMK

KEEVAGVSVPVDFDFDKIQTRKRLEDKAGFMEERATGDYYRKKDI

QMKENFISMIEQGFNSDADEVIKKLKKIPPDDFVELTIVTDEIDF

RNYGSKNEGGINDEDKLEELNNTLNDYFNETTTDVNDCRVWAYGW

MEIGKTSNYKIGTDFNEFMEWMIHSSSRLYFHNLKFDGSFIVNWL

LHNGYTWTKRPSKEGQFSTLISKMGQWYGITICSGRDGRKKKLTT

IHDSLKKLPFPVRKIGKDFKLNVLKGDIDYHKPRPIGYEIDDEEY

QYIKNDIQIIAEALEVQTVQGLTGMTNGKDALDEFVNMSGKLYEK

LFPVFSLELNEEIRKAYRGGFTWLNPVYGTKKYVKDGIVFDVNSL

YPSQMYDRDLPCGVPIPFEGEYVYDKSHPLYIQKLTFEFELKENY

IPTIQLKNSRFGFKGNEYLSSSNGERITISVSSVDWELIREHYHV

YDVEFEKGWKFRSTKQAFRQYIDKWMLVKNMSAGAKKAIAKLMLN

SLYGKFATNPDITGKRPYLREDGSNGFELMEEEFRDPVYTPVGIF

ITSWARYTTITSAQKCYDRIIYCDTDSMHLEGLDVPESIKDIVAD

DVLGYWKKEGQFKQGKFIRQKTYMEEYYAKYVRDENGEIKYDDEK

-continued

PIKTICDKEESDTTIIEIKCAGMPDNIKKHVTFDNFDIGFTMEGK

LKPKQVYGGVVLVEETYTMK

DNA polymerase *Bacillus* phage BeachBum;
SEQ ID NO: 27:
MGNKKRKIYSCDFETTTDVNDCRVWAYGLMEIDGKFENYKEGNNI

DEFMEWAEKEQGDLYFHNLRFDGEFIVNWLLHKGYRENNTRKAGT

FNAVISSMGQWYKIDIYYGREGKKVFKTSIYDSLKKLPFPVKTIA

KAFKLPIEKGDIDYDAPRPVGHQITPDESKYIKNDVEIIARALHS

QLNTAKLTKMTIGSDALDGFKHSLHKSPKVSKRMYDHHFPVISNA

IHEEFKKAYRGGFTWANPKYAGKVIGNGLVFDVNSLYPSVMYDKP

LPYGLPVPFSGEYEYDETHPLFIQHIRCGFELKEGHIPTIQIKKN

FRFADNEYLHSSEGNILDLHVTNVDLALIKEHYTLYEEEYLQGYK

FKQVTGLFKNYIDYWSDKKINAEDPAIRQMAKLMLNSLYGKFGTS

IDVTGKEVFLKEDGSTGFRKGQKEERDPVYMPMGAFITAYARDVT

IRTAQKCYDRILYCDTDSIHLVGTEIPEAIKDRIHDKKLGYWAHE

STFWRAKFIRQKTYIEDLCMRFEGERVNGEWKFKMVEEKDITKAT

ARELSVKCAGMPAQVKQYVTFDNFGVDFKHDPNDFTEEEIKRKNI

KFKLKPTHRKGGQVLVPTPFTIK

DNA polymerase *Bacillus* phage Harambe;
SEQ ID NO: 28:
MGNKKRKIYSCDFETTTDVNDCRVWAYGLMEIDGKFENYKEGNNI

DEFMEWTEQEQGDLYFHNLRFDGEFIVNWLLHKGYRFNNTRKAGT

FNAVISSMGQWYKIDIYYGREGKKVFKTSIYDSLKKLPFPVKTIA

KAFKLPIEKGDIDYDAPRPVGHQITPDESKYIKNDVEIIARALHS

QLNTAKLTKMTIGSDALDGFKHSLHKSPKVSKRMYDHHFPVISNA

IHEEFKKAYRGGFTWANPKYAGKVIGNGLVFDVNSLYPSVMYDKP

LPYGLPVPFSGEYEYDETHPLFIQHIKCGFELKDGHIPTIQIKKN

FRFADNEYLHSSEGNILDLHVTNVDLALIKEHYTLYEEEYLQGYK

FKQVTGLFKNYIDYWSDKKINAEDPAIRQMAKLMLNSLYGKFGTS

IDVTGKEVFLKEDGSTGFRKGQKEERDPVYMPMGAFITAYARDVT

IRTAQKCYDRILYCDTDSIHLVGTEIPEAIKDRIHDKKLGYWAHE

STFWRAKFIRQKTYIEDLCMRFEGEKVNGEWKFKMVEEKDITKAT

ARELSVKCAGMPAQVKQYVTFDNFGVDFKHDPNDYTDEEIKRKNI

KFKLKPTHRKGGQVLVPTPFTIK

*Enterococcus faecium* HP.1;
SEQ ID NO: 29:
MIKKYTGDFETTTDLNDCRVWSWGVCDIDNVDNITFGLDIDSFFE

WCEMQGSTDIYFHNEKFDGEFMLSWLFKNGFKWSKETKEERTFST

LISNMGQWYALEICWEVNYATTKSGKTKKEKVRTIIYDSLKKYPF

PVKQIAEAFNFPIKKGEIDYTKERPIGYKPTKDEWEYLKNDIQIM

AMALKIQFDQGLTRMTRGSDALGDYQDWVKTTYGKSRFKQWFPIL

SLGFDKDLRKAYKGGFTWVNKVFQGKEIGDGIVFDVNSLYPSQMY

VRPLPYGTPLFYEGEYKPNNDYPLYIQNIKVRFRLKEGYIPTIQV

KQSSLFIQNEYLDSSVNKLGVDELIDLTLTNVDLELFFEHYDILE

-continued

IHYTYGYMFKASCDMFKGWIDKWIEVKNTTEGARKANAKGMLNSL

YGKFGTNPDITGKVPYMGEDGIVRLTLGEEELRDPVYVPLASFVT

AWGRYTTITTAQKCFDRIIYCDTDSIHLVGTEVPEAIDHLVDPKK

LGYWGHESTFQRAKFIRQKTYVEEIDGELNVKCAGMPDRIKELVT

FDNFEVGFSSYGKLLPKRTQGGVVLVDTMFTIK

*Enterococcus faecium* HP.2;
SEQ ID NO: 30:
MIKKYTGDFETTTDLNDCRVWSWGVCDIDNVDNITFGLDIDSFFE

WCEMQGSTDIYFHNEKFDGEFMLSWLFKNGFKWSKETKEERTFST

LISNMGQWYALEICWEVNYTTTKSGKTKKEKSRTIIYDSLKKYPF

PVKQIAEAFNFPIKKGEIDYTKERPIGYKPTKDEWEYLKNDIQIM

AMALKIQFDQGLTRMTRGSDALGDYQDWVKTTYGKSRFKQWFPIL

SLGFDKDLRKAYKGGFTWVNKVFQGKEIGDGIVFDVNSLYPSQMY

VRPLPYGTPLFYEGEYKPNNDYPLYIQNIKVRFRLKEGYIPTIQV

KQSSLFIQNEYLDSSVNKLGVDELIDLTLTNVDLELFFEHYDILE

IHYTYGYMFKASCDMFKGWIDKWIEVKNTTEGARKANAKGMLNSL

YGKFGTNPDITGKVPYMGEDGIVRLTLGEEELRDPVYVPLASFVT

AWGRYTTITTAQKCFDRIIYCDTDSIHLVGTEVPEAIDHLVDPKK

LGYWGHESTFQRAKFIRQKTYVEEIDGELNVKCAGMPDRIKELVT

FDNFEVGFSSYGKLLPKRTQGGVVLVDTMFTIK

*Enterococcus faecium* HP.3;
SEQ ID NO: 31:
MMIKKYTGDFETTTDLNDCRVWSWGVCDIDNVDNITFGLEIDSFF

EWCKMQGSTDIYFHNEKFDGEFMLSWLFKNGFKWCKEAKEDRTFS

TLISNMGQWYALEICWEVNYTTTKSGKTKKEKSRTIIYDSLKKYP

FPVKQIAEAFNFPIKKGEIDYTKERPIGYKPTKDEWEYLKNDIQI

MAMALKIQFDQGLTRMTRGSDALGDYKDWLKATHGKTTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTSEGARKANAKGMLNS

LYGKFGTNPDITGKVPYMGEDGIVRLTLGEEELRDPVYVPLASFV

TAWGRYTTITTAQKCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.4;
SEQ ID NO: 32:
MMIKKYTGDFETTTDLNDCRVWSWGVCDIDNVDNITFGLEIDSFF

EWCKMQGSTDIYFHNEKFDGEFMLSWLFKNGFKWCKEAKEDRTFS

TLISNMGQWYALEICWEVNYTTTKSGKTKKEKSRTIIYDSLKKYP

FPVKQIAEAFNFPIKKGEIDYTKERPIGYKPTKDEWEYLKNDIQI

MAMALKIQFDQGLTRMTRGSDALGDYQDWVKTTYGKSRFKQWFPI

LSLGFDKDLRKAYKGGFTWVNKVFQGKEIGDGIVFDVNSLYPSQM

-continued

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTSEGARKANAKGMLNS

LYGKFGTNPDITGKVPYMGEDGIVRLTLGEEELRDPVYVPLASFV

TAWGRYTTITTAQKCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.5;
SEQ ID NO: 33:
MMIKKYTGDFETTTDLNDCRVWSWGVCDIDNVDNITFGLDIDSFF

EWCEMQGSTDIYFHNEKFDGEFMLSWLFKNGFKWSKETKEERTFS

TLISNMGQWYALEICWEVNYTTTKSGKTKKEKSRTIIYDSLKKYP

FPVKQIAEAFNFPIKKGEIDYTKERPIGYKPTKDEWEYLKNDIQI

MAMALKIQFDQGLTRMTRGSDALGDYQDWVKTTYGKSRFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQKCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.6;
SEQ ID NO: 34:
MIKKYTGDFETTTDLNDCRVWSWGVCDIDNVDNITFGLDIDSFFE

WCEMQGSTDIYFHNEKFDGEFMLSWLFKNGFKWSKETKEERTFST

LISNMGQWYALEICWEVNYATTKSGKTKKEKVRTIIYDSLKKYPF

PVKQIAEAFNFPIKKGEIDYTKERPVGYNPTDDEWDYLKNDIQIM

AMALKIQFDQGLTRMTRGSDALGDYKDWLKATHGKSTFKQWFPIL

SLGFDKDLRKAYKGGFTWVNKVFQGKEIGDGIVFDVNSLYPSQMY

VRPLPYGTPLFYEGEYKPNNDYPLYIQNIKVRFRLKEGYIPTIQV

KQSSLFIQNEYLDSSVNKLGVDELIDLTLTNVDLELFFEHYDILE

IHYTYGYMFKASCDMFKGWIDKWIEVKNTTEGARKANAKGMLNSL

YGKFGTNPDITGKVPYMGEDGIVRLTLGEEELRDPVYVPLASFVT

AWGRYTTITTAQRCFDRIIYCDTDSIHLVGTDVPEAIEHLVDPKK

LGYWGHESTFQRAKFIRQKTYVEEIDGELNVKCAGMPDRIKELVT

FDNFEVGFSSYGKLLPKRTQGGVVLVDTMFTIK

*Enterococcus faecium* HP.7;
SEQ ID NO: 35:
MIKKYTGDFETTTDLNDCRVWSWGVCDIDNVDNITFGLDIDSFFE

WCEMQGSTDIYFHNEKFDGEFMLSWLFKNGFKWSKETKEERTFST

LISNMGQWYALEICWEVNYATTKSGKTKKEKVRTIIYDSLKKYPF

PVKQIAEAFNFPIKKGEIDYTKERPVGYNPTDDEWDYLKNDIQIM

AMALKIQFDQGLTRMTRGSDALGDYKDWLKATHGKSTFKQWFPIL

-continued

SLGFDKDLRKAYKGGFTWVNKVFQGKEIGDGIVFDVNSLYPSQMY

VRPLPYGTPLFYEGEYKPNNDYPLYIQNIKVRFRLKEGYIPTIQV

KQSSLFIQNEYLDSSVNKLGVDELIDLTLTNVDLELFFEHYDILE

IHYTYGYMFKASCDMFKGWIDKWIEVKNTTEGARKANAKGMLNSL

YGKFGTNPDITGKVPYMGEDGIVRLTLGEEELRDPVYVPLASFVT

AWGRYTTITTAQRCFDRIIYCDTDSIHLVGTDAPEAIEHLVDPKK

LGYWGHESTFQRAKFIRQKTYVEEIDGELNVKCAGMPDRIKELVT

FDNFEVGFSSYGKLLPKRTQGGVVLVDTMFTIK

*Enterococcus faecium* HP.8;
SEQ ID NO: 36:
MIKKYTGDFETTTDLNDCRVWSWGVCDIDNVNNITFGLDIDSFFE

WCEMQGSTDIYFHNEKFDGEFMLSWLFKNGFKWSKETKEERTFST

LISNMGQWYALEICWEVNYTTTKSGKTKKEKVRTIIYDSLKKYPF

PVKQIAEAFNFPIKKGEIDYTKERPVGYNPTDDEWDYLKNDIQIM

AMALKIQFDQGLTRMTRGSDALGDYKDWLKATHGKSTFKQWFPIL

SLGFDKDLRKAYKGGFTWVNKVFQGKEIGDGIVFDVNSLYPSQMY

VRPLPYGTPLFYEGEYKPNNDYPLYIQNIKVRFRLKEGYIPTIQV

KQSSLFIQNEYLDSSVNKLGVDELIDLTLTNVDLELFFDHYDILE

IHYTYGYMFKASCDMFKGWIDKWIEVKNTTEGARKANAKGMLNSL

YGKFGTNPDITGKVPYMGEDGIVRLTLGEEELRDPVYVPLASFVT

AWGRYTTITTAQRCFDRIIYCDTDSIHLVGTEVPEAIDHLVDPKK

LGYWGHESTFQRAKFIRQKTYVEEIDGELNVKCAGMPDRIKELVT

FDNFEVGFSSYGKLLPKRTQGGVVLVDTMFTIK

*Enterococcus faecium* HP.9;
SEQ ID NO: 37:
MIKKYTGDFETTTDLNDCRVWSWGVCDIDNVDNITFGLDIDSFFE

WCEMQGSTDIYFHNEKFDGEFMLSWLFKNGFKWSKETKEERTFST

LISNMGQWYALEICWEVNYTTTKSGKTKKEKVRTIIYDSLKKYPF

PVKQIAEAFNFPIKKGEIDYTKERPVGYNPTDDEWDYLKNDIQIM

AMALKIQFDQGLTRMTRGSDALGDYKDWLKATHGKSTFKQWFPIL

SLGFDKDLRKAYKGGFTWVNKVFQGKEIGDGIVFDVNSLYPSQMY

VRPLPYGTPLFYEGEYKPNNDYPLYIQNIKVRFRLKEGYIPTIQV

KQSSLFIQNEYLDSSVNKLGVDELIDLTLTNVDLELFFEHYDILE

IHYTYGYMFKASCDMFKGWIDKWIEVKNTTEGARKANAKGMLNSL

YGKFGTNPDITGKVPYMGEDGIVRLTLGEEELRDPVYVPLASFVT

AWGRYTTITTAQRCFDRIIYCDTDSIHLVGTDVPEAIEHLVDPKK

LGYWGHESTFQRAKFIRQKTYVEEIDGELNVKCAGMPDRIKELVT

FDNFEVGFSSYGKLLPKRTQGGVVLVDTMFTIK

*Enterococcus faecium* HP.10;
SEQ ID NO: 38:
MIKKYTGDFETTTDLNDCRVWSWGVCDIDNVDNITFGLDIDSFFE

WCEMQGSTDIYFHNEKFDGEFMLSWLFKNGFKWSKETKEERTFST

LISNMGQWYALEICWEVNYTTTTKSGKMKKEKVRTIIYDSLKKYP

-continued

FPVKQIAEAFNFPIKKGEIDYTKERPVGYNPTDDEWDYLKNDIQI

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFDHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQRCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.11;
SEQ ID NO: 39:
MMIKKYTGDFETTTDLNDCRVWSWGVCDIDNVDNITFGLDIDSFF

EWCEMQGSTDIYFHNEKFDGEFMLSWLFKNGFKWSKETKEERTFS

TLISNMGQWYALEICWEVNYATTKSGKTKKEKVRTIIYDSLKKYP

FPVKQIAEAFNFPIKKGEIDYTKERPVGYNPTDDEWDYLKNDIQI

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQRCFDRIIYCDTDSIHLVGTDVPEAIEHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.12;
SEQ ID NO: 40:
MMIKKYTGDFETTTDLNDCRVWSWGVCDIDNVDNITFGLEIDSFF

EWCKMQGSTDIYFHNEKFDGEFMLSWLFKNGFKWSKEAKEDRTFS

TLISNMGQWYALEICWEVNYTTTKSGKTKKDKVRTIIYDSLKKYP

FPVKQIAEAFDFPIKKGEIDYNKERPIGYNPTDDEWEYLKNDIQI

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQKCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.13;
SEQ ID NO: 41:
MMIKKYTGDFETTTDLNDCRVWSWGVCDIDNVDNITFGLDIDSFF

EWCEMQGSTDIYFHNEKFDGEFMLSWLFKNGFKWSKETKEERTFS

-continued

TLISNMGQWYALEICWNIKYTTTKSGKTKKEKVRTIIYDSLKKYP

FPVKQIAEAFNFSIKKGEIDYTKERPVGYNPTDDEWDYLKNDIQI

MAMALKIQFDQGLTRMTRGSDALGDYKDWLKATHGKSTFKQWFPV

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLESSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQRCFDRIIYCDTDSIHLTGTEVPETIEHLVDSK

KLGYWKHESTFQRAKFIRQKTYVEEIDGELNVKCAGMPDRIKELV

TFDNFEVGFSSYGKLLPKRTQGGVVLVDTMFTIK

*Enterococcus faecium* HP.14;
SEQ ID NO: 42:
MMIKKYTGDFETTTDLNDCRVWSWGVCDIDNVNNITFGLDIDSFF

EWCEMQGSTDIYFHNEKFDGEFMLSWLFKNGFKWSKETKEERTFS

TLISNMGQWYALEICWEVNYTTTKSGKTKKEKVRTIIYDSLKKYP

FPVKQIAEAFNFPIKKGEIDYTKERPVGYNPTDDEWDYLKNDIQI

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFDHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQRCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.15;
SEQ ID NO: 43:
MMIKKYTGDFETTTDLNDCRVWSWGVCDIDNVDNITFGLEIDSFF

EWCKMQGSTDIYFHNEKFDGEFMLSWLFKNGFKWCKEAKEDRTFS

TLISNMGQWYALEICWEVNYTTTKSGKTKKEKSRTIIYDSLKKYP

FPVKQIAEAFNFPIKKGEIDYTKERPIGYKPTKDEWEYLKNDIQI

MAMALKIQFDQGLTRMTRGSDALGDYKDWLKATHGKTTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQKCFDRIIYCDTDSIHLVGTEVPEAIDHLVDPK

KLGYWGHESTFQRAKFIRQKTYVEEIDGELNVKCAGMPDRIKELV

TFDNFEVGFSSYGKLLPKRTQGGVVLVDTMFTIK

-continued

*Enterococcus faecium* HP. 16;
SEQ ID NO: 44:
MMIKKYTGDFETTTDLNDCRVWSWGVCDIDNVDNITFGLEIDSFF
EWCKMQGSTDIYFHNEKFDGEFMLSWLFKNGFKWCKEAKEDRTFS
TLISNMGQWYALEICWEVNYTTTKSGKTKKEKSRTIIYDSLKKYP
FPVKQIAEAFNFPIKKGEIDYTKERPIGYKPTKDEWEYLKNDIQI
MAMALKIQFDQGLTRMTRGSDALGDYQDWVKTTYGKSRFKQWFPI
LSLGFDKDLRKAYKGGFTWVNKVFQGKEIGDGIVFDVNSLYPSQM
YVRPLPYGTPLFYEGEYKPNNDYPLYIQNIKVRFRLKEGYIPTIQ
VKQSSLFIQNEYLDSSVNKLGVDELIDLTLTNVDLELFFEHYDIL
EIHYTYGYMFKASCDMFKGWIDKWIEVKNTTEGARKANAKGMLNS
LYGKFGTNPDITGKVPYMGEDGIVRLTLGEEELRDPVYVPLASFV
TAWGRYTTITTAQKCFDRIIYCDTDSIHLVGTEVPEAIDHLVDPK
KLGYWGHESTFQRAKFIRQKTYVEEIDGELNVKCAGMPDRIKELV
TFDNFEVGFSSYGKLLPKRTQGGVVLVDTMFTIK

*Enterococcus faecium* HP.17;
SEQ ID NO: 45:
MMIKKYTGDFETTTDLNDCRVWSWGVCDIDNFDNITFGLDIDSFF
EWCEMQGSTDIYFHNEKFDGEFMLSWLFKNGFKWSKETKEERTFS
TLISNMGQWYALEICWEVNYTTTKSGKTKKEKVRTIIYDSLKKYP
FPVKQIAEAFNFPIKKGEIDYTKERPVGYNPTDDEWDYLKNDIQI
MAMALKIQFDQGLTRMTRGSDALGDYKDWLKATHGKSTFKQWFPI
LSLGFDKDLRKAYKGGFTWVNKVFQGKEIGDGIVFDVNSLYPSQM
YVRPLPYGTPLFYEGEYKPNNDYPLYIQNIKVRFRLKEGYIPTIQ
VKQSSLFIQNEYLDSSVNKLGVDELIDLTLTNVDLELFFDHYDIL
EIHYTYGYMFKASCDMFKGWIDKWIEVKNTTEGARKANAKGMLNS
LYGKFGTNPDITGKVPYMGEDGIVRLTLGEEELRDPVYVPLASFV
TAWGRYTTITTAQRCFDRIIYCDTDSIHLVGTEVPEAIDHLVDPK
KLGYWGHESTFQRAKFIRQKTYVEEIDGELNVKCAGMPDRIKELV
TFDNFEVGFSSYGKLLPKRTQGGVVLVDTMFTIK

*Enterococcus faecium* HP.18;
SEQ ID NO: 46:
MIKKYTGDFETTTDLNDCRVWSWGVCDIDNVDNITFGLDIDSFFE
WCEMQGSTDIYFHNEKFDGEFMLSWLFKNGFKWSKETKEERTFST
LISNMGQWYALEICWEVNYATTKSGKTKKEKVRTIIYDSLKKYPF
PVKQIAEAFNFPIKKGEIDYTKERPVGYNPTDDEWEYLKNDIQIM
AMALKIQFDQGLTRMTRGSDALGDYKDWLKATHGKSTFKQWFPIL
SLGFDKDLRKAYKGGFTWVNKVFQGKEIGDGIVFDVNSLYPSQMH
VRPLPYGTPLFYEGEYKPNNDYPLYIQNIKVRFRLKEGYIPTIQV
KQSSLFIQNEYLDSSVNKLGVDELIDLTLTNVDLELFFEHYDILE
IHYTYGYMFKASCDMFKGWIDKWIEVKNTTEGARKANAKGMLNSL
YGKFGTNPDITGKVPYMGEDGIVRLTLGEEELRDPVYVPLASFVT
AWGRYTTITTAQRCFDRIIYCDTDSIHLVGTDVPEAIEHLVDPKK
LGYWGHESTFQRAKFIRQKTYVEEIDGELNVKCAGMPDRIKELVT
FDNFEVGFSSYGKLLPKRTQGGVVLVDTMFTIK

*Enterococcus faecium* HP. 19;
SEQ ID NO: 47:
MIKKYTGDFETTTDLNDCRVWSWGVCDIDNVDNITFGLDIDSFFE
WCEMQGSTDIYFHNEKFDGEFMVSWLFKNGFKWSKETKEERTFST
LISNMGQWYALEICWEVNYTTTKSGKTKKEKVRTIIYDSLKKYPF
PVKQIAEAFNFPIKKGEIDYTKERPVGYNPTDDEWDYLKNDIQIM
AMALKIQFDQGLTRMTRGSDALGDYKDWLKATHGKLTFKQWFPIL
SLGFDKDLRKAYKGGFTWVNKVFQGKEIGDGIVFDVNSLYPSQMY
VRPLPYGTPLFYEGEYKPNNDYPLYIQNIKVRFRLKEGYIPTIQV
KQSSLFIQNEYLDSSVNKLGVDELIDLTLTNVDLELFFAHYDILE
IHYTYGYMFKASCGMFKGWIDKWIEVKNTTEGARKANAKGMLNSL
YGKFGTNPDITGKVPYMGEDGIVRLTLGEEELRDPVYVPLASFVT
AWGRYTTVTTAQRCFDRIIYCDTDSIHLVGTDVPEAIEHLVDPKK
LGYWGHESTFQRAKFIRQKTYVEEIDGELNVKCAGMPDRIKELVT
FDNFEVGFSSYGKLLPKRTQGGVVLVDTMFTIK

*Enterococcus faecium* HP.20;
SEQ ID NO: 48:
MMIKKYTGDFETTTDLNDCRVWSWGVCDIDNVDNITFGLEIDSFF
EWCKMQGSTDIYFHNEKFDGEFMLSWLFKNGFKWCKEAKEDRTFS
TLISNMGQWYALEICWEVNYATTKSGKTKKEKVRTIIYDSLKKYP
FPVKQIAEAFNFPIKKGEIDYTKERPVGYNPTDDEWDYLKNDIQI
MAMALKIQFDQGLTRMTRGSDALGDYKDWLKATHGKSTFKQWFPI
LSLGFDKDLRKAYKGGFTWVNKVFQGKEIGDGIVFDVNSLYPSQM
YVRPLPYGTPLFYEGEYKPNNDYPLYIQNIKVRFRLKEGYIPTIQ
VKQSSLFIQNEYLDSSVNKLGVDELIDLTLTNVDLELFFEHYDIL
EIHYTYGYMFKASCDMFKGWIDKWIEVKNTTEGARKANAKGMLNS
LYGKFGTNPDITGKVPYMGEDGIVRLTLGEEELRDPVYVPLASFV
TAWGRYTTITTAQRCFDRIIYCDTDSIHLVGTDVPEAIEHLVDPK
KLGYWGHESTFQRAKFIRQKTYVEEIDGELNVKCAGMPDRIKELV
TFDNFEVGFSSYGKLLPKRTQGGVVLVDTMFTIK

*Enterococcus faecium* HP. 21;
SEQ ID NO: 49:
MMIKKYTGDFETTTDLNDCRVWSWGVCDIDNVDNITFGLDIDSFF
EWCEMQGSTDIYFHNEKFDGEFMLSWLFKNGFKWSKETKEERTFS
TLISNMGQWYALEICWEVNYATTKSGKTKKEKVRTIIYDSLKKYP
FPVKQIAEAFNFPIKKGEIDYTKERPVGYNPTDDEWEYLKNDIQI
MAMALKIQFDQGLTRMTRGSDALGDYKDWLKATHGKSTFKQWFPI
LSLGFDKDLRKAYKGGFTWVNKVFQGKEIGDGIVFDVNSLYPSQM
HVRPLPYGTPLFYEGEYKPNNDYPLYIQNIKVRFRLKEGYIPTIQ
VKQSSLFIQNEYLDSSVNKLGVDELIDLTLTNVDLELFFEHYDIL
EIHYTYGYMFKASCDMFKGWIDKWIEVKNTTEGARKANAKGMLNS
LYGKFGTNPDITGKVPYMGEDGIVRLTLGEEELRDPVYVPLASFV -continued

TAWGRYTTITTAQRCFDRIIYCDTDSIHLVGTDVPEAIEHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.22;
SEQ ID NO: 50:
MMIKKYTGDFETTTDLNDCRVWSWGVCDIDNVDNITFGLDIDSFF

EWCEMQGSTDIYFHNEKFDGEFMLSWLFKNGFKWSKETKEERTFS

TLISNMGQWYALEICWEVNYATTKSGKTKKEKVRTIIYDSLKKYP

FPVKQIAEAFNFPIKKGEIDYTKERPVGYNPTDDEWDYLKNDIQI

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTTEGARKANAKGMLNS

LYGKFGTNSDITGKVPYMGEDGIVRLTLGEEELRDPVYVPLASFV

TAWGRYTTITTAQRCFDRIIYCDTDSIHLVGTDVPEAIEHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.23;
SEQ ID NO: 51:
MMIKKYTGDFETTTDLNDCRVWSWGVCDIDNVDNITFGLDIDSFF

EWCEMQGSTDIYFHNEKFDGEFMLSWLFKNGFKWSKETKEERTFS

TLISNMDQWYALEICWEVNYATTKSGKTKKEKVRTIIYDSLKKYP

FPVKQIAEAFNFPIKKGEIDYTKERPVGYNPTDDEWDYLKNDIQI

-continued

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLDSSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQRCFDRIIYCDTDSIHLVGTDVPEAIEHLVDPK

KLGYWGHESTFQRAKFIRQKTYVEEIDGELNVKCAGMPDRIKELV

TFDNFEVGFSSYGKLLPKRTQGGVVLVDTMFTIK

*Enterococcus faecium* HP.24;
SEQ ID NO: 52:
MMIKKYTGDFETTTDLNDCRVWSWGVCDIDNVDNITFGLDIDSFF

EWCEMQGSTDIYFHNEKFDGEFMLSWLFKNGFKWSKETKEERTFS

TLISNMGQWYALEICWNINYTTTKSGKTKKEKVRTIIYDSLKKYP

FPVKQIAEAFNFPIKKGEIDYTKERPVGYNPTDDEWDYLKNDIQI

MAMALKIQFDQGLTRMTRGSDALGDYKDWLKATHGKSTFKQWFPI

LSLGFDKDLRKAYKGGFTWVNKVFQGKEIGDGIVFDVNSLYPSQM

YVRPLPYGTPLFYEGEYKPNNDYPLYIQNIKVRFRLKEGYIPTIQ

VKQSSLFIQNEYLESSVNKLGVDELIDLTLTNVDLELFFEHYDIL

EIHYTYGYMFKASCDMFKGWIDKWIEVKNTTEGARKANAKGMLNS

LYGKFGTNPDITGKVPYMGEDGIVRLTLGEEELRDPVYVPLASFV

TAWGRYTTITTAQRCFDRIIYCDTDSIHLVGTDVPEAIEHLVDPK

KLGYWGHESTFQRAKFIRQKTYVEEIDGELNVKCAGMPDRIKELV

TFDNFEVGFSSYGKLLPKRTQGGVVLVDTMFTIK

What is claimed is:

1. A polymerase comprising an amino acid sequence that is at least 90% identical to SEQ ID NO: 1; comprising an amino acid substitution, wherein said amino acid substitution is A324T, A394G, A394K, A394N, A394Q, A394V D219N, D34A, D34E, D34N, D34Q, F198L, F47I, G401A, G401L, G401V, G417A, G417K, G417N, G417Q, G417R, G579A, G579S, G579T, G579Y, H485L, I119A, I119G, I119L, I119V, I179F, I378A, I378G, I378L, I378V, I93A, I93G, I93N, I93Q, K135G, K311N, K311Q, K311R, K366A, K366G, K366H, K366N, K366Q, K366R, L216A, L216F, L216G, L216P, L216W, L216Y, L381Q, L462A, L462G, L462I, L462V, L567M, P87A, P87G, P87S, P87T, P87Y, R552A, R552N, R552Q, S192A, S192C, S192G, S260N, S260Q, S487C, S578A, S578G, S578I, S578L, S578T, S578V, T203S, T231A, T231I, T231V, T434A, T434G, T434Y, V565A, V565G, V565M, W436R, Y343C, Y500A, Y500F, or Y500G.

2. The polymerase of claim 1, wherein said the amino acid substitution is: D34E, F47I, P87S, I93N, I119V, I179F, S192C, F198L, T203S, D219N, T231I, K311R, A324T, Y343C, K366R, I378V, L381Q, A394V, G401V, G417R, L462I, H485L, S487C, Y500F, K539E, R552Q, V565M, L567M, S578G, or G579S.

3. A method of incorporating a nucleotide into a nucleic acid sequence comprising combining in a reaction vessel: (i) a nucleic acid template, (ii) a nucleotide solution comprising a plurality of nucleotides, and (iii) a polymerase, wherein the polymerase is a polymerase of claim 1.

4. A method of amplifying a nucleic acid sequence, said method comprising:

a) hybridizing a nucleic acid template to a primer to form a primer-template hybridization complex;

b) contacting said primer-template hybridization complex with a DNA polymerase and a plurality of nucleotides, wherein the DNA polymerase is the polymerase of claim 1; and c) subjecting the primer-template hybridization complex to conditions which enable the polymerase to incorporate one or more nucleotides into the primer-template hybridization complex to generate amplification products, thereby amplifying a nucleic acid sequence.

5. A method of amplifying a template polynucleotide, the method comprising: contacting a template polynucleotide with an amplification primer, and amplifying the template polynucleotide by extending an amplification primer with a polymerase to generate an extension product comprising one or more complements of the template polynucleotide; wherein said polymerase is a polymerase of claim 1.

6. The method of claim 5, comprising amplifying the template polynucleotide in a cell.

7. The method of claim 5, comprising amplifying the template polynucleotide in a tissue.

8. The method of claim 5, comprising amplifying the template polynucleotide on a solid support.

9. The polymerase of claim 1, further comprising a glutamic acid, aspartic acid, alanine, or glycine at an amino acid position corresponding to position 135.

10. The polymerase of claim 1, further comprising K135E.

11. The polymerase of claim 1, comprising G417A, G417K, G417N, or G417Q.

12. The polymerase of claim 1, comprising A394V or A394K.

13. The polymerase of claim 1, further comprising K536E.

14. The polymerase of claim 1, comprising P87S and I93N.

15. The polymerase of claim 14, further comprising I378V, and S578V.

16. The polymerase of claim 1, comprising L381Q and H485L.

17. The polymerase of claim 1, further comprising P87A, P87G, P87S, P87T, or P87Y.

18. The polymerase of claim 1, comprising F198L.

19. The polymerase of claim 1, comprising G417R.

20. The polymerase of claim 1, further comprising a glutamic acid, aspartic acid, alanine, or glycine at an amino acid position corresponding to position 135; and a glutamic acid, aspartic acid, alanine, glycine, or threonine at an amino acid position corresponding to position 536.

* * * * *